US009328149B2

(12) United States Patent
Rao et al.

(10) Patent No.: US 9,328,149 B2
(45) Date of Patent: May 3, 2016

(54) **MUTATED AND BACTERIOPHAGE T4 NANOPARTICLE ARRAYED F1-V IMMUNOGENS FROM *YERSINIA PESTIS* AS NEXT GENERATION PLAGUE VACCINES**

(71) Applicant: The Catholic University of America, Washington, DC (US)

(72) Inventors: Venigalla B. Rao, Silver Spring, MD (US); Pan Tao, Silver Spring, MD (US)

(73) Assignee: The Catholic University of America, Washington, DC (US)

( * ) Notice: Subject to any disclaimer, the term of this patent is extended or adjusted under 35 U.S.C. 154(b) by 8 days.

(21) Appl. No.: 14/320,731

(22) Filed: Jul. 1, 2014

(65) Prior Publication Data

US 2015/0017198 A1    Jan. 15, 2015

Related U.S. Application Data

(60) Provisional application No. 61/845,487, filed on Jul. 12, 2013.

(51) Int. Cl.
*A61K 39/00* (2006.01)
*C07K 14/24* (2006.01)
*A61K 39/02* (2006.01)
*C07K 14/005* (2006.01)

(52) U.S. Cl.
CPC .............. *C07K 14/24* (2013.01); *A61K 39/0291* (2013.01); *C07K 14/005* (2013.01); *A61K 2039/5256* (2013.01); *C07K 2319/21* (2013.01); *C07K 2319/40* (2013.01); *C07K 2319/735* (2013.01); *C12N 2795/10123* (2013.01)

(58) Field of Classification Search
None
See application file for complete search history.

(56) References Cited

U.S. PATENT DOCUMENTS

| | | | |
|---|---|---|---|
| 5,985,285 A | 11/1999 | Titball et al. | |
| 8,148,130 B2 | 4/2012 | Alving et al. | |
| 8,685,694 B2 | 4/2014 | Rao | |
| 2011/0250263 A1 | 10/2011 | Rao | |

FOREIGN PATENT DOCUMENTS

WO        98/24912        6/1998

OTHER PUBLICATIONS

Perry RD, Fetherston JD (1997) Yersinia pestis—etiologic agent of plague. Clin Microbiol Rev 10: 35-66.
Kool JL (2005) Risk of person-to-person transmission of pneumonic plague. Clin Infect Dis 40: 1166-1172.
Rosenzweig JA, Jejelowo O, Sha J, Erova TE, Brackman SM, et al. (2011) Progress on plague vaccine development. Appl Microbiol Biotechnol 91: 265-286.
Zilinskas RA (2006) The anti-plague system and the Soviet biological warfare program. Crit Rev Microbiol 32: 47-64.
Smiley ST (2008) Current challenges in the development of vaccines for pneumonic plague. Expert Rev Vaccines 7: 209-221.
Sha J, Kirtley ML, van Lier CJ, Wang S, Erova TE, et al. (2012) Deletion of Braun lipoprotein encoding gene and altering the function of lipopolysaccharide attenuate plague bacterium. Infect Immun Dec 28: Epub ahead of print.
Feodorova VA, Corbel MJ (2009) Prospects for new plague vaccines. Expert Rev Vaccines 8: 1721-1738.
Williamson ED, Oyston PC (2012) The natural history and incidence of *Yersinia pestis* and prospects for vaccination. J Med Microbiol 61: 911-918.
Zavialov AV, Berglund J, Pudney AF, Fooks LJ, Ibrahim TM, et al. (2003) Structure and biogenesis of the capsular F1 antigen from Yersinia pestis: preserved folding energy drives fiber formation. Cell 113: 587-596.
Stenseth NC, Atshabar BB, Begon M, Belmain SR, Bertherat E, et al. (2008) Plague: past, present, and future. PLoS Med 5: e3.
Derewenda U, Mateja A, Devedjiev Y, Routzahn KM, Evdokimov AG, et al. (2004) The structure of Yersinia pestis V-antigen, an essential virulence factor and mediator of immunity against plague. Structure 12: 301-306.
Brubaker RR (2003) Interleukin-10 and inhibition of innate immunity to Yersiniae: roles of Yops and LcrV (V antigen). Infect Immun 71: 3673-3681.
Williamson ED, Eley SM, Griffin KF, Green M, Russell P, et al. (1995) A new improved sub-unit vaccine for plague: the basis of protection. FEMS Immunol Med Microbiol 12: 223-230.
Anderson GW, Jr., Heath DG, Bolt CR, Welkos SL, Friedlander AM (1998) Short- and long-term efficacy of single-dose subunit vaccines against Yersinia pestis in mice. Am J Trop Med Hyg 58: 793-799.
Heath DG, Anderson GW, Jr., Mauro JM, Welkos SL, Andrews GP, et al. (1998) Protection against experimental bubonic and pneumonic plague by a recombinant capsular F1-V antigen fusion protein vaccine. Vaccine 16: 1131-1137.
Williamson ED (2009) Plague. Vaccine 27 Suppl 4: D56-60.
Williamson ED, Flick-Smith HC, Lebutt C, Rowland CA, Jones SM, et al. (2005) Human immune response to a plague vaccine comprising recombinant F1 and V antigens. Infect Immun 73: 3598-3608.

(Continued)

*Primary Examiner* — Brian J Gangle
(74) *Attorney, Agent, or Firm* — Alchemy-Partners, PC

(57) ABSTRACT

Techniques from two basic approaches, structure-based immunogen design and phage T4 nanoparticle delivery, are developed to construct new plague vaccines. The $NH_2$-terminal β-strand of F1 of *Yersinia pestis* is transplanted to the COOH-terminus of F1 of *Yersinia pestis* and the $NH_2$-terminus sequence flanking the β-strand of F1 of *Yersinia pestis* is duplicated to eliminate polymerization but to retain the T cell epitopes. The mutated F1 is fused to the V antigen of *Yersinia pestis* to thereby form a fusion protein F1mut-V mutant, which produces a completely soluble monomer. The fusion protein F1mut-V is then arrayed on phage T4 nanoparticles via a small outer capsid protein, Soc, from a T4 phage or a T4-related phage. Both the soluble and T4 decorated F1mut-V provided approximately 100% protection to mice and rats against pneumonic plague evoked by high doses of *Yersinia pestis* CO92.

18 Claims, 11 Drawing Sheets

(56) References Cited

OTHER PUBLICATIONS

Mizel SB, Graff AH, Sriranganathan N, Ervin S, Lees CJ, et al. (2009) Flagellin-F1-V fusion protein is an effective plague vaccine in mice and two species of nonhuman primates. Clin Vaccine Immunol 16: 21-28.
Goodin JL, Nellis DF, Powell BS, Vyas VV, Enama JT, et al. (2007) Purification and protective efficacy of monomeric and modified Yersinia pestis capsular F1-V antigen fusion proteins for vaccination against plague. Protein Expr Purif 53: 63-79.
Goodin JL, Powell BS, Enama JT, Raab RW, McKown RL, et al. (2011) Purification and characterization of a recombinant Yersinia pestis V-F1 "Reversed" fusion protein for use as a new subunit vaccine against plague. Protein Expr Purif 76: 136-144.
Powell BS, Andrews GP, Enama JT, Jendrek S, Bolt C, et al. (2005) Design and testing for a nontagged F1-V fusion protein as vaccine antigen against bubonic and pneumonic plague. Biotechnol Prog 21: 1490-1510.
Parent MA, Berggren KN, Kummer LW, Wilhelm LB, Szaba FM, et al. (2005) Cell-mediated protection against pulmonary Yersinia pestis infection. Infect Immun 73: 7304-7310.
Friedlander AM, Welkos SL, Worsham PL, Andrews GP, Heath DG, et al. (1995) Relationship between virulence and immunity as revealed in recent studies of the F1 capsule of Yersinia pestis. Clin Infect Dis 21 Suppl 2: S178-181.
Roggenkamp A, Geiger AM, Leitritz L, Kessler A, Heesemann J (1997) Passive immunity to infection with *Yersinia* spp. mediated by anti-recombinant V antigen is dependent on polymorphism of V antigen. Infect Immun 65: 446-451.
Erova TE, Rosenzweig JA, Sha J, Suarez G, Sierra JC, et al. (2013) Evaluation of protective potential of Yersinia pestis outer membrane protein antigens as possible candidates for a new generation recombinant plague vaccine. Clin Vaccine Immunol 20: 227-238.
DeBord KL, Anderson DM, Marketon MM, Overheim KA, DePaolo RW, et al. (2006) Immunogenicity and protective immunity against bubonic plague and pneumonic plague by immunization of mice with the recombinant V10 antigen, a variant of LcrV. Infect Immun 74: 4910-4914.
Li Q, Shivachandra SB, Leppla SH, Rao VB (2006) Bacteriophage T4 capsid: a unique platform for efficient surface assembly of macromolecular complexes. J Mol Biol 363: 577-588.
Li Q, Shivachandra SB, Zhang Z, Rao VB (2007) Assembly of the small outer capsid protein, Soc, on bacteriophage T4: a novel system for high density display of multiple large anthrax toxins and foreign proteins on phage capsid. J Mol Biol 370: 1006-1019.
Shivachandra SB, Li Q, Peachman KK, Matyas GR, Leppla SH, et al. (2007) Multicomponent anthrax toxin display and delivery using bacteriophage T4. Vaccine 25: 1225-1235.
Sathaliyawala T, Rao M, Maclean DM, Birx DL, Alving CR, et al. (2006) Assembly of human immunodeficiency virus (HIV) antigens on bacteriophage T4: a novel in vitro approach to construct multicomponent HIV vaccines. J Virol 80: 7688-7698.
Black LW, Rao VB (2012) Structure, assembly, and DNA packaging of the bacteriophage T4 head. Adv Virus Res 82: 119-153.
Qin L, Fokine A, O'Donnell E, Rao VB, Rossmann MG (2009) Structure of the small outer capsid protein, Soc: a clamp for stabilizing capsids of T4-like phages. J Mol Biol 395: 728-741.
Fokine A, Islam MZ, Zhang Z, Bowman VD, Rao VB, et al. (2011) Structure of the three N-terminal immunoglobulin domains of the highly immunogenic outer capsid protein from a T4-like bacteriophage. J Virol 85: 8141-8148.
Sathaliyawala T, Islam MZ, Li Q, Fokine A, Rossmann MG, et al. (2010) Functional analysis of the highly antigenic outer capsid protein, Hoc, a virus decoration protein from T4-like bacteriophages. Mol Microbiol 77: 444-455.
Ishii T, Yanagida M (1977) The two dispensable structural proteins (soc and hoc) of the T4 phage capsid; their purification and properties, isolation and characterization of the defective mutants, and their binding with the defective heads in vitro. J Mol Biol 109: 487-514.

Andrews GP, Heath DG, Anderson GW, Jr., Welkos SL, Friedlander AM (1996) Fraction 1 capsular antigen (F1) purification from Yersinia pestis CO92 and from an *Escherichia coli* recombinant strain and efficacy against lethal plague challenge. Infect Immun 64: 2180-2187.
Miller J, Williamson ED, Lakey JH, Pearce MJ, Jones SM, et al. (1998) Macromolecular organisation of recombinant Yersinia pestis F1 antigen and the effect of structure on immunogenicity. FEMS Immunol Med Microbiol 21: 213-221.
Musson JA, Morton M, Walker N, Harper HM, McNeill HV, et al. (2006) Sequential proteolytic processing of the capsular Caf1 antigen of Yersinia pestis for major histocompatibility complex class II-restricted presentation to T lymphocytes. J Biol Chem 281: 26129-26135.
Overheim KA, Depaolo RW, Debord KL, Morrin EM, Anderson DM, et al. (2005) LcrV plague vaccine with altered immunomodulatory properties. Infect Immun 73: 5152-5159.
Matson JS, Durick KA, Bradley DS, Nilles ML (2005) Immunization of mice with YscF provides protection from Yersinia pestis infections. BMC Microbiol 5: 38.
Davis AJ, Mecsas J (2007) Mutations in the Yersinia pseudotuberculosis type III secretion system needle protein, YscF, that specifically abrogate effector translocation into host cells. J Bacteriol 189: 83-97.
Quenee LE, Schneewind O (2009) Plague vaccines and the molecular basis of immunity against Yersinia pestis. Hum Vaccin 5: 817-823.
Smiley ST (2008) Immune defense against pneumonic plague. Immunol Rev 225: 256-271.
Do Y, Park CG, Kang YS, Park SH, Lynch RM, et al. (2008) Broad T cell immunity to the LcrV virulence protein is induced by targeted delivery to DEC-205/CD205-positive mouse dendritic cells. Eur J Immunol 38: 20-29.
Agar SL, Sha J, Foltz SM, Erova TE, Walberg KG, et al. (2009) Characterization of the rat pneumonic plague model: infection kinetics following aerosolization of Yersinia pestis CO92. Microbes Infect 11: 205-214.
Chalton DA, Musson JA, Flick-Smith H, Walker N, McGregor A, et al. (2006) Immunogenicity of a Yersinia pestis vaccine antigen monomerized by circular permutation. Infect Immun 74: 6624-6631.
Sing A, Rost D, Tvardovskaia N, Roggenkamp A, Wiedemann A, et al. (2002) Yersinia V-antigen exploits toll-like receptor 2 and CD14 for interleukin 10-mediated immunosuppression. J Exp Med 196: 1017-1024.
Sodhi A, Sharma RK, Batra HV (2005) Yersinia rLcrV and rYopB inhibits the activation of murine peritoneal macrophages in vitro. Immunol Lett 99: 146-152.
Lin JS, Park S, Adamovicz JJ, Hill J, Bliska JB, et al. (2010) TNFalpha and IFNgamma contribute to F1/LcrV-targeted immune defense in mouse models of fully virulent pneumonic plague. Vaccine 29: 357-362.
Kopp E, Medzhitov R (2002) A plague on host defense. J Exp Med 196: 1009-1012.
Wang S, Goguen JD, Li F, Lu S (2011) Involvement of CD8+ T cell-mediated immune responses in LcrV DNA vaccine induced protection against lethal Yersinia pestis challenge. Vaccine 29: 6802-6809.
Philipovskiy AV, Smiley ST (2007) Vaccination with live Yersinia pestis primes CD4 and CD8 T cells that synergistically protect against lethal pulmonary Y. pestis infection. Infect Immun 75: 878-885.
Amemiya K, Meyers JL, Rogers TE, Fast RL, Bassett AD, et al. (2009) CpG oligodeoxynucleotides augment the murine immune response to the Yersinia pestis F1-V vaccine in bubonic and pneumonic models of plague. Vaccine 27: 2220-2229.
Hickey AJ, Lin JS, Kummer LW, Szaba FM, Duso DK, et al. (2013) Intranasal prophylaxis with CpG oligodeoxynucleotide can protect against Yersinia pestis infection. Infect Immun 81 (6): 2123-2132.
Peachman KK, Li Q, Matyas GR, Shivachandra SB, Lovchik J, et al. (2012) Anthrax vaccine antigen-adjuvant formulations completely protect New Zealand white rabbits against challenge with Bacillus anthracis Ames strain spores. Clin Vaccine Immunol 19: 11-16.

(56) References Cited

OTHER PUBLICATIONS

58. Rao M, Peachman KK, Li Q, Matyas GR, Shivachandra SB, et al. (2011) Highly effective generic adjuvant systems for orphan or poverty-related vaccines. Vaccine 29: 873-877.
Bruttin A, Brussow H (2005) Human volunteers receiving *Escherichia coli* phage T4 orally: a safety test of phage therapy. Antimicrob Agents Chemother 49: 2874-2878.
Tao P, Mahalingam M, Marasa BS, Zhang Z, Chopra AK, et al. (2013) In vitro and in vivo delivery of genes and proteins using the bacteriophage T4 DNA packaging machine. Proc Natl Acad Sci U S A 110: 5846-5851.
Horton RM, Hunt HD, Ho SN, Pullen JK, Pease LR (1989) Engineering hybrid genes without the use of restriction enzymes: gene splicing by overlap extension. Gene 77: 61-68.
Pettersen EF, Goddard TD, Huang CC, Couch GS, Greenblatt DM, et al. (2004) UCSF Chimera—a visualization system for exploratory research and analysis. J Comput Chem 25: 1605-1612.
Hu X, Zhou W, Udaka K, Mamitsuka H, Zhu S (2010) MetaMHC: a meta approach to predict peptides binding to MHC molecules. Nucleic Acids Res 38: W474-479.
Brito LA, Singh M (2011) Acceptable levels of endotoxin in vaccine formulations during preclinical research. J Pharm Sci 100: 34-37.
Agar SL, Sha J, Foltz SM, Erova TE, Walberg KG, et al. (2008) Characterization of a mouse model of plague after aerosolization of Yersinia pestis CO92. Microbiology 154: 1939-1948.
Santi et al., "Protection conferred by recombinant Yersinia pestis antigens produced by a rapid and highly scalable plant expression system", PNAS, vol. 103, No. 4, pp. 861-866 (2006).
Tao et al., "Mutated and Bacteriophage T4 Nanoparticle Arrayed F1-V Immunogens from Yersinia pestis as Next Generation Plague Vaccines", PLOS Pathogens, vol. 9, Issue No. 7, Article No. 1003495, pp. 1-16 (2013).
Notification of Transmittal of the International Search Report and the Written Opinion, International Search Report and Written Opinion received in PCT Application No. PCT/IB2014/063005 mailed Oct. 23, 2014.

MUTATED AND BACTERIOPHAGE T4 NANOPARTICLE ARRAYED F1-V IMMUNOGENS FROM *YERSINIA PESTIS* AS NEXT GENERATION PLAGUE VACCINES

CROSS-REFERENCE TO RELATED APPLICATIONS

This application claims benefit of priority to U.S. Provisional Patent Application No. 61/845,487 to Rao and Tao, entitled "Mutated and Bacteriophage T4 Nanoparticle Arrayed F1-V Immunogens from *Yersinia Pestis* as Next Generation Plague Vaccines," filed Jul. 12, 2013. The entire contents and disclosures of the patent application are incorporated herein by reference in its entirety.

GOVERNMENT INTEREST STATEMENT

United States Government has rights in this invention pursuant to Contract No. NIAID U01-AI082086, NIAID AI064389 (in part), and NO1-A1-30065 awarded by National Institutes of Health; and T32 predoctoral training grant on Biodefense AI060549.

This application makes reference to the following U.S. patents and U.S. patent applications: U.S. Provisional Patent Application No. 61/774,895, filed Mar. 8, 2013, entitled "In Vitro and In Vivo Delivery of Genes and Proteins Using the Bacteriophage T4 DNA Packaging Machine"; U.S. Provisional Patent Application No. 60/904,168, filed Mar. 1, 2007, entitled "Liposome-Bacteriophage Complex as Vaccine Adjuvant"; U.S. patent application Ser. No. 12/039,803, filed Feb. 29, 2008, entitled "Liposome-Bacteriophage Complex as Vaccine Adjuvant", now U.S. Pat. No. 8,148,130, issued Apr. 3, 2012; U.S. patent application Ser. No. 11/015,294, filed Dec. 17, 2004, entitled "Methods and Compositions Comprising Bacteriophage Nanoparticles"; U.S. Provisional Patent Application No. 60/530,527, filed Dec. 17, 2003, entitled "Methods and Compositions Comprising Bacteriophage Nanoparticles"; U.S. Provisional Patent Application No. 61/322,334, filed Apr. 9, 2010, entitled "Promiscuous DNA Packaging Machine From Bacteriophage T4"; U.S. patent application Ser. No. 13/082,466, filed Apr. 8, 2011, entitled "Protein and Nucleic Acid Delivery Vehicles, Components and Mechanisms Thereof"; U.S. Provisional Patent Application No. 61/731,147, filed Nov. 29, 2012, entitled "Designing a Soluble Full-Length HIV-1 GP41 Trimer"; and U.S. Provisional Patent Application No. 61/845,487 to Rao and Tao, entitled "Mutated and Bacteriophage T4 Nanoparticle Arrayed F1-V Immunogens from *Yersinia Pestis* as Next Generation Plague Vaccines," filed Jul. 12, 2013. The entire disclosure and contents of these patent applications are incorporated herein by reference.

BACKGROUND

1. Field of the Invention

The present invention relates generally to mutated immunogens from *Yersinia pestis* and antigen carriers.

2. Related Art

Pneumonic plague is a highly virulent infectious disease with approximately one hundred percent mortality rate, and its causative organism *Yersinia pestis* poses a serious threat for deliberate use as a bioterror agent. Stockpiling of an efficacious plague vaccine that could protect people against a potential bioterror attack has been a national priority. Currently, there is no FDA approved vaccine against plague. There exists a growing need to develop efficacious and easily manufacturable plague vaccines.

SUMMARY

According to a first broad aspect, the present invention provides a recombinant protein comprising a mutated F1 antigen of *Yersinia pestis*, wherein the mutated F1 antigen of *Yersinia pestis* is developed from a native F1 antigen of *Yersinia pestis* by the following steps: deleting an $NH_2$-terminal β-strand of F1 antigen of *Yersinia pestis* from an $NH_2$-terminus of the native F1 antigen of *Yersinia pestis* to thereby form an $NH_2$-terminal β-strand deleted F1, fusing the $NH_2$-terminal β-strand of F1 antigen of *Yersinia pestis* to a COOH-terminus of the $NH_2$-terminal β-strand deleted F1 via a first peptide linker to thereby form an NH2-terminal β-strand transplanted F1, and duplicating an $NH_2$-terminal amino acid sequence of F1 antigen of *Yersinia pestis* flanking the $NH_2$-terminal strand of F1 antigen of *Yersinia pestis* at a COOH-terminus of the NH2-terminal β-strand transplanted F1 to thereby form a mutated F1 antigen of *Yersinia pestis*.

According to a second broad aspect, the present invention provides a fusion protein comprising a small outer capsid protein from a T4 phage and/or a T4-related bacteriophage RB69 fused through a peptide linker to a heterologous polypeptide derived from one or more antigens of *Yersinia pestis* to thereby form a phage capsid protein fusion protein.

According to a third broad aspect, the present invention provides a method for developing a recombinant protein comprising the steps that include: deleting an $NH_2$-terminal β-strand of F1 antigen of *Yersinia pestis* from an $NH_2$-terminus of a native F1 antigen of *Yersinia pestis* to thereby form an $NH_2$-terminal β-strand deleted F1, fusing the $NH_2$-terminal β-strand of F1 antigen of *Yersinia pestis* to a COOH-terminus of the $NH_2$-terminal β-strand deleted F1 via a first peptide linker to thereby form an NH2-terminal β-strand transplanted F1, and duplicating an $NH_2$-terminal amino acid sequence of F1 antigen of *Yersinia pestis* flanking the $NH_2$-terminal β-strand of F1 antigen of *Yersinia pestis* at a COOH-terminus of the NH2-terminal β-strand transplanted F1 to thereby form a mutated F1 antigen of *Yersinia pestis*.

According to a fourth broad aspect, the present invention provides a vaccine comprising one or more phage T4 nanoparticles and one or more immunogens bound to the one or more phage T4 nanoparticles, wherein each of the one or more immunogens comprises a fusion protein comprising a small outer capsid protein from a T4 phage and/or a T4-related bacteriophage RB69 and a heterologous polypeptide derived from one or more antigens of *Yersinia pestis*, wherein the small outer capsid protein from a T4 phage and/or a T4-related bacteriophage RB69 is fused through a peptide linker to a the heterologous polypeptide derived from one or more antigens of *Yersinia pestis*, and wherein each of the one or more immunogens is bound to a phage T4 nanoparticle of the one or more phage T4 nanoparticles via the small outer capsid protein of a phage T4 and/or a T4-related bacteriophage RB69.

According to a fifth broad aspect, the present invention provides a method for producing a vaccine comprising the following steps: incubating one or more phage T4 nanoparticles in a buffered solution with one or more immunogens to thereby form immunogen-bound T4 nanoparticles, sedimenting the immunogen-bound T4 nanoparticles to thereby form a phage pellet and a supernatant, separating the phage pellet from the supernatant to thereby form a separated phage pellet, washing the separated phage pellet one or more times to thereby form a washed phage pellet, and suspending the washed phage pellet in a buffered solution to thereby form a vaccine solution. In the vaccine, the one or more immunogens comprise one or more phage capsid protein fusion proteins, and each of one or more phage capsid protein fusion proteins comprises a small outer capsid protein from a phage T4 and/or a T4-related bacteriophage RB69 fused through a peptide linker to a heterologous polypeptide derived from one or more antigens of *Yersinia pestis*. In the vaccine, each of the one or more immunogens is bound to a phage T4 nanoparticle of the one or more phage T4 nanoparticles via the small outer capsid protein from a phage T4 and/or a T4-related bacteriophage RB69.

According to a sixth broad aspect, the present invention provides a method of immunization comprising a step of administering to a subject an immunogenic amount of a vaccine comprising a purified mutated F1 antigen of *Yersinia pestis*.

According to a seventh broad aspect, the present invention provides a method of immunization comprising administering to a subject an immunogenic amount of a vaccine that comprises one or more phage T4 nanoparticles and one or more immunogens bound to the one or more phage T4 nanoparticles, wherein each of the one or more immunogens comprises a fusion protein comprising a small outer capsid protein from a T4 phage and/or a T4-related bacteriophage RB69 and a heterologous polypeptide derived from one or more antigens of *Yersinia pestis*, wherein the small outer capsid protein from a T4 phage and/or a T4-related bacteriophage RB69 is fused through a peptide linker to the heterologous polypeptide derived from one or more antigens of *Yersinia pestis*, and wherein each of the one or more immunogens is bound to a phage T4 nanoparticle of the one or more phage T4 nanoparticles via the small outer capsid protein of a phage T4 and/or a T4-related bacteriophage RB69.

According to an eighth broad aspect, the present invention provides a method comprising following steps: culturing compatible host cells having expression vectors therein to thereby form a cell culture comprising expressed products, and purifying the expressed products from the cell culture to thereby form one or more immunogens, wherein the one or more immunogens encompassing one or more recombinant proteins as in any one of claims 1-10.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Definitions

Figure 1:
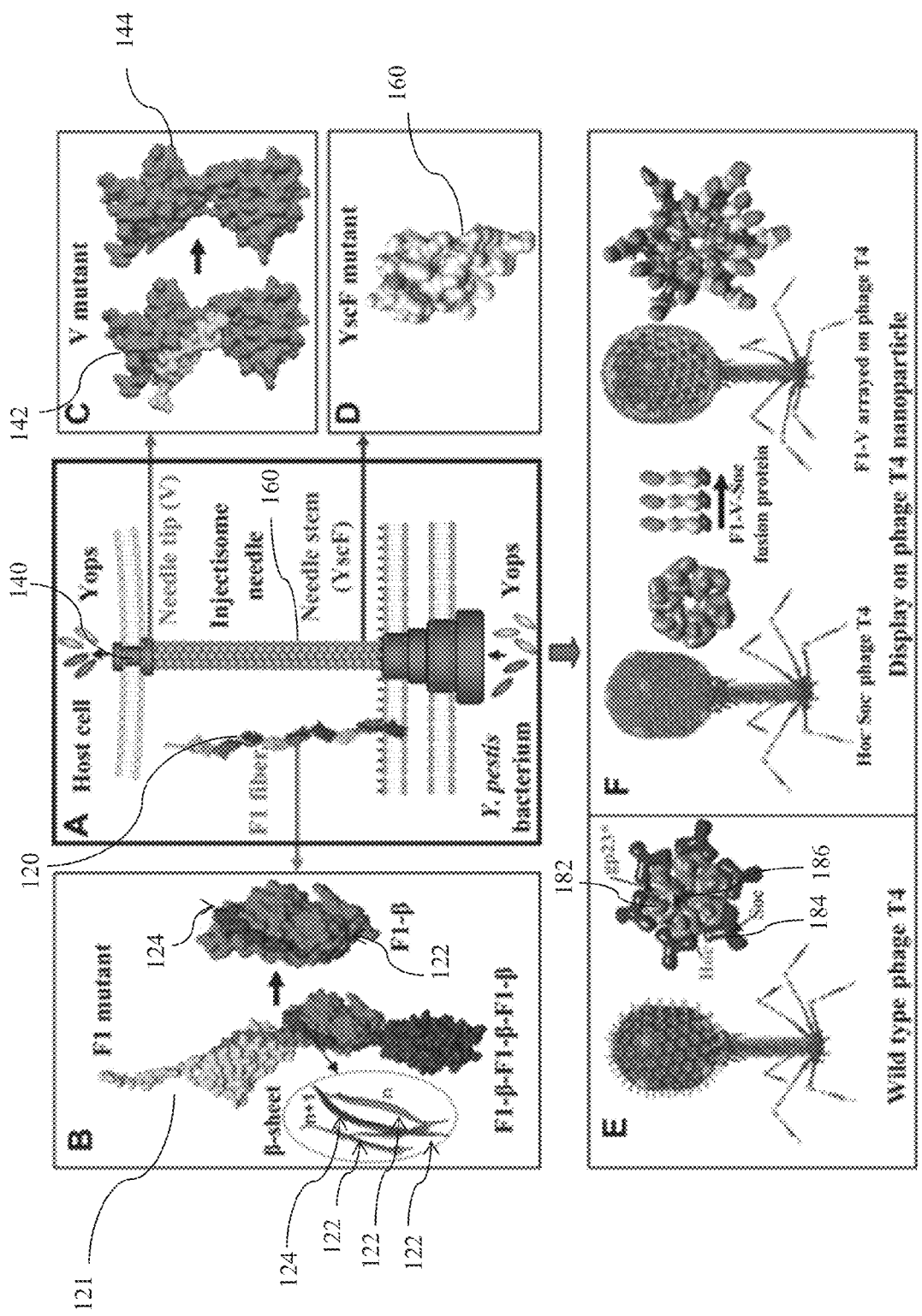
FIG. 1 is a set of schematics of various approaches used to design plague immunogens. Panel A shows *Y. pestis* surface components, an F1 antigen 120, a V antigen 140, and a YscF 160, that are targeted for vaccine design in some embodiments of the present invention. Panel B is a stereo diagram of X-ray crystal structures of an F1 mutant 121 in one embodiment of the present invention. Panel C shows a putative immunomodulatory sequence (aa residues 271-300) of a V antigen 142 is deleted and thereby form a V antigen mutant 144. Panel D of FIG. 1 shows that a YscF mutant antigen 160 is constructed through changing an amino acid residue Asn35 to Ser and an amino acid residue Ile 67 to Thr to thereby produce an oligomerization deficient mutant YscF35/67 antigen. Panel E is a structural model of a bacteriophage T4. Panel F shows display of an F1mut-V-Soc fusion protein on a Hoc⁻ Soc⁻ bacteriophage particle via Soc from a phage T4 or a T4-related bacteriophage.

Where the definition of terms departs from the commonly used meaning of the term, applicant intends to utilize the definitions provided below, unless specifically indicated.

For purposes of the present invention, it should be noted that the singular forms, "a," "an" and "the" include reference to the plural unless the context as herein presented clearly indicates otherwise.

For purpose of the present invention, the term "adjacent" refers to "next to" or "adjoining something else."

For purpose of the present invention, the term "adjuvant" refers the components in a vaccine or therapeutic composition that increase the specific immune response to the antigen. Adjuvants are well known to those of skill in the art and may include cytokines (e.g., IFN-γ, IL-2, and IL-12) which contribute to the induction of cell-mediated immune response to an administered antigen, as well as induction of humoral immune responses. Traditional vaccine usually needs an adjuvant.

For purpose of the present invention, the phase "administration of a vaccine" refers to introduce a vaccine into a body of an animal or a human being. As is understood by an ordinary skilled person, it can be done in a variety of manners. For example, administration of a vaccine may be done intramuscularly, subcutaneously, intravenously, intranasally, intradermaly, intrabursally, in ovo, ocularly, orally, intra-tracheally or intra-bronchially, as well as combinations of such modalities. The dose of the vaccine may vary with the size of the intended vaccination subject.

For purpose of the present invention, the term "array" refers to in vitro binding of a protein on T4 phage. For example, a Soc fusion protein, a protein fused with a small outer capsid protein Soc of a T4 phage, may be arrayed by incubating Hoc⁻Soc⁻ T4 phage particles with the Soc fusion protein to allow the Soc fusion protein to bind on Hoc⁻Soc⁻ T4 phage particles.

For purposes of the present invention, the term "bind," the term "binding" or the term "bound" refers to any type of chemical or physical binding, which includes but is not limited to covalent binding, hydrogen binding, electrostatic binding, biological tethers, transmembrane attachment, cell surface attachment and expression.

For purpose of the present invention, the term "bivalent" refers to a composition that has two combining sites, for example, a bivalent immunogen capable of binding to two molecules of antibodies.

For purpose of the present invention, the term "β-sheet" (also "beta sheet") refers to a secondary form of regular secondary structure in proteins. It consists of "β-strands" (also "beta strand") connected laterally by at least two or three backbone hydrogen bonds, forming a generally twisted, pleated sheet.

For purpose of the present invention, the term "β-strand" (also "beta strand") refers to a stretch of polypeptide chain. It is typically 3 to 10 amino acids long with backbone in an almost fully extended conformation.

For purposes of the present invention, the term "capsid" and the term "capsid shell" refers to a protein shell of a virus comprising several structural subunits of proteins. The capsid encloses the nucleic acids of the virus. Capsids are broadly classified according to their structures. The majority of viruses have capsids with either helical or icosahedral structures.

For purpose of the present invention, the term "capsomere" refers to a basic substructure of a capsid, an outer covering of proteins that protects the genetic materials of a virus. Capsomeres self-assemble to form the capsid.

For purpose of the present invention, the term "cleft" refers to a groove or a V-shaped indentation that runs across two protein domains.

The term "comprising", the term "having", and the term "including" are intended to be open-ended and mean that there may be additional elements other than the listed elements.

For purpose of the present invention, the term "correspond" and the term "corresponding" refer to that a protein sequence refer interchangeably to an amino acid position(s) of a protein. An amino acid at a position of a protein may be found to be equivalent or corresponding to an amino acid at a position of one or more other protein(s) based on any relevant evidence, such as the primary sequence context of the each amino acid, its position in relation to the N-terminal and C-terminal ends of its respective protein, the structural and functional roles of each amino acid in its respective protein, etc.

For purpose of the present invention, the term "duplicate" refers to repeat or generate another identical copy of a polynucleotide sequence or an amino acid sequence.

For purpose of the present invention, the term "epitope" refers to a molecular region on the surface of an antigen capable of eliciting an immune response and combining with the specific antibody produced by such a response. It is also called "antigenic determinant." T cell epitopes are presented on the surface of an antigen-presenting cell, where they are bound to MHC molecules.

For purpose of the present invention, the term "flank" refers to be situated on a side of a polynucleotide sequence or an amino acid sequence.

For purpose of the present invention, the term "fragment" of a molecule such as a protein or nucleic acid refers to a portion of the amino acid or nucleotide sequence.

For purpose of the present invention, the term "fuse" refers to join together physically, or to make things join together and become a single thing.

For purpose of the present invention, the term "fusion polypeptide" or the term "fusion protein" refers to a polypeptide or a protein created through the joining of two or more genes that originally coded for separate proteins. Translation of this fusion gene results in a single or multiple polypeptides with functional properties derived from each of the original proteins. Usually, a fusion protein has at least two heterologous polypeptides covalently linked, either directly or via an amino acid linker. The heterologous polypeptides forming a fusion protein are typically linked C-terminus to N-terminus, although they can also be linked C-terminus to C-terminus, N-terminus to N-terminus, or N-terminus to C-terminus. The polypeptides of the fusion protein can be in any order and may include more than one of either or both of the constituent polypeptides. These terms encompass conservatively modified variants, polymorphic variants, alleles, mutants, subsequences, interspecies homologs, and immunogenic fragments of the antigens that make up the fusion protein. Fusion proteins of the disclosure may also comprise additional copies of a component antigen or immunogenic fragment thereof. Recombinant fusion proteins are created artificially by recombinant DNA technology for use in biological research or therapeutics.

For purpose of the present invention, the term "identical" or the term "identity" refers to the percentage of amino acid residues of two or more polypeptide sequences having the same amino acid at corresponding positions.

For purposes of the present invention, the term "immune response" refers to an action by the immune system. The immune system is a system of biological structure and processes within an organism that protects against an invasion of a foreign object. The immune system can be classified into subsystems, such as the innate immune system versus the adaptive immune system, or the humoral immunity versus the cellular immunity. In humoral immunity, responses to foreign objects which include bacteria or viruses involve producing antibodies. In cellular immunity, also called "cell-mediated immunity," responses to foreign objects including bacteria or viruses involve the activation of phagocytes, antigen-specific cytotoxic T-lymphocytes, and the release of various cytokines. Cellular immunity is effective in removing virus-infected cells, but also participates in defending against fungi, protozoans, cancers, and intracellular bacteria. Cellular immunity also plays a major role in transplant rejection.

For purposes of the present invention, the term "immunization dose" refers to the amount of antigen or immunogen needed to precipitate an immune response. This amount will vary with the presence and effectiveness of various adjuvants. This amount will vary with the animal and the antigen, immunogen and/or adjuvant. The immunization dose is easily determined by methods well known to those skilled in the art, such as by conducting statistically valid host animal immunization and challenge studies.

For purposes of the present invention, the term "immunogen" and the term "immunogenic" refer to a substance or material (including antigens) that is able to induce an immune response alone or in conjunction with an adjuvant. Both natural and synthetic substances may be immunogens. An immunogen is generally a protein, peptide, polysaccharide, nucleoprotein, lipoprotein, synthetic polypeptide, or hapten linked to a protein, peptide, polysaccharide, nucleoprotein, lipoprotein or synthetic polypeptide or other bacterial, viral or protozoal fractions.

For purpose of the present invention, the term "linked" refers to a covalent linkage between two polypeptides in a fusion protein. The polypeptides are typically joined via a peptide bond, either directly to each other or via one or more additional amino acids.

For purpose of the present invention, the term "linker" refers to short peptide sequences that occur between functional protein domains and link the functional domains together. Linkers designed by researchers are generally classified into three categories according to their structures: flexible linkers, rigid linkers, and in vivo cleavable linkers. A flexible linker is often composed of flexible residues like glycine and serine so that the adjacent protein domains are free to move relative to one another. A linker also may play a role in releasing the free functional domain in vivo (as in in vivo cleavable linkers). Linkers may offer many other advantages for the production of fusion proteins, such as improving biological activity, increasing expression yield, and achieving desirable pharmacokinetic profiles. The composition and length of a linker may be determined in accordance with methods well known in the art and may be tested for efficacy. A linker is generally from about 3 to about 15 amino acids long, in some embodiments about 5 to about 10 amino acids long, however, longer or shorter linkers may be used or the linker may be dispensed with entirely. A glycine linker is one that contains one or more glycines but no other amino acid residues, e.g., GlyGlyGlyGly (SEQ ID NO: 3). A glycine-rich linker is one that contains one or more glycines and may contain one or more other amino acid residues as long as glycine is the predominant species in the linker, e.g., GlyGlyGlyAsnGlyGly (SEQ ID NO: 4). A GlySer linker is one which contains both glycine and serine in any proportion, e.g. GlyGlyGlySer (SEQ ID NO: 5).

For purpose of the present invention, the term "monomer" refers to a molecule that may bind chemically to other molecules to form a polymer. The term "monomeric protein" may also be used to describe one of the proteins making up a multiprotein complex.

For purpose of the present invention, the term "mutant protein" refers to a protein product encoded by a gene with mutation.

For purpose of the present invention, the term "oligomer" refers to a molecular complex that consists of a few monomer units. Dimers, trimers, and tetramers are, for instance, oligomers respectively composed of two, three and four monomers. An oligomer can be a macromolecular complex formed by non-covalent bonding of few macromolecules like proteins or nucleic acids. In this sense, a homo-oligomer would be formed by few identical molecules and by contrast, a hetero-oligomer would be made of three different macromolecules.

For purpose of the present invention, the term "oligomerization" refers to a chemical process that converts monomers to macromolecular complexes through a finite degree of polymerization.

For purpose of the present invention, the term "polymer" refers to a compound or a mixture of compounds comprising many repeating subunits, known as monomers.

For purpose of the present invention, the term "polypeptide" and the term "protein" are used interchangeably herein to refer to a polymer of amino acid residues. The terms encompass amino acid polymers in which one or more amino acid residues are artificial chemical mimetic of a corresponding naturally occurring amino acids, as well as to naturally occurring amino acid polymers and non-naturally occurring amino acid polymer.

For purpose of the present invention, the term "protein domain" refers to a distinct functional or structural unit in a protein. Usually, a protein domain is responsible for a particular function or interaction, contributing to the overall role of a protein. Domains may exist in a variety of biological contexts, where similar domains can be found in proteins with different functions.

For purposes of the present invention, the term "purified" refers to the component in a relatively pure state, e.g. at least about 90% pure, or at least about 95% pure, or at least about 98% pure.

For purpose of the present invention, the term "recombinant protein" refers to a protein derived from a recombinant DNA, that is, it's code was carried by a "recombinant DNA" molecule. Recombinant DNA molecules are DNA molecules formed by laboratory methods of genetic recombination (such as molecular cloning) to bring together genetic material from multiple sources, creating sequences that would not otherwise be found in biological organisms.

For purpose of the present invention, the term "recombinant vaccine" refers to a vaccine made by genetic engineering, the process and method of manipulating the genetic material of an organism. Usually, a recombinant vaccine encompasses one or more protein antigens that have either been produced and purified in a heterologous expression system (e.g., bacteria or yeast) or purified from large amounts of the pathogenic organism. The vaccinated person produces antibodies to the one or more protein antigens, thus protecting him/her from disease.

For purpose of the present invention, the term "subunit" refers to a separate polypeptide chain that makes a certain protein which is made up of two or more polypeptide chains joined together. In a protein molecule composed of more than one subunit, each subunit can form a stable folded structure by itself. The amino acid sequences of subunits of a protein can be identical, similar, or completely different.

For purpose of the present invention, the term "subject" or the term "individual" refers interchangeably to a mammalian organism, such as a human, mouse, etc., that is administered a mutant protein of the present invention for a therapeutic or experimental purpose.

For purpose of the present invention, the term "suitable vector" refers to any vector (for example, a plasmid or virus) which may incorporate a nucleic acid sequence encoding an antigenic polypeptide and any desired control sequences. It may bring about the expression of the nucleic acid sequence. The choice of the vector will typically depend on the compatibility of the vector with a host cell into which the vector is to be introduced.

For purpose of the present invention, the term "type three secretion system (T3SS)" refers to a protein appendage found in *Yersinia*, a genus of Gram-negative rod shaped bacteria that cause the plague. T3SS is also called "injectisome" or "injectosome," with a needle-like structure used as a sensory probe to detect the presence of eukaryotic organisms and secrete proteins that help the bacteria infect them. T3SS are essential for the pathogenicity of many pathogenic bacteria.

For purpose of the present invention, the term "vaccine" refers to a biological compound that improves immunity to a particular disease. A vaccine typically contains an agent that resembles a disease-causing microorganism (microbe), such as virus, bacteria, fungus, etc. Traditionally, it is often made from weakened or killed forms of the microbe, its toxins, or one of its surface proteins. The agent injected into a human or animal body stimulates the body's immune system to recognize the agent as foreign, destroy it, and keep a record of it, so that the immune system can more easily recognize and destroy any of these microorganisms that it later encounters.

For purpose of the present invention, the term "transplant" refers to move or transfer a fragment of a DNA or a protein to another place or situation. For example, the $NH_2$-terminal amino acid residues of a protein may be "transplanted" to the COOH-terminus of the protein by deleting the $NH_2$-terminal amino acid residues and fusing them to the COOH-terminus of the protein via a short linker wherein the short linker joins the deleted $NH_2$-terminal amino acid residues to the COOH-terminus of the protein.

DESCRIPTION

Plague, also known as Black Death, is one of the deadliest infectious diseases known to mankind. *Yersinia pestis* (*Y. pestis*), the etiologic agent of plague, is a Gram-negative bacterium. It injects effector proteins into mammalian host cells to interfere with the host immune response, thereby enabling the pathogens to thrive. *Y. pestis* is transmitted from rodents to humans via fleas.[1] The bite of an infected flea results in bubonic plague which can then develop into secondary pneumonic plague, resulting in person-to-person transmission of the pathogen through infectious respiratory droplets[2] Pneumonic plague can also be caused by direct inhalation of the aerosolized *Y. pestis*, leading to near approximately 100% death of infected individuals within 3-6 days.[2,3] Due to its exceptional virulence and relative ease of cultivation, aerosolized *Y. pestis* poses one of the greatest threats for deliberate use as a biological weapon.[4] Since the disease spreads rapidly, the window of time available for post-exposure therapeutics is very limited, usually 20-24 hours after the appearance of symptoms.[3] Although levofloxacin, a broad spectrum antibiotic, has recently been approved by the Food and Drug Administration (FDA) for all forms of plague, prophylactic vaccination is one of the most effective means to reduce the risk of plague.

Since the deadly anthrax attacks in 2001, stockpiling of recombinant anthrax and plague vaccines to protect masses against a potential bioterror attack became a national priority. However, no plague vaccine has yet been licensed. The reasons include poor stability, insufficient immunogenicity, or manufacturing difficulties associated with the current formulations of plague vaccines. A killed whole cell (KWC) vaccine was once in use in the United States and a live attenuated plague vaccine (EV76) is still in use in the states of former Soviet Union.[5] However, the need for multiple immunizations, high reactogenicity, and insufficient protection made the KWC vaccine undesirable for mass vaccination, and, consequently, it was discontinued in the United States.[6] In fact, because the highly infectious nature of the plague bacterium and the virulence mechanisms of vaccine strains have not been fully understood, the live-attenuated vaccine may not meet the requirement for the approval of FDA.[6,7] A cautionary tale related to this is a recent fatality of a researcher as a result of exposure to the attenuated pigmentation-minus *Y. pestis* strain, KIM/D2.

The focus in the past two decades, thus, has shifted to the development of recombinant subunit vaccines[3,6,8,9] containing two surface-exposed virulence factors of *Y. pestis*: a capsular protein (Caf1 or F1; 15.6 kDa) and a low calcium response V antigen (LcrV or V; 37.2 kDa) which is a component of a type 3 secretion system (T3SS). Factors F1 and V are known as *Y. pestis* antigens and have been found to be capable of evoking protective immune responses in animals. The effector proteins of *Y. pestis* are translocated through an extracellular, hollow needle structure that forms part of the T3SS. The needle is made up of many copies of a single protein called YscF and is anchored by interactions with a T3SS base, which is embedded in the inner and outer bacterial membranes. F1 antigen assembles into flexible linear fibers via a chaperone/usher mechanism,[10] forming a capsular layer that allows *Y. pestis* to adhere to a host cell and escape phagocytosis.[11] The V antigen forms a "pore" at a tip of an "injectisome" structure of the T3SS needle, creating a channel that delivers a range of virulence factors, also known as the *Yersinia* outer membrane proteins (Yops), into the host cytosol.[12] The V antigen is also critical for impairment of host's phagocytic responses.[13] Abrogation of these functions by F1 and V antibodies appears to be one of the mechanisms leading to protection of the host against lethal *Y. pestis* infection.

The surface-exposed *Y. pestis* F1 and V antigens have been the leading candidates for formulating a recombinant subunit plague vaccine for nearly two decades.[14,15,16,17] Two types of F1/V recombinant vaccines, one containing a mixture of F1 and V antigens[14], and another containing a single F1-V fusion protein, have been under investigation.[15,16] Although poorly immunogenic by themselves, their immunogenicity could be enhanced by adjuvantation with Alum[15] or by fusion with a molecular adjuvant such as flagellin.[19] Although both types of F1/V recombinant vaccines induce protective immunity against *Y. pestis* challenge in rodent and cynomolgus macaque models, the protection of African Green monkeys was insufficient and highly variable.[6,17] A phase I clinical trial in humans showed that a vaccine consisting of a mixture of F1 and V proteins was immunogenic, however, the antibody titers varied over a wide range leading to concerns about the consistency of vaccine efficacy.[18]

One of the problems associated with the current plague vaccines is that the naturally fibrous F1 polymerizes into heterodisperse aggregates, compromising the quality and overall efficacy of the vaccines.[15,19,20,21,22] Second, the subunit vaccines do not induce adequate cell-mediated immune responses, which appear to be essential for optimal protection against plague.[23] Third, it is unclear if inclusion of other *Y. pestis* antigens such as the YscF, the structural unit of the injectisome needle, can boost the potency of the F1/V vaccines. This is particularly important as F1-minus strains of *Y. pestis* exist in nature which are as virulent as the wild-type strains[24,25] and the significant diversity in the LcrV sequence of these F1-minus strains might render the current F1/V vaccines ineffective.[26,27] Finally, the reported immunosuppressive property of V antigen[13,28] and whether it could compromise the innate immunity of humans, are significant concerns. These questions must be addressed to generate a next generation plague vaccine that could pass licensing requirements, as well as be manufactured relatively easily for stockpiling.

New immunogen designs and vaccine platforms that could overcome some of these problems would be of great interest not only to stockpile efficacious biodefense vaccines but also to develop vaccines against a series of infectious diseases of public health importance.

The present inventors have developed a novel vaccine delivery system using the bacteriophage T4 nanoparticles.[29,30,31,32] The capsid (head) of a bacteriophage T4 is an elongated icosahedron, 120 long and 86 nm wide, composed of three essential capsid proteins: a major capsid protein, gp23*; a vertex protein, gp24*; and a portal protein, gp20. It is decorated with two non-essential proteins: Soc, a small outer capsid protein; and Hoc, a highly antigenic outer capsid protein. Binding sites for these capsid proteins appear following head "expansion," a major conformational change that increases the outer dimensions of the capsid by approximately 15% and inner volume by approximately 50%.[33]

Approximately 870 molecules of the tadpole-shaped Soc protein (9 kDa) assemble into trimers at quasi three-fold axes, clamping to adjacent capsomers and forming a reinforced cage around the shell.[34] This stabilizes an already stable head and enables the head to withstand harsh extracellular environment (e.g., pH 10[34]. Hoc, on the other hand, is a linear "fiber" containing a string of four domains, three of which are immunoglobulin (Ig)-like.[35] One hundred and fifty five copies of Hoc fibers, with their $NH_2$-termini projected at approximately 160 Å distance from the capsid, assemble at the center of each capsomer. Hoc binds to bacterial surfaces, apparently enriching the phage near its host for infection.[36] Although Soc and Hoc provide survival advantages to T4 phage, they are completely dispensable under laboratory conditions showing no significant effect on phage productivity or infectivity.[37] Purified Soc (or Hoc) protein binds to Hoc– Soc– capsid of a T4 phage nanoparticle with high specificity and nanomolar affinity, properties that are not compromised by attachment of a pathogen antigen at the $NH_2$— and COOH-termini.[29,30,31,32] Individual domains, full-length proteins as large as approximately 90 kDa, or multilayered oligomeric complexes that are larger than approximately 500 kDa fused to Soc can be arrayed on T4 capsid, making it a robust antigen delivery platform.[29,30]

Disclosed embodiments provide structure-based immunogen design and T4 nanoparticle delivery approaches to engineer new and efficacious plague vaccines that could be manufactured relatively easily and could provide complete protection against pneumonic plague in at least two rodent models.

In some embodiments of the present invention, *Y. pestis* surface components are targeted for vaccine design.

FIG. 1 shows some approaches used to design new plague immunogen. Panel A of FIG. 1 shows *Y. pestis* surface components, an F1 antigen 120, a V antigen 140, and a YscF 160, that are targeted for vaccine design in some embodiments of the present invention. F1 antigen 120 is a structural unit of the capsular layer of *Y. pestis*. V antigen 140 forms a pore at a tip of an injectisome needle and facilitates a translocation of Yops into a host cell. YscF 160 is a structural unit of the injectisome needle.

The X-ray structure and biochemical studies have established that F1 polymerizes into a linear fiber by head to tail interlocking of F1 subunits through a donor strand complementation mechanism.[10] Each F1 subunit has an Ig-like domain consisting of a four-stranded anti-parallel β-sheet. Of the four β-strands, three belong to one subunit forming a cleft into which the $NH_2$-terminal β-strand of the "n+1" subunit locks in, resulting in a bridge connecting adjacent subunits (inter-molecular complementation) (see Panel B of FIG. 1). Stringing of subunits in this fashion leads to assembly of linear F1 fibers of varying lengths. Caf1M chaperone, a single polypeptide subunit, is required for this process because prior to filling the cleft, a "spare" β-strand of Caf1M temporarily occupies the cleft until it is replaced by a β-strand of the incoming subunit with the assistance of an outer membrane usher protein, Caf1A. Over-expression of the F1 gene in a heterologous system such as *E. coli* exposes the unfilled hydrophobic cleft, resulting in uncontrolled aggregation of F1 subunits into insoluble inclusion bodies.

Panel B of FIG. 1 is a stereo diagram of X-ray crystal structures of an F1 mutant 121 in one embodiment of the present invention. It shows that a reorientation of an $NH_2$-terminal β-strand of an F1 antigen 120 generates a monomeric F1 mutant 121. In one embodiment of the present invention, the NH$_2$-terminal β-strand of F1 antigen of *Yersinia pestis* comprises NN$_2$-terminal amino acid residues from 1-14 of an NH$_2$-terminus of a native F1 antigen of *Yersinia pestis*. In one embodiment of the present invention, an NH$_2$-terminus sequence flanking the NH$_2$-terminal β-strand of the F1 antigen of *Y. pestis* is duplicated at a COOH-terminus of the F1 antigen of *Y. pestis* to eliminate polymerization but to retain the T cell epitopes. The resulted mutated F1 antigen of *Y. pestis* retains T cell epitopes but folds into a soluble monomer rather than into an insoluble fiber. "n" and "n+1" refer to the F1 subunits the β-strands belong to, wherein strands in shade 122 refer to "n" subunit and a strand in shade 124 refers to the "n+1" subunit.

In one embodiment of the present invention, the mutated F1 antigen is fused to V antigen to produce a bivalent F1mut-V immunogen that is also expressed as a soluble monomer. In one embodiment of the present invention, the mutated F1 is fused to V antigen via a flexible two amino acid peptide linker Ser-Ala.

Some embodiments of the present invention provide approaches to construct an oligomerization deficient YscF mutant antigen and a V mutant antigen lacking a putative immunomodulatory sequence. Panel C of FIG. 1 shows a putative immunomodulatory sequence (aa residues 271-300) of a V antigen 142 is deleted and thereby form a V antigen mutant 144. Panel D of FIG. 1 shows that a YscF mutant antigen 160 is constructed through changing an amino acid residue Asn35 to Ser and an amino acid residue Ile 67 to Thr to thereby produce an oligomerization deficient mutant YscF35/67 antigen.

In some embodiments of the present invention, thirty COOH-terminal amino acid residues from 270 to 300 of V antigen of *Yersinia pestis* are deleted to thereby form a mutant V10 antigen. The mutant V10 may be fused to the T antigen of *Yersinia pestis* to thereby form a fusion protein F1mut-V10.

In some embodiments, a phage capsid protein fusion protein is constructed by fusing one or more small outer capsid proteins of a phage T4 or a T4-related phage to one or more antigens via one or more linkers. In some embodiments, the one or more small outer capsid proteins of a phage T4 or a T4-related phage encompassing Soc from phage T4 or T4-related bacteriophage RB69.

In some embodiments, a mutant antigen is fused to a Soc protein from a phage T4 or a T4-related phage RB69 via a linker to thereby form a Soc fusion protein. The linker may comprise a two amino acid linker Gly-Ser. In some embodiments, the Soc fusion protein encompasses mutated F1 antigen and V antigen of *Yersinia pestis*. Some embodiments of the present invention disclose that the Soc fusion protein is further fused to a mutant YscF35/67 antigen of *Yersinia pestis* via a linker to thereby form a fusion protein F1-V-Soc-YscF. In some embodiments, the fusion protein F1-V-Soc-YscF may be formed by fusing the mutant YscF35/67 antigen of *Yersinia pestis* to the Soc protein of the Soc fusion protein, and wherein the linker may be a two amino acid linker Gly-Ser.

In other embodiments of the present invention, a native V antigen of *Yersinia pestis* is fused to a Soc protein from a phage T4 and/or a T4-related bactgeriophage RB69 via a linker, which linker may be a two amino acid linker Gly-Ser, wherein a COOH-terminus of the linker is directly linked to an NH$_2$-terminus of the Soc protein from a phage T4 and/or a T4-related bacteriophage RB69 and an NH$_2$-terminus of the linker is directly linked to a COOH-terminus of the V antigen of *Yersinia pestis*.

Disclosed embodiments of the present invention provide that a native F1 antigen of *Yersinia pestis* may be fused to a Soc protein from a phage T4 and/or a T4-related bactgeriophage RB69 via a linker, which linker may be a two amino acid linker Gly-Ser, wherein a COOH-terminus of the linker is directly linked to an NH$_2$-terminus of the Soc protein from phage T4 and/or T4-related bacteriophage RB69 and an NH$_2$-terminus of the linker is directly linked to a COOH-terminus of the F1 antigen of *Yersinia pestis*.

In some embodiments of the present invention, a fusion protein F1mut-V-Soc is fused to a YscF antigen of *Yersinia pestis* via a linker.

In one embodiment of the present invention, the mutated antigens fused to Soc are bound on phage T4 nanoparticles.

Panel E of FIG. 1 is a structural model of a bacteriophage T4. The enlarged capsomer 180 shows a major capsid protein gp23* in shade 182 ("*" represents a cleaved form) (930 copies), Soc in shade 184 (870 copies), and Hoc in shade 186 (155 copies). Subunits of Hoc at the five-fold vertices correspond to gp24*. The portal vertex (not visible in the picture) connects the head to the tail.

Panel F of FIG. 1 shows display of an F1mut-V-Soc fusion protein on a Hoc⁻Soc⁻ bacteriophage particle via Soc from a phage T4 or a T4-related bacteriophage. Enlarged capsomers show models of capsomes before and after F1mut-V display. Upon binding of fusion protein, the T4 phage particle is decorated with the fusion protein.

In one embodiment of the present invention, fusion proteins encompassing mutated F1 and V of *Y. pestis* are expressed in bacteria *E. Coli* cells and purified from cell-free lysates of *E. Coli* cell cultures.

In some embodiments of the present invention, an immunogenic amount of a vaccine comprising a purified mutated F1 antigen of *Yersinia pestis* and an adjuvant is administered to a subject. This vaccine may be administered to a subject via an intramuscular route. In another embodiment of the present invention, an immunogenic amount of a vaccine comprising a purified recombinant protein F1mut-V and an adjuvant is administered to a subject. In one embodiment of the present invention, an immunogenic amount of a vaccine comprising a purified recombinant protein of F1mut-V10 and an adjuvant is administered to a subject.

In some embodiments of the present invention, vaccines encompassing T4-decorated purified recombinant proteins such as F1mut-V-Soc and F1mut-V-Soc-YscF are administered to a subject without any adjuvant. The approaches to administer the vaccines may vary. The vaccines may be administered via an intramuscular route, oral route, or any other appropriate routes.

As shown in some examples of the present application, purified bivalent F1mut-V monomers induces robust immunogenicity. In addition, the T4-decorated fusion protein F1mut-V (fusion protein F1mut-V bound on T4 nanoparticles), without any adjuvant, induced balanced $T_H1$ and $T_H2$ responses. Both the soluble and T4 decorated F1mut-V provide approximately 100% protection to mice and rats against intranasal challenge with high doses of *Y. pestis* CO92. Inclusion of YscF showed a slight enhancement in the potency of F1-V plague vaccine, whereas a replacement of V with V10 mutant, which lacks the putative immunosuppressive sequence, did not significantly alter vaccine efficacy. These results provided new insights into plague vaccine design and produced next generation plague vaccine candidates by overcoming some of the concerns associated with the current subunit vaccines.

The description of the present invention is enhanced by the various examples that follow.

EXAMPLES

Materials and Methods

Ethics Statement

This study was conducted in accordance with the recommendations in the Guide for the Care and Use of Laboratory Animals of the National Institutes of Health. The protocols were reviewed and approved by the Institutional Animal Care and Use Committees of the University of Texas Medical Branch, Galveston, Tex., (Office of Laboratory Animal Welfare assurance number: A3314-01) and The Catholic University of America (Office of Laboratory Animal Welfare assurance number: A4431-01).

DNA, Bacteria, and Bacteriophage

The T7 promoter containing *E. coli* expression vector pET28b is used for recombinant plasmid construction. The template DNAs containing *Y. pestis* F1, V, or YscF are kindly provided by Dr. Richard Borschel from the Walter Reed Army Institute of Research (Silver Spring, Md.). *E. coli* XL-10 Gold cells are used for the initial transformation of clones. The plasmid DNAs are then re-transformed into *E. coli* BL21 (DE3) RIPL for expression of recombinant proteins. The Hoc⁻Soc⁻ phage T4 is propagated on *E. coli* P301 and purified by CsCl gradient centrifugation.

Construction of Plague Recombinant Plasmids

The DNAs encoding F1, V, or YscF are amplified by PCR using primers containing appropriate restriction site(s) (NheI/XhoI for F1 and YscF, and NheI/HindIII for V). The PCR products are purified, digested with appropriate restriction enzymes, and ligated with pET-28b vector DNA digested with the same restriction enzymes. The resulting plasmids had F1, V, or YscF coding sequences fused in-frame with the 23 aa vector sequence containing a hexa-histidine tag at the $NH_2$-terminus. The YscF mutant, YscF35/67, which contained point mutations at aa 35 (Asn to Ser) and 67 (Ile to Thr) is amplified by overlap PCR[61] followed by digestion with NheI and XhoI enzymes. YscF35/67 DNA is then ligated into the linearized pET28b vector. The F1mut1, in which the first 14 aa residues are deleted and fused to the COOH-terminus with a two aa (Ser-Ala) linker, is constructed by two rounds of PCR. The first round of PCR is performed to amplify F1 fragment in which the $NH_2$-terminal 14 aa residues are deleted. This PCR product is used as a template for the second round of PCR using a forward primer containing NheI restriction site and a reverse primer containing the $NH_2$-terminal 14 aa residues and XhoI restriction site. The PCR fragment is then inserted into NheI and XhoI linearized pET28b vector.

To construct F1mut2 in which aa residues 15 to 21 are duplicated at the COOH-terminus, a reverse primer with a 5'-tag corresponding to the 15 to 21 aa sequence and XhoI restriction site is used for PCR amplification. The F1mut2 fragment is then inserted into NheI and XhoI linearized pET28b vector. To construct F1-V recombinants, V is first amplified and inserted into BamHI and HindIII linearized pET28b vector to generate the pET-V clone. F1 and F1mut2 are amplified with primers containing NheI and BamHI restriction sites, digested with NheI and BamHI, and ligated with the pET-V vector DNA digested with the same restriction enzymes. The resulting F1-V and F1mut-V plasmids contain F1 or F1mut in-frame fusion with V and a 23-aa vector sequence containing the hexa-histidine sequence at the $NH_2$-terminus of F1. The F1mut-V10 is amplified by overlap PCR using F1mut-V as the template and the mutated DNA is inserted into the NheI and HindIII linearized pET28b vector.

T4 Soc gene or phage RB69 Soc gene is fused with V, F1, or YscF with a two amino acid linker Gly-Ser by overlap PCR and the amplified DNA is inserted into the pET28b vector. The fused products V-T4 Soc, F1-T4 Soc, V-RB69Soc, and F1-RB69 Soc are further fused to YscF by overlap PCR to generate V-Soc (T4 or RB69)-YscF and F1-Soc (T4 or RB69)-YscF. A two amino acid linker Gly-Ser is used as a linker between Soc and YscF. To construct F1-V-Soc clones, RB69 Soc gene is first amplified with end primers containing HindIII and XhoI restriction sites and inserted into the HindIII and XhoI linearized pET28b vector. This clone is then linearized by digestion with NheI and HindIII restriction enzymes. F1mut-V and F1mut-V10 DNAs are amplified by using the end primers containing NheI and HindIII restriction sites and inserted into the above plasmid. The resulting clones contain F1mut-V or F1mut-V10 fused in-frame to the $NH_2$-terminus of RB69 Soc and also contain the flanking vector sequences containing two hexa-histidine tags at both $NH_2$- and COOH-termini. The F1mut-V-Soc is then fused with YscF by overlap PCR with a two amino acid linker Gly-Ser between Soc and YscF. All of the clones are sequenced (Retrogen, CA) and only the clones containing approximately 100% sequence accuracy are used for protein purification.

Bioinformatics Analysis

The structural models of F1, V, YscF, and a T4 phage nanoparticle are constructed using Chimera version1.4.1.[62] The T cell epitopes are predicted using MetaMHC, a new web server which integrates the outputs of leading predictors by several popular ensemble strategies.[63] This is shown to generate statistically significant results that are more reliable than the individual predictors.[63] For the $CD4^+$ T cell epitope prediction, F1 protein sequence is screened against 14 human MHC-II alleles. Peptides identified as positive ones by at least one predictor method are considered as potential $CD4^+$ T cell epitopes. For the $CD8^+$ T cell epitope prediction, F1 is screened against 57 human MHC-I alleles. Peptides identified as positive by at least one ensemble predictor approaches are considered to be potential $CD8^+$ T cell epitopes. Default values are used for both the T cell epitope predictions.

Over-Expression, Solubility Analysis and Purification of Recombinant Plague Immunogens The *E. coli* BL21 (DE3) RIPL cells harboring various plague recombinant plasmids constructed as above are induced with 1 mM IPTG for 1 to 2 h at 30° C. The cells are harvested by centrifugation at 4,000 g for 15 min at 4° C. and the pellets are resuspended in 50 mM Tris-HCl (pH 8.0). Solubility analysis is carried out using bacterial protein extraction reagent (B-PER). The cells are lysed with B-PER and centrifuged at 12,000 g for approximately 10 min. The soluble supernatant and insoluble pellet fractions are analyzed by SDS-polyacrylamide gel electrophoresis (PAGE) as follows. The samples are boiled in a buffer containing SDS and β-mercaptoethanol, and are electrophoresed on a 12% or 15% (w/v) polyacrylamide gel. Since the protein aggregates will be dissociated into monomers under these conditions. The molecular weight differences reflect sizes of the polypeptide chains of F1, F1mut1, and F1mut2. For example, F1mut1 and Fmut2 are approximately 1.6 kDa and 2.2 kDa larger than F1 because F1mut1 has a two amino acid linker Ser-Ala and an eight amino acid His-tag comprising SEQ ID NO: 2 at the C-terminus. F1mut2, in addition, has the duplicated T cell epitope comprising SEQ ID NO: 1.

For protein purification, the cells are resuspended in a binding buffer (50 mM Tris-HCl pH 8.0, 300 mM NaCl and 20 mM imidazole) containing proteinase inhibitor cocktail. The cells are lysed by a French press at 12,000 psi and the soluble fractions containing the His-tagged fusion proteins are isolated by centrifugation at 34,000 g for 20 min. The supernatants are filtered through 0.22 μm filters and loaded onto 1 ml HISTRAP column pre-equilibrated with 20 ml of binding buffer. After washing with the binding buffer containing 50 mM imidazole, the proteins are eluted with 20-500 mM linear imidazole gradient. The peak fractions containing the desired protein are concentrated by AMICON Ultra-4 centrifugal filtration (approximately 10 kDa cut-off; Millipore). The proteins are further purified by gel filtration on Hi-load 16/60 SUPERDEX 200 column (AKTA-FPLC) in a buffer containing 20 mM Tris-HCl, pH 8.0 and 100 mM NaCl. The peak fractions containing the purified proteins are concentrated and stored at −80° C. The native F1 recombinant proteins are purified from the pellet containing the insoluble inclusion bodies. The pellet is dissolved in the binding buffer containing 8 M urea and loaded onto 1 ml HISTRAP column pre-equilibrated with the same buffer. The proteins are renatured by washing the column with a decreasing urea gradient (8 to 0 M) in the binding buffer. The bound proteins are then eluted with 20-500 mM linear imidazole gradient. If necessary, the peak fractions from the HISTRAP column are concentrated by AMICON Ultra-4 centrifugal filtration (approximately 10 kDa cut-off). The proteins are further purified by gel filtration on Hi-load 16/60 SUPERDEX 200 column as described above.

The levels of lipopolysaccharide (LPS) contamination in the purified recombinant *Y. pestis* antigens from *E. coli*; F1, LcrV, YscF, and F1mut-V, are determined using ENDOSAFE PTS system. This system consists of a handheld spectrophotometer and utilizes FDA approved disposable cartridges. At least three batches of each antigen are tested. The endotoxin levels ranged from 0.05 to 0.8 EU/ml, substantially lower than the maximum recommended in gene vectors and subunit vaccines, 10 and 20 EU/ml respectively, for preclinical research.[64]

In Vitro Binding of Plague Antigens on Phage T4 Capsid

In vitro binding of plague-Soc fusion protein on $Hoc^-Soc^-$ T4 phage is carried out as previously described.[29,30,32] About $3\times10^{10}$ phage particles are sedimented for 45 min at 34,000 g in EPPENDORF LOBIND tubes and resuspended in phosphate-buffered saline (PBS) buffer (pH 7.4). Various Soc fusion proteins are incubated with the resuspended $Hoc^-Soc^-$ phage at 4° C. for 45 min. The phage particles are sedimented at 34,000 g for 45 min and the supernatant containing the unbound protein is discarded. The phage pellet containing the bound plague antigen(s) is washed twice with excess buffer containing 20 mM Tris-HCl pH 8 and 100 mM NaCl. The final pellets are resuspended in PBS buffer (pH 7.4) and analyzed by SDS-PAGE. The gels are stained with Coomassie Blue R250 and the protein bands are quantified by laser densitometry. The density of Soc fusion protein, gp23*, and gp18 (major tail sheath protein; approximately 70 kDa) bands are determined for each lane separately and the copy number of bound plague antigen molecules per capsid is calculated using the known copy numbers of gp23* (930 molecules per capsid) or gp18 (138 molecules per capsid). A saturation binding curve relating the number of bound plague protein-Soc molecules per capsid (Y) and the concentration of unbound protein in the binding reaction (X) is generated by SIGMAPLOT software. The apparent Kd (association constant) and Bmax (maximum copies of Soc fusion protein bound per capsid) are determined using the following equation as programmed in the SIGMAPLOT software:

$$Y = \frac{B_{max}X}{Kd + X}$$

Mouse Immunizations and Challenge

Six to eight weeks female Balb/c mice (17-20 g) are purchased from Jackson Laboratories (Bar Harbor, Me.) and randomly grouped and acclimated for 7 days. Equivalent amounts of plague immunogen molecules, either soluble or phage-bound, are used for each immunization. For immunization of soluble antigens, the purified proteins (10 μg/mouse/immunization) are adsorbed on alhydrogel containing 0.19 mg of aluminum per dose. For the T4 displayed antigens, the phage particles are directly used without any adjuvant (10 μg of plague antigen/mouse/immunization). On days 0, 21 and 42, mice are vaccinated via the intramuscular route. Alternate legs are used for each immunization. Blood is drawn from each animal on days 0 (pre-bleeds), 35 and 49 and the sera obtained are stored frozen at −70° C. On day 56, mice are intranasally challenged with *Y. pestis* CO92 BEI strain [65] using the indicated $LD_{50}$. Animals are monitored and recorded twice daily for mortality or other symptoms for 48 to 88 days. The animals that survived are re-challenged intranasally at 48 or 88 days post-first challenge with the indicated $LD_{50}$ and monitored twice daily for a further 48 days.

Rat Immunization and Challenge

Female Brown Norway rats (approximately 50-75 g) are purchased from Charles River (Houston, Tex.). Upon arrival, animals are weighed and randomized into the treatment groups and are acclimated for several days before manipulation. The plague immunogens are prepared as described above. On days 0, 21 and 42, rats are vaccinated via the intramuscular route with 15 μg antigen in 50 μl PBS buffer. Alternate legs are used for each immunization. On day 56, animals are intranasally challenged with 5,000 $LD_{50}$ of *Y. pestis* CO92 BEI strain and are monitored twice daily for 30 days and clinical symptoms of disease and survival recorded.

Determination of IgG and IgG Subtype Antibodies

The IgG titers are determined by ELISA. Briefly, 96-well microtiter plates are coated with approximately 10 ng/well of purified F1, V, YscF, F1-V or F1mutV antigen at 4° C. overnight. Following blocking and washing, sera from naïve and immunized mice are serially diluted and incubated with the affixed antigens for 1 h at room temperature. Following several washes, horseradish peroxidase (HRP)-conjugated goat anti-mouse IgG secondary antibody is added to the wells at a dilution of 1:10,000. After incubation for 1 h at room temperature, the unbound antibody is removed and the wells are washed several times and the TMB (3,3',5,5'-tetramethylbenzidine) substrate is added. Following a 20 min incubation to develop the color, the reaction is quenched by the addition of 2 $NH_2SO_4$ and the absorbance is read at 450 nm using an ELISA reader. For IgG subtypes, horseradish peroxidase-conjugated goat anti-mouse IgG1 or IgG2a secondary antibodies are used.

Cytokines Analysis

Seven days after the second boost (day 49), mice are sacrificed and spleens are harvested to prepare splenocytes using the lymphocyte separation medium. The isolated lymphocytes are adjusted to approximately $5\times10^6$ cells/ml and 1 ml of lymphocytes seeded into each well. Triplicate cultures from each group are stimulated with purified F1-V (10 μg/ml). Additional control stimulators included medium only and concanavalin A (5 μg/ml). After approximately 48 h incubation at 37° C. in a humidified (5% $CO_2$ in air) incubator, culture supernatants are collected. Cytokines are measured using a multiplex assay. The results are analyzed in Prism and the statistical significance is determined by one way ANOVA with Bonferroni correction.

Accession Numbers of Genes F1 capsule antigen (caf1) [GeneID: 1172839, Sequence: NC_003134.1 (85950.86462)], lcrV [GeneID: 1172676; Sequence: NC_003131.1 (21935.22915, complement)], yscF [GeneID: 1172700, Sequence: NC_003131.1 (41026.41289)], and soc (RB69Soc) [GeneID:1494143, Sequence: NC_004928.1 (14980.15216, complement)].

Example 1

Designing a Soluble Monomeric F1 Mutant

Figure 2:
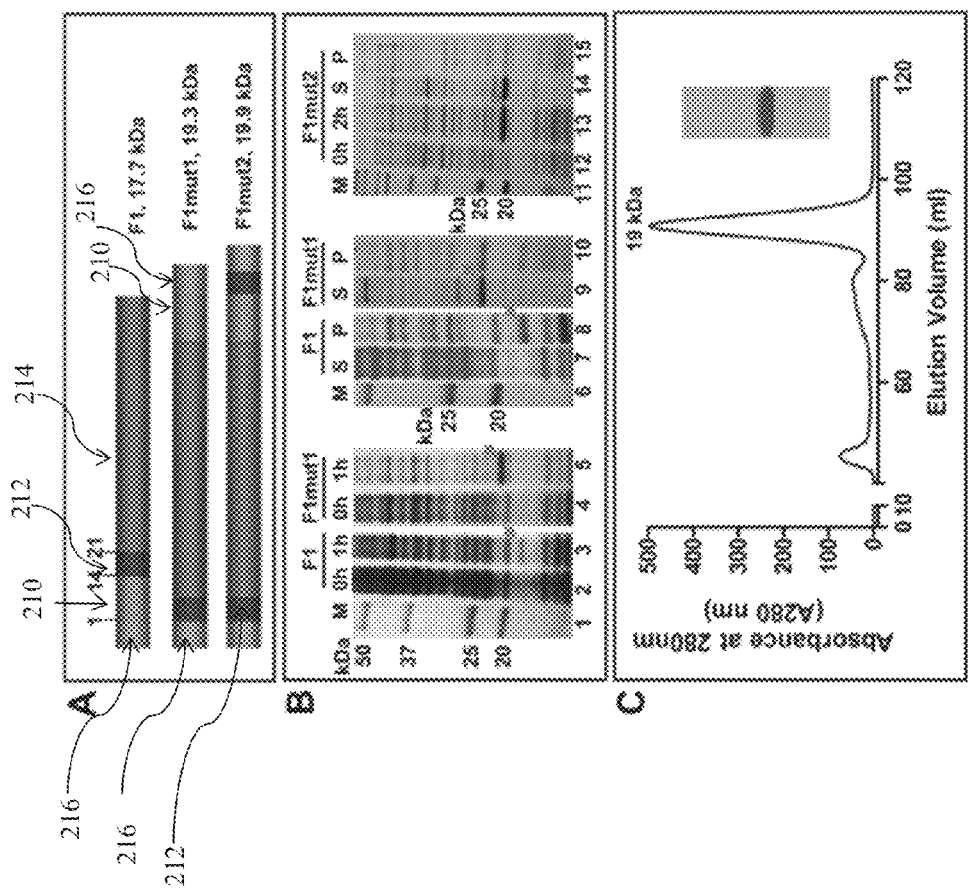
FIG. 2 is an illustration showing a design of monomeric F1 mutants. Panel A is a schematic of native F1, F1mut1, and F1mut2 recombinant constructs. Panel B shows an expression and solubility analysis of the recombinant proteins constructed according to the schematic in Panel A. Panel C illustrates the purification of F1mut1. Panel C includes a gel filtration profile showing that the F1mut1 is eluted as a symmetrical peak corresponding to a molecular mass of approximately 19 kDa. The insert in Panel C shows the purity of F1mut1 protein after SDS-PAGE and Coomassie Blue staining of the peak fraction.

Panel A of FIG. 2 is a schematic of native F1, F1mut1, and F1mut2 recombinant constructs. Shade 210 shows a coding sequence of a donor β-strand of F1. Shade 212 shows a coding sequence of a T cell epitope region. Shade 214 shows a rest of the F1 coding sequence. Native F1 has one hexa-histidine tag of SEQ ID NO: 2 shown in shade 216 at the $NH_2$-terminus of F1, whereas F1mut1 and F1mut2 have two hexa-histidine tags of SEQ ID NO: 2 shown in shade 216, one at the $NH_2$-terminus of F1 and another at the COOH-terminus of F1. The numbers above the shades 210, 212 and 216 correspond to the positions of amino acid residues of F1, for example, number 1 corresponds to the first $NH_2$-terminal amino acid residue of F1, number 14 corresponds to the 14th $NH_2$-terminal amino acid residue of F1, and number 21 corresponds to the 21th $NH_2$-terminal amino acid residue of F1.

Panel B of FIG. 2 shows an expression and solubility analysis of the recombinant proteins constructed according to the schematic in Panel A of FIG. 2. The recombinant F1 proteins are over-expressed by adding IPTG to 1 mM final concentration. The samples at 0 h, 1 h, or 2 h time points are analyzed by SDS-PAGE (15% gel) and Coomassie Blue staining. The positions of F1 protein bands are marked with arrows. The samples at 1 h or 2 h time points are analyzed for solubility using the B-PER reagent. "S" refers to soluble fraction (supernatant from 12,000 g centrifugation of the lysate). "P" refers to insoluble fraction (pellet). "M" refers to molecular weight standards.

Data in Panel B of FIG. 1 demonstrates that an over-expression of the F1 gene in a heterologous system such as *E. coli* exposes the unfilled hydrophobic cleft, resulting in uncontrolled aggregation of F1 subunits into insoluble inclusion bodies. As shown in image of Coomassie Blue in Panel B of FIG. 1, all of the over-produced F1 protein partitioned into the pellet (lane 8) and none is detected in the supernatant (lane 7). Denaturation of the insoluble protein recovered some of the F1 protein into the soluble fraction but it still aggregates rapidly leading to precipitation (in the HISTRAP column) upon removal of the denaturant. Similar aggregation behavior of F1 is observed in previously published studies.[38,39]

According to disclosed embodiments, shifting of the $NH_2$-terminal β-strand of F1 to the COOH-terminus of F1 reorients the β-strand such that it fills its own cleft (intra-molecular complementation) (Panel B of FIG. 1), and furthermore, it no longer requires the assistance of chaperone or usher proteins. In this example, an F1 mutant (recombinant protein F1mut1) is constructed by deleting the $NH_2$-terminal donor strand [amino acid (aa) residues 1-14] and fusing it to the COOH-terminus with a short linker (Ser-Ala) in between (Panel A of FIG. 2). The recombinant F1mut1, as predicted, folded into a soluble protein in the absence of Caf1M or Caf1A, and approximately 70% of the protein partitioned into the cell-free lysate (see lanes 9 and 10 of Panel B of FIG. 2). In addition, the mutated F1 protein is expressed at significantly higher levels than that of the native F1 protein after IPTG induction (Panel B of FIG. 2, compare lane 5 with lane 3).

The recombinant protein F1mut1 is purified from the cell-free lysates by HISTRAP affinity chromatography followed by Hi-load 16/60 SUPERDEX 200 gel filtration. The molecular weight of F1mut1 peak fraction is calculated from the calibration curve constructed by gel filtration on the same column of standard proteins of known molecular weight [Thyroglobulin (669 kDa), Ferritin (440 kDa), Catalase (232 kDa), aldolase (158 kDa), Ovalbumin (43 kDa), RNase A (14 kDa), and Albumin (67 kDa)]. A gel filtration profile showes that the F1mut1 is eluted as a symmetrical peak corresponding to a molecular mass of approximately 19 kDa (Panel C of FIG. 2), a monomer, suggesting that the interlocking mechanism had shifted from inter- to intra-molecular interactions. The insert in Panel C of FIG. 2 shows the purity of F1mut1 protein after SDS-PAGE and Coomassie Blue staining of the peak fraction. Similar results are obtained with the recombinant protein F1mut2. See Materials and Methods described above for additional details.

Example 2

Restoring the Potential T Cell Epitopes of F1 Mutant

In this example, a bioinformatics approach is used to determine if shifting of the $NH_2$-terminal β-strand of F1 to the COOH-terminus of F1 disrupts the $NH_2$-terminal epitopes of F1. The aa residues 7 to 20 are reported to contain a mouse H-2-IA$^d$ restricted CD4$^+$ T cell epitope.

CD8$^+$ and CD4$^+$ T cell epitopes are predicted using MetaMHC with default values. Peptides identified as positive by at least one ensemble predictor approach are considered to be potential CD8$^+$ T cell epitopes or potential CD4$^+$ T cell epitopes.

Predicted CD8+ T cell epitopes are shown in Table 1 below. Highlighted cells indicate high ranking scores that predict a potential CD8+ T cell epitope. Predicted CD4+ T cell epitopes are shown in Table 2 below.

TABLE 1

The predicted CD8$^+$ T cell epitopes:

| | | | Methods used for epitope prediction | | | | | | |
|---|---|---|---|---|---|---|---|---|---|
| Allele | Position | peptide | ANN | SMM | NetMHC | NetMHC Pan | Consensus | PM | AvgTanh |
| HLA A*0101 | 138-146 | YTDAVTVTV (SEQ ID NO: 6) | 59.3 | 138 | 117 | 94.4 | 0.999 | | 0.8421 |
| | 62-70 | FTDAAGDPM (SEQ ID NO: 7) | 325.9 | 539.9 | 1602 | 137.2 | 0.996 | 61.987 | 0.8149 |
| | 6-14 | STTATATLV (SEQ ID NO: 8) | 9916.2 | 2678.2 | 6400 | 2134.6 | 0.979 | 9.4645 | 0.7374 |
| | 3-11 | LTASTTATA (SEQ ID NO: 9) | 9123.5 | 2350.9 | 14883 | 2462.3 | 0.9775 | 8.2556 | 0.736 |

TABLE 1-continued

The predicted CD8+ T cell epitopes:

| Allele | Position | peptide | ANN | SMM | NetMHC | NetMHC Pan | Consensus | PM | AvgTanh |
|---|---|---|---|---|---|---|---|---|---|
| | 115-123 | ATGSQDFFV (SEQ ID NO: 10) | 10097.4 | 3794.7 | 10875 | 2877.3 | 0.974 | 7.0794 | 0.7257 |
| | 74-82 | FTSQDGNNH (SEQ ID NO: 11) | 11247.4 | 8291.7 | 7860 | 4523.7 | 0.9738 | 4.4891 | 0.7047 |
| | 15-23 | EPARITLTY (SEQ ID NO: 12) | 15146 | 4479.6 | 19506 | 2814.7 | 0.9571 | 5.3529 | 0.687 |
| | 55-63 | TTSTSVNFT (SEQ ID NO: 13) | 11617. | 6486.9 | 5267 | 13117 | 0.9567 | 1.5686 | 0.6576 |
| HLA A*0201 | 138-146 | YTDAVTVTV (SEQ ID NO: 6) | 15 | 67.4 | 15 | 10.9 | 0.9982 | 33.9982 | 0.7844 |
| | 115-123 | ATGSQDFFV (SEQ ID NO: 10) | 552 | 526.2 | 196 | 350.5 | 0.9726 | 10.7835 | 0.696 |
| HLA A*0202 | 138-146 | YTDAVTVTV (SEQ ID NO: 6) | 52.7 | 111.8 | 70 | 19.1 | 0.984 | 17.2995 | 0.7035 |
| | 115-123 | ATGSQDFFV (SEQ ID NO: 10) | 140.4 | 218.1 | 103 | 328.2 | 0.9691 | 9.4752 | 0.663 |
| | 106-114 | NLVGDDVVL (SEQ ID NO: 14) | 231.2 | 128.6 | 216 | 1028.5 | 0.9694 | 6.7764 | 0.6441 |
| HLA A*0203 | 3-11 | LTASTTATA (SEQ ID NO: 9) | 64 | 283.8 | 39 | 66.4 | 0.9796 | 14.9505 | 0.6862 |
| | 138-146 | YTDAVTVTV (SEQ ID NO: 6) | 185.1 | 280.1 | 54 | 40.6 | 0.9729 | 13.3352 | 0.6779 |
| | 9-17 | ATATLVEPA (SEQ ID NO: 15) | 153.1 | 279.9 | 88 | 282.7 | 0.9666 | 9.7571 | 0.6611 |
| HLA A*0204 | 138-146 | YTDAVTVTV (SEQ ID NO: 6) | | | 84 | 32.8 | 0.9965 | | 0.84 |
| | 115-123 | ATGSQDFFV (SEQ ID NO: 10) | | | 64 | 329.5 | 0.9924 | | 0.7991 |
| | 6-14 | STTATATLV (SEQ ID NO: 8) | | | 316 | 1289.2 | 0.9734 | | 0.7298 |
| HLA A*0206 | 138-146 | YTDAVTVTV (SEQ ID NO: 6) | 8 | 21.7 | 11 | 6.8 | 0.9972 | 30.8606 | 0.7174 |
| | 115-123 | ATGSQDFFV (SEQ ID NO: 10) | 111.2 | 169.1 | 92 | 108.1 | 0.9767 | 13.0157 | 0.6561 |
| | 6-14 | STTATATLV (SEQ ID NO: 8) | 105.4 | 197.8 | 109 | 196.2 | 0.974 | 11.7425 | 0.6501 |
| | 62-70 | FTDAAGDPM (SEQ ID NO: 7) | 105.3 | 155 | 188 | 202 | 0.9704 | 11.1491 | 0.6483 |
| HLA A*0211 | 138-146 | YTDAVTVTV (SEQ ID NO: 6) | 3 | 12 | 3 | 2.2 | 0.9948 | | 0.7157 |
| | 138-146 | YTDAVTVTV (SEQ ID NO: 6) | 7.5 | 58.9 | 4 | 6.4 | 0.9957 | | 0.7545 |
| HLA A*0212 | 40-48 | ELLVGTLTL (SEQ ID NO: 16) | 101.8 | 730 | 16 | 779.8 | 0.9667 | | 0.6778 |
| | 115-123 | ATGSQDFFV (SEQ ID NO: 10) | 226.3 | 488.7 | 442 | 156.2 | 0.9656 | | 0.6732 |
| | 106-114 | NLVGDDVVL (SEQ ID NO: 14) | 247.9 | 39.7 | 42 | 1517.4 | 0.9749 | | 0.6711 |
| HLA A*0216 | 138-146 | YTDAVTVTV (SEQ ID NO: 6) | 7.9 | 11.2 | 8 | 4.4 | 0.9975 | | 0.7406 |
| | 115-123 | ATGSQDFFV (SEQ ID NO: 10) | 21.3 | 106.5 | 14 | 47.8 | 0.982 | | 0.7051 |
| | 40-48 | ELLVGTLTL (SEQ ID NO: 16) | 50.5 | 183 | 6 | 419.3 | 0.9769 | | 0.68 |
| HLA A*0219 | 138-146 | YTDAVTVTV (SEQ ID NO: 6) | 24.8 | 144.3 | 6 | 6.4 | 0.9961 | | 0.786 |
| | 40-48 | ELLVGTLTL (SEQ ID NO: 16) | 14.5 | 73.9 | 20 | 948.5 | 0.9924 | | 0.7409 |
| | 106-114 | NLVGDDVVL (SEQ ID NO: 14) | 1750.7 | 69.4 | 437 | 2545.1 | 0.9702 | | 0.6701 |
| HLA A*0250 | 138-146 | YTDAVTVTV (SEQ ID NO: 6) | 9.4 | 62.6 | | 93 | 0.9824 | | 0.6073 |

TABLE 1-continued

The predicted CD8+ T cell epitopes:

Methods used for epitope prediction

| Allele | Position | peptide | ANN | SMM | NetMHC | NetMHC Pan | Consensus | PM | AvgTanh |
|---|---|---|---|---|---|---|---|---|---|
| HLA A*0301 | 44-52 | GTLTLGGYK (SEQ ID NO: 17) | 126.9 | 257.8 | 64 | 110.4 | 0.997 | 23.4818 | 0.7992 |
| | 124-132 | RSIGSKGGK (SEQ ID NO: 18) | 214.8 | 262 | 216 | 478.9 | 0.9941 | 16.634 | 0.7735 |
| | 129-137 | KGGKLAAGK (SEQ ID NO: 19) | 2747.1 | 1541 | 3933 | 2306.2 | 0.9718 | 3.4371 | 0.6822 |
| | 121-129 | FFVRSIGSK (SEQ ID NO: 20) | 7891 | 2239.3 | 1377 | 2222.7 | 0.9674 | 2.4575 | 0.6512 |
| HLA A*2402 | 66-74 | AGDPMYLTF (SEQ ID NO: 21) | 4777.4 | 1719.5 | 17696 | 6562.3 | 0.9758 | -0.0957 | 0.6669 |
| | 113-121 | VLATGSQDF (SEQ ID NO: 22) | 4354.9 | 2130.2 | 9448 | 23998.5 | 0.9675 | -0.6753 | 0.63 |
| HLA A*2403 | 70-78 | MYLTFTSQD (SEQ ID NO: 23) | 429.7 | 14.1 | 5500 | 4652.3 | 0.9702 | | 0.6988 |
| | 66-74 | AGDPMYLTF (SEQ ID NO: 21) | 4908.1 | 657.3 | 6978 | 562.4 | 0.9502 | | 0.6667 |
| | 76-84 | SQDGNNHQF (SEQ ID NO: 24) | 6312.4 | 1996.8 | 8479 | 280.8 | 0.9417 | | 0.6609 |
| HLA A*2501 | 38-46 | DTELLVGTL (SEQ ID NO: 25) | 2226.2 | 144.8 | | 5822 | 0.9912 | | 0.712 |
| | 15-23 | EPARITLTY (SEQ ID NO: 12) | 2130.9 | 983.7 | | 489.2 | 0.9916 | | 0.7099 |
| | 111-119 | DVVLATGSQ (SEQ ID NO: 26) | 1974.1 | 838 | | 15236.1 | 0.9866 | | 0.6961 |
| HLA A*2601 | 15-23 | EPARITLTY (SEQ ID NO: 12) | 2018.5 | 998.8 | 3308 | 181.3 | 0.9869 | 49.4191 | 0.7747 |
| | 111-119 | DVVLATGSQ (SEQ ID NO: 26) | 4874.1 | 1326.4 | 14407 | 3963.9 | 0.9785 | 14.8468 | 0.6999 |
| | 62-70 | FTDAAGDPM (SEQ ID NO: 7) | 13964.4 | 1384.7 | 15541 | 1849.9 | 0.9625 | 10.934 | 0.6612 |
| HLA A*2602 | 15-23 | EPARITLTY (SEQ ID NO: 12) | 497.2 | 45.4 | 341 | 28.8 | 0.9863 | | 0.7377 |
| | 62-70 | FTDAAGDPM (SEQ ID NO: 7) | 9574.8 | 98.6 | 255 | 123.4 | 0.9826 | | 0.6744 |
| | 38-46 | DTELLVGTL (SEQ ID NO: 25) | 3879.3 | 144.9 | 727 | 448.9 | 0.9746 | | 0.6701 |
| | 111-119 | DVVLATGSQ (SEQ ID NO: 26) | 753 | 496.8 | 23192 | 686.8 | 0.954 | | 0.6666 |
| HLA A*2603 | 40-48 | ELLVGTLTL (SEQ ID NO: 16) | 709.4 | 1251.8 | | 22809.6 | 0.9576 | | 0.6582 |
| | 62-70 | FTDAAGDPM (SEQ ID NO: 7) | 3008.3 | 208.3 | | 3780.2 | 0.9818 | | 0.6514 |
| | 15-23 | EPARITLTY (SEQ ID NO: 12) | 4313.2 | 308.5 | | 1759.7 | 0.9874 | | 0.6448 |
| | 111-119 | DVVLATGSQ (SEQ ID NO: 26) | 3972 | 3400.1 | | 7218.6 | 0.97 | | 0.6188 |
| HLA A*2902 | 15-23 | EPARITLTY (SEQ ID NO: 12) | 817.4 | 225.2 | 819 | 330.8 | 0.9846 | 7.8134 | 0.7289 |
| | 63-71 | TDAAGDPMY (SEQ ID NO: 27) | 294.1 | 289.8 | 10993 | 6113.4 | 0.9609 | 1.925 | 0.6728 |
| HLA A*3001 | 16-24 | PARITLTYK (SEQ ID NO: 28) | 13.4 | 50.5 | 241 | 44.7 | 0.9877 | 79.8723 | 0.7132 |
| | 124-132 | RSIGSKGGK (SEQ ID NO: 18) | 80 | 124.6 | 40 | 25.5 | 0.9839 | | 0.7067 |
| | 44-52 | GTLTLGGYK (SEQ ID NO: 17) | 113.6 | 111.5 | 447 | 79.9 | 0.9746 | 53.7159 | 0.6804 |
| | 52-60 | KTGTTSTSV (SEQ ID NO: 29) | 343.5 | 246.5 | 4727 | 78.7 | 0.9538 | 43.5615 | 0.651 |
| HLA A*3002 | 43-51 | VGTLTLGGY (SEQ ID NO: 30) | 83.5 | 123.7 | 11113 | 766.9 | 0.9816 | 8.8231 | 0.7082 |
| | 130-138 | GGKLAAGKY (SEQ ID NO: 31) | 340.2 | 120.4 | 17505 | 1539.2 | 0.97 | 4.012 | 0.6751 |
| | 44-52 | GTLTLGGYK (SEQ ID NO: 17) | 412.6 | 544 | 201 | 244.9 | 0.9704 | 17.395 | 0.6682 |

TABLE 1-continued

The predicted CD8+ T cell epitopes:

Methods used for epitope prediction

| Allele | Position | peptide | ANN | SMM | NetMHC | NetMHC Pan | Consensus | PM | AvgTanh |
|---|---|---|---|---|---|---|---|---|---|
| HLA A*3201 | 52-60 | KTGTTSTSV (SEQ ID NO: 29) | 126 | 159.6 | | 226.8 | 0.986 | 4.5679 | 0.7168 |
| | 54-62 | GTTSTSVNF (SEQ ID NO: 32) | 191.7 | 189 | | 280.8 | 0.9842 | 3.8872 | 0.7078 |
| | 138-146 | YTDAVTVTV (SEQ ID NO: 6) | 127.1 | 657.1 | | 211.7 | 0.9868 | 3.9987 | 0.7051 |
| | 118-126 | SQDFFVRSI (SEQ ID NO: 33) | 229.3 | 152.9 | | 357.6 | 0.9804 | 3.6174 | 0.7051 |
| | 11-19 | ATLVEPARI (SEQ ID NO: 34) | 530.4 | 229.1 | | 1193.7 | 0.971 | 1.7813 | 0.6793 |
| | 40-48 | ELLVGTLTL (SEQ ID NO: 16) | 277.7 | 468.9 | | 3716.4 | 0.948 | 1.2904 | 0.6759 |
| | 21-29 | LTYKEGAPI (SEQ ID NO: 35) | 1060 | 1051.9 | | 105.1 | 0.9694 | 2.4168 | 0.6706 |
| | 5-13 | ASTTATATL (SEQ ID NO: 36) | 420.5 | 663.4 | | 2591.9 | 0.9314 | 1.0012 | 0.6686 |
| HLA A*3301 | 10-18 | TATLVEPAR (SEQ ID NO: 37) | 203.2 | 276.6 | 145 | 491 | 0.9861 | 24.3677 | 0.7268 |
| HLA A*6801 | 10-18 | TATLVEPAR (SEQ ID NO: 37) | 12.3 | 21.3 | 5 | 45.3 | 0.9916 | 26.7757 | 0.7406 |
| | 116-124 | TGSQDFFVR (SEQ ID NO: 38) | 277.4 | 112.5 | 143 | 345.2 | 0.9682 | 8.9889 | 0.6706 |
| HLA A*6802 | 138-146 | YTDAVTVTV (SEQ ID NO: 6) | 11.3 | 45.8 | 33 | 14.6 | 0.9977 | 35.8551 | 0.7478 |
| | 6-14 | STTATATLV (SEQ ID NO: 8) | 21 | 74.6 | 48 | 16.7 | 0.9952 | 31.6877 | 0.7379 |
| | 3-11 | LTASTTATA (SEQ ID NO: 9) | 57.3 | 199.7 | 143 | 30.5 | 0.9869 | 23.3999 | 0.714 |
| | 9-17 | ATATLVEPA (SEQ ID NO: 15) | 13.6 | 158.7 | 46 | 254.6 | 0.9898 | 25.4081 | 0.7134 |
| | 64-72 | DAAGDPMYL (SEQ ID NO: 39) | 53.9 | 176.6 | 50 | 152.9 | 0.9878 | 21.2437 | 0.7059 |
| | 58-66 | TSVNFTDAA (SEQ ID NO: 40) | 79.1 | 275.1 | 57 | 108.6 | 0.9864 | 20.2662 | 0.7026 |
| | 55-63 | TTSTSVNFT (SEQ ID NO: 13) | 71.3 | 370.1 | 180 | 301.2 | 0.9786 | 16.061 | 0.6862 |
| | 115-123 | ATGSQDFFV (SEQ ID NO: 10) | 245 | 364.1 | 186 | 242.7 | 0.9777 | 13.1418 | 0.6747 |
| HLA A*6901 | 138-146 | YTDAVTVTV (SEQ ID NO: 6) | 5.1 | 17 | 6 | 6.1 | 0.9996 | | 0.7974 |
| | 6-14 | STTATATLV (SEQ ID NO: 8) | 37 | 99.8 | 85 | 31.4 | 0.9954 | | 0.7522 |
| | 62-70 | FTDAAGDPM (SEQ ID NO: 7) | 62.3 | 164.3 | 133 | 173.2 | 0.9902 | | 0.7268 |
| | 3-11 | LTASTTATA (SEQ ID NO: 9) | 253.2 | 406.9 | 93 | 72.5 | 0.988 | | 0.7166 |
| | 40-48 | ELLVGTLTL (SEQ ID NO: 16) | 48.2 | 312.8 | 60 | 1953.4 | 0.9872 | | 0.6987 |
| | 21-29 | LTYKEGAPI (SEQ ID NO: 35) | 219.7 | 425.8 | 196 | 441.6 | 0.9811 | | 0.6951 |
| | 64-72 | DAAGDPMYL (SEQ ID NO: 39) | 240.4 | 326.5 | 107 | 760.4 | 0.9808 | | 0.6914 |
| | 115-123 | ATGSQDFFV (SEQ ID NO: 10) | 913 | 233.4 | 392 | 161.5 | 0.9822 | | 0.6856 |
| HLA A*8001 | 15-23 | EPARITLTY (SEQ ID NO: 12) | 124.9 | 229.1 | | 5377.4 | 0.9902 | | 0.7414 |
| | 43-51 | VGTLTLGGY (SEQ ID NO: 30) | 4753 | 905 | | 5409.9 | 0.9706 | | 0.6655 |
| HLA B*0702 | 99-107 | SPKVNGENL (SEQ ID NO: 41) | 228.5 | 212.6 | 67 | 171.5 | 0.9934 | 27.4616 | 0.7759 |
| | 13-21 | LVEPARITL (SEQ ID NO: 42) | 1215.9 | 992.8 | 719 | 1098.3 | 0.98 | 12.0184 | 0.7088 |
| HLA B*0801 | 40-48 | ELLVGTLTL (SEQ ID NO: 16) | 2672.6 | 972.1 | 12249 | 2018.3 | 0.9656 | 12.651 | 0.6924 |

TABLE 1-continued

The predicted CD8+ T cell epitopes:

Methods used for epitope prediction

| Allele | Position | peptide | ANN | SMM | NetMHC | NetMHC Pan | Consensus | PM | AvgTanh |
|---|---|---|---|---|---|---|---|---|---|
| HLA B*0802 | 99-107 | SPKVNGENL (SEQ ID NO: 41) | 11002 | 7279 | 34987 | 32977.9 | 0.9864 | | 0.7136 |
| | 15-23 | EPARITLTY (SEQ ID NO: 12) | 15131.9 | 37002.1 | 47882 | 28063.9 | 0.8898 | | 0.6892 |
| HLA B*0803 | 99-107 | SPKVNGENL (SEQ ID NO: 41) | 10361 | 1984.5 | | | 0.9912 | | 0.7064 |
| | 113-121 | VLATGSQDF (SEQ ID NO: 22) | 15753.7 | 8917.4 | | | 0.9409 | | 0.6339 |
| HLA B*1501 | 113-121 | VLATGSQDF (SEQ ID NO: 22) | 136.5 | 461.7 | 186 | 75.5 | 0.9918 | 19.6771 | 0.7104 |
| | 21-29 | LTYKEGAPI (SEQ ID NO: 35) | 358.2 | 556.7 | 6195 | 560.1 | 0.9733 | 8.8593 | 0.6541 |
| | 76-84 | SQDGNNHQF (SEQ ID NO: 24) | 1347.4 | 636.9 | 392 | 1836.2 | 0.9626 | 6.8116 | 0.6345 |
| HLA B*1502 | 113-121 | VLATGSQDF (SEQ ID NO: 22) | 64.2 | 45.1 | | 426.4 | 0.9846 | | 0.6889 |
| | 40-48 | ELLVGTLTL (SEQ ID NO: 16) | 1719.6 | 40.2 | | 4329.9 | 0.9742 | | 0.6078 |
| HLA B*1503 | 136-144 | GKYTDAVTV (SEQ ID NO: 43) | 29.6 | 17.1 | | 100.1 | 0.9726 | 6.5537 | 0.6379 |
| | 113-121 | VLATGSQDF (SEQ ID NO: 22) | 50.6 | 62.9 | | 40.6 | 0.983 | 6.1082 | 0.6327 |
| HLA B*1509 | 81-89 | NHQFTTKVI (SEQ ID NO: 44) | 975.7 | 314.6 | | 3588 | 0.9972 | | 0.7275 |
| | 5-13 | ASTTATATL (SEQ ID NO: 36) | 8.2 | 2.4 | | 11.7 | 0.9946 | | 0.6826 |
| HLA B*1517 | 21-29 | LTYKEGAPI (SEQ ID NO: 35) | 14.6 | 2.4 | | 6.3 | 0.9966 | | 0.6791 |
| | 54-62 | GTTSTSVNF (SEQ ID NO: 32) | 6.7 | 20.6 | | 7.5 | 0.996 | | 0.6748 |
| | 11-19 | ATLVEPARI (SEQ ID NO: 34) | 18.9 | 9.2 | | 113.8 | 0.9858 | | 0.6589 |
| HLA B*1801 | 15-23 | EPARITLTY (SEQ ID NO: 12) | 2718.7 | 3623.5 | 3568 | 967.2 | 0.9762 | -0.6173 | 0.6864 |
| | 39-47 | TELLVGTLT (SEQ ID NO: 45) | 4635.5 | 2931.7 | 4242 | 2985.1 | 0.9686 | -2.4987 | 0.651 |
| HLA B*2705 | 93-101 | SRDFDISPK (SEQ ID NO: 46) | 1778.7 | 608.6 | 2340 | 1789.4 | 0.9728 | | 0.668 |
| | 17-25 | ARITLTYKE (SEQ ID NO: 47) | 2303.8 | 1806.8 | 2470 | 1058.6 | 0.9648 | | 0.6639 |
| HLA B*3501 | 15-23 | EPARITLTY (SEQ ID NO: 12) | 7.7 | 6.2 | 7 | 3.8 | 0.9998 | 46.8204 | 0.7968 |
| | 62-70 | FTDAAGDPM (SEQ ID NO: 7) | 75.8 | 127.7 | 64 | 83.4 | 0.9919 | 22.3804 | 0.7274 |
| | 68-76 | DPMYLTFTS (SEQ ID NO: 48) | 131.1 | 126.4 | 244 | 286.1 | 0.9878 | 16.4819 | 0.701 |
| | 114-122 | LATGSQDFF (SEQ ID NO: 49) | 219.5 | 234.7 | 410 | 960.7 | 0.9804 | 12.0409 | 0.6738 |
| | 63-71 | TDAAGDPMY (SEQ ID NO: 27) | 919.1 | 417.9 | 330 | 5103 | 0.9728 | 6.4352 | 0.6286 |
| HLA B*3801 | 81-89 | NHQFTTKVI (SEQ ID NO: 44) | 13519.1 | 1538.5 | | 9323 | 0.986 | | 0.6706 |
| | 76-84 | SQDGNNHQF (SEQ ID NO: 24) | 10354.3 | 31596.3 | | 8218.1 | 0.9864 | | 0.6638 |
| | 23-31 | YKEGAPITI (SEQ ID NO: 50) | 22462.2 | 5741.3 | | 2616.9 | 0.9576 | | 0.6413 |
| | 13-21 | LVEPARITL (SEQ ID NO: 42) | 12930.8 | 16142.5 | | 21508.9 | 0.9318 | | 0.6298 |

TABLE 1-continued

The predicted CD8+ T cell epitopes:

| Allele | Position | peptide | ANN | SMM | NetMHC | NetMHC Pan | Consensus | PM | AvgTanh |
|---|---|---|---|---|---|---|---|---|---|
| HLA B*3901 | 23-31 | YKEGAPITI (SEQ ID NO: 50) | 92.8 | 448.5 | 1006 | 130.3 | 0.994 | | 0.7821 |
| | 76-84 | SQDGNNHQF (SEQ ID NO: 24) | 591.4 | 888.1 | 923 | 1546.4 | 0.9824 | | 0.7411 |
| | 81-89 | NHQFTTKVI (SEQ ID NO: 44) | 829.9 | 514.5 | 3308 | 1208.6 | 0.9856 | | 0.7363 |
| | 106-114 | NLVGDDVVL (SEQ ID NO: 14) | 498.2 | 150.2 | 10302 | 3234.2 | 0.9788 | | 0.7294 |
| | 40-48 | ELLVGTLTL (SEQ ID NO: 16) | 657 | 859.5 | 3849 | 2156.6 | 0.9814 | | 0.7276 |
| | 138-146 | YTDAVTVTV (SEQ ID NO: 6) | 535 | 2034.1 | 3891 | 1988.3 | 0.9764 | | 0.7268 |
| | 118-126 | SQDFFVRSI (SEQ ID NO: 33) | 3188 | 2262.4 | 11730 | 482.6 | 0.9668 | | 0.7021 |
| | 136-144 | GKYTDAVTV (SEQ ID NO: 43) | 1996.9 | 2257.1 | 27576 | 3282.4 | 0.9532 | | 0.6833 |
| | 82-90 | HQFTTKVIG (SEQ ID NO: 51) | 1740.5 | 903 | 31399 | 5769.3 | 0.9484 | | 0.6763 |
| | 5-13 | ASTTATATL (SEQ ID NO: 36) | 2971.7 | 6783.5 | 7131 | 5936.5 | 0.945 | | 0.6582 |
| HLA B*4001 | 24-32 | KEGAPITIM (SEQ ID NO: 52) | 633.3 | 324.1 | 1947 | 323 | 0.993 | 49.5406 | 0.7902 |
| | 104-112 | GENLVGDDV (SEQ ID NO: 53) | 324.2 | 212.4 | 549 | 1126 | 0.9942 | | 0.7883 |
| | 76-84 | SQDGNNHQF (SEQ ID NO: 24) | 7692.4 | 2253.1 | 3933 | 9227.5 | 0.9732 | 6.7596 | 0.6504 |
| HLA B*4002 | 24-32 | KEGAPITIM (SEQ ID NO: 52) | 278.8 | 168.4 | 1968 | 257.6 | 0.9943 | 7.5012 | 0.797 |
| | 94-102 | RDFDISPKV (SEQ ID NO: 54) | 180.5 | 182.6 | 9146 | 114.8 | 0.9957 | 8.4816 | 0.7955 |
| | 104-112 | GENLVGDDV (SEQ ID NO: 53) | 1786.1 | 1299.1 | 3766 | 5638.9 | 0.9873 | -0.5968 | 0.7061 |
| | 24-32 | KEGAPITIM (SEQ ID NO: 52) | 2228.9 | 4184.8 | 3344 | 4613.7 | 0.9866 | -1.1406 | 0.6988 |
| | 39-47 | TELLVGTLT (SEQ ID NO: 45) | 6837.2 | 4189.4 | 8297 | 3091.9 | 0.967 | -3.4574 | 0.6657 |
| HLA B*4403 | 104-112 | GENLVGDDV (SEQ ID NO: 53) | 1315.4 | 1032.2 | 2055 | 2673.4 | 0.9873 | 0.9949 | 0.7412 |
| | 39-47 | TELLVGTLT (SEQ ID NO: 45) | 3615 | 3983.7 | 2033 | 1195.1 | 0.981 | 0.2632 | 0.7263 |
| | 24-32 | KEGAPITIM (SEQ ID NO: 52) | 3337.2 | 2480.6 | 3646 | 1339.2 | 0.9762 | -0.2196 | 0.7244 |
| HLA B*4501 | 104-112 | GENLVGDDV (SEQ ID NO: 53) | 590.1 | 512.4 | 1183 | 864.6 | 0.9891 | 6.1365 | 0.7583 |
| | 39-47 | TELLVGTLT (SEQ ID NO: 45) | 1293 | 493.9 | 6263 | 524.2 | 0.9823 | 4.0199 | 0.7377 |
| | 24-32 | KEGAPITIM (SEQ ID NO: 52) | 3597 | 5363.6 | 6829 | 3068.3 | 0.9686 | -1.167 | 0.6769 |
| | 1-9 | ADLTASTTA (SEQ ID NO: 55) | 4385.1 | 665.2 | 6756 | 11184.4 | 0.967 | -1.7047 | 0.6456 |
| HLA B*4601 | 62-70 | FTDAAGDPM (SEQ ID NO: 7) | 10726.5 | 1559.4 | | 7426.4 | 0.9924 | | 0.6837 |
| | 134-142 | AAGKYTDAV (SEQ ID NO: 56) | 11109.7 | 4486.5 | | 23447.9 | 0.9854 | | 0.6623 |
| | 21-29 | LTYKEGAPI (SEQ ID NO: 35) | 10059.8 | 40641 | | 3883.3 | 0.9884 | | 0.6606 |
| | 138-146 | YTDAVTVTV (SEQ ID NO: 6) | 14000.4 | 14907.6 | | 12652.9 | 0.9708 | | 0.6284 |
| HLA B*4801 | 82-90 | HQFTTKVIG (SEQ ID NO: 51) | 5396.5 | 6738 | | 25374.6 | 0.9632 | | 0.648 |
| HLA B*5101 | 15-23 | EPARITLTY (SEQ ID NO: 12) | 9933.7 | 9019.8 | 2722 | 4595.8 | 0.9884 | -3.8522 | 0.7363 |

TABLE 1-continued

The predicted CD8+ T cell epitopes:

Methods used for epitope prediction

| Allele | Position | peptide | ANN | SMM | NetMHC | NetMHC Pan | Consensus | PM | AvgTanh |
|---|---|---|---|---|---|---|---|---|---|
| | 21-29 | LTYKEGAPI (SEQ ID NO: 35) | 13786.2 | 1897.6 | 11858 | 2786.3 | 0.9867 | -4.5475 | 0.7234 |
| | 68-76 | DPMYLTFTS (SEQ ID NO: 48) | 19139.2 | 12211.3 | 4676 | 13716.9 | 0.964 | -6.6504 | 0.6432 |
| | 99-107 | SPKVNGENL (SEQ ID NO: 41) | 16209.7 | 8779.6 | 10758 | 16892.2 | 0.9688 | -7.2877 | 0.6411 |
| HLA B*5301 | 15-23 | EPARITLTY (SEQ ID NO: 12) | 64.4 | 132.5 | 16 | 11.6 | 0.9988 | 22.6049 | 0.8709 |
| | 114-122 | LATGSQDFF (SEQ ID NO: 49) | 1316.3 | 435.3 | 8208 | 3083 | 0.9822 | 0.3717 | 0.7594 |
| | 68-76 | DPMYLTFTS (SEQ ID NO: 48) | 6521.6 | 6540 | 1499.6 | 3350.5 | 0.9707 | -2.0248 | 0.7135 |
| HLA B*5401 | 68-76 | DPMYLTFTS (SEQ ID NO: 48) | 1187.7 | 3591.9 | 1422 | 1200.2 | 0.9923 | 5.0207 | 0.7715 |
| | 15-23 | EPARITLTY (SEQ ID NO: 12) | 11348.1 | 4909.2 | 13947 | 1004.6 | 0.9534 | -1.6201 | 0.6938 |
| | 133-141 | LAAGKYTDA (SEQ ID NO: 77) | 4189.1 | 256 | 2969 | 18742.4 | 0.985 | 0.2011 | 0.6846 |
| | 3-11 | LTASTTATA (SEQ ID NO: 9) | 8053.3 | 208.7 | 15208 | 7990.1 | 0.9726 | -1.6094 | 0.6826 |
| | 27-35 | APITIMDNG (SEQ ID NO: 57) | 3514.5 | 941.3 | 2123 | 30694.5 | 0.9767 | -0.4824 | 0.6633 |
| | 114-122 | LATGSQDFF (SEQ ID NO: 49) | 591 | 986.9 | 16054 | 2744.5 | 0.9814 | 9.3313 | 0.7484 |
| HLA B*5701 | 21-29 | LTYKEGAPI (SEQ ID NO: 35) | 3004.6 | 3996.2 | 27279 | 1461.1 | 0.9637 | 2.7728 | 0.7142 |
| | 54-62 | GTTSTSVNF (SEQ ID NO: 32) | 11032.9 | 3347.2 | 2551 | 746.9 | 0.9736 | 6.411 | 0.6923 |
| HLA B*5801 | 114-122 | LATGSQDFF (SEQ ID NO: 49) | 34 | 248 | 759 | 490.4 | 0.9892 | | 0.7752 |
| | 54-62 | GTTSTSVNF (SEQ ID NO: 32) | 1243 | 692.7 | 1347 | 371.7 | 0.9816 | | 0.7332 |
| | 5-13 | ASTTATATL (SEQ ID NO: 36) | 1739 | 1663.3 | 14099 | 1009.3 | 0.9636 | | 0.6952 |
| HLA B*7301 | 1-9 | ADLTASTTA (SEQ ID NO: 55) | 33384.6 | 237.6 | | 30447.1 | 0.85 | | 0.5741 |

TABLE 2

The predicted CD4+ T cell epitopes:

| Position | Peptide | Allele | Positive prediction by the indicated approaches |
|---|---|---|---|
| 101-121 | KVNGENLVGDDVVLATGSQDF (SEQ ID NO: 58) | DRB1_0301 | TEPITOPE, SMM-align, Consensus, PM & AvgTanh |
| 83-101 | QFTTKVIGKDSRDFDISPK (SEQ ID NO: 59) | DRB1_0301 | SMM-align |
| 101-121 | KVNGENLVGDDVVLATGSQDF (SEQ ID NO: 58) | DRB1_0401 | SMM-align, Consensus, and MetaSVMp |
| 68-86 | DPMYLTFTSQDGNNHQFTT (SEQ ID NO: 60) | DRB1_0401 | LA Kernel, SMM-align, Consensus, PM & AvgTanh and MetaSVMp |
| 36-63 | NIDTELLVGTLTLGGYKTGTTSTSVNFT (SEQ ID NO: 61) | DRB1_0401 | SMM-align, Consensus, PM & AvgTanh and MetaSVMp |
| 135-149 | AGKYTDAVTVTVSNQ (SEQ ID NO: 62) | DRB1_0401 | LA Kernel |

TABLE 2-continued

The predicted CD4+ T cell epitopes:

| Position | Peptide | Allele | Positive prediction by the indicated approaches |
|---|---|---|---|
| 36-54 | NIDTELLVGTLTLGGYKTG (SEQ ID NO: 63) | DRB1_0404 | SMM-align, Consensus, PM & AvgTanh and MetaSVMp |
| 68-83 | DPMYLTFTSQDGNNHQ (SEQ ID NO: 64) | DRB1_0404 | LA Kernel, Consensus and PM |
| 64-83 | DAAGDPMYLTFTSQDGNNHQ (SEQ ID NO: 65) | DRB1_0405 | SMM-align, PM & AvgTanh and MetaSVMp |
| 1-18 | ADLTASTTATATLVEPAR (SEQ ID NO: 66) | DRB1_0701 | LA Kernel, SMM-align, Consensus and PM |
| 133-149 | LAAGKYTDAVTVTVSNQ (SEQ ID NO: 67) | DRB1_0701 | LA Kernel and Consensus |
| 47-63 | TLGGYKTGTTSTSVNFT (SEQ ID NO: 68) | DRB1_0701 | SMM-align |
| 115-135 | ATGSQDFFVRSIGSKGGKLAA (SEQ ID NO: 69) | DRB1_0802 | TEPITOPE |
| 17-35 | ARITLTYKEGAPITINIDNG (SEQ ID NO: 70) | DRB1_0901 | SMM-align and MetaSVMp |
| 1-15 | ADLTASTTATATLVE (SEQ ID NO: 71) | DRB1_0901 | Consensus |
| 34-48 | NGNIDTELLVGTLTLGGYKTGT (SEQ ID NO: 72) | DRB1_1302 | LA Kernel and MetaSVMp |
|  | No positive results | DRB1_1101 |  |
| 39-54 | TELLVGTLTLGGYKTG (SEQ ID NO: 73) | DRB1_1501 | SMM-align and MetaSVMp |
| 116-135 | TGSQDFFVRSIGSKGGKLAA (SEQ ID NO: 74) | DRB1_1501 | SMM-align |
| 83-120 | QFTTKVIGKDSRDFDISPKVNGE NLVGDDVVLATGSQD (SEQ ID NO: 75) | DRB3_0101 | LA Kernel, SMM-align, Consensus, PM & AvgTanh and MetaSVMp |
| 33-47 | DNGNIDTELLVGTLT (SEQ ID NO: 76) | DRB3_0101 | LA Kernel |
|  | No positive results | DRB4_0101 |  |
|  | No positive results | DRB5_0101 |  |

Of the fifty-three predicted 9-mer CD8+ T cell epitopes that encompassed 46 human MHC-I alleles (Table 1), four peptides (aa residues: 9-17, 10-18, 11-19 and 13-21) fall in this region; of the 9 peptides predicted to contain CD4+ T cell epitopes (Table 2), only one (aa residues 1-18) belongs to this region. The integrity of these potential linear epitopes may be restored by extending the sequence of the switched strand by up to the aa residue 21, which can be done by duplicating the NH$_2$-terminal residues from 15 to 21 of F1 at the COOH-terminus. A recombinant protein F1mut2 is accordingly constructed (Panel A of FIG. 2) and tested. The F1mut2 behaves in a similar manner as the F1mut1 with respect to over-production and solubility (Panel B of FIG. 2, lanes 12-15), and is also purified as a monomer (data not shown).

Example 3

Construction of Mutated F1-V Immunogens

Figure 3:
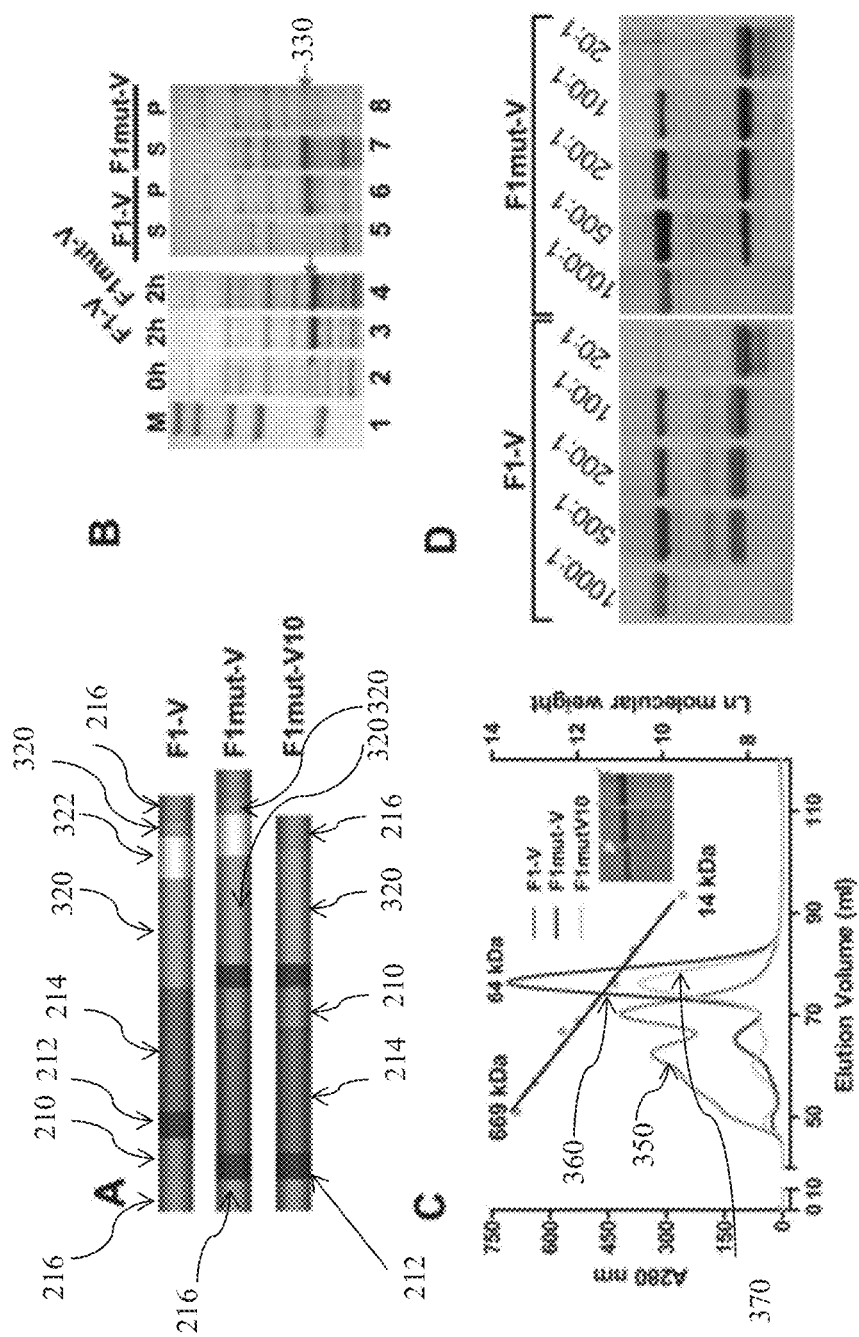
FIG. 3 is an illustration showing construction of mutated F1-V immunogens. Panel A is a set of schematics of construction of recombinant proteins encompassing native F1-V, F1mut-V and F1mut-V10, respectively. Panel B shows the expression and solubility analysis of F1-V constructs using the B-PER reagent. Panel C is a graph showing the purification of F1-V, F1mut-V and F1mut-V10 by HISTRAP column chromatography followed by Hi-load 16/60 SUPERDEX 200 gel filtration. Panel D is a set of images showing the stability of F1-V and F1mut-V proteins tested by treatment with increasing amounts of trypsin at room temperature overnight.

Panel A of FIG. 3 shows a set of schematics of construction of recombinant proteins encompassing native F1-V, F1mut-V and F1mut-V10, respectively. Native fusion protein F1-V is constructed by fusing native F1 to the NH$_2$-terminus of native V. Shade 320 represents the coding sequence of V antigen. Shade 322 represents the coding sequence of putative immunomodulatory sequence that is a part of the coding sequence of V antigen. Rest of the shades represent the same as shown in FIG. 2, wherein shade 210 shows a coding sequence of a donor β-strand of F1, shade 212 shows a coding sequence of a T cell epitope region, shade 214 shows a rest of the F1 coding sequence, and shade 216 shows a hexa-histidine tag of SEQ ID NO: 2.

Fusion of F1mut2 to V can generate a bivalent plague vaccine. Consequently, in this example, a mutated F1-V fusion protein (F1mut-V) is produced by fusing F1mut2 to the NH$_2$-terminus of V with a two amino acid linker (Ser-Ala) in between and the solubility of the fusion protein F1mut-V is compared to that of the native polymeric F1-V.

The *Y. pestis* V antigen is reported to induce interleukin (IL)-10 and suppress the production of pro-inflammatory cytokines such as interferon (IFN)-γ and tumor necrosis factor (TNF)-α, which may lead to lowering of innate immunity in vaccinated individuals.[41] A truncated V in which the COOH-terminal 30 aa residues (271-300) are deleted (referred to as "V10" mutation) is reported to lack this immunomodulatory function.[41] A mutated F1mut-V10 recombinant is therefore constructed by deleting these residues (Panel A of FIG. 3).

Expression and solubility analysis of F1-V constructs are performed using the B-PER reagent. The samples of lysates are analyzed by SDS-PAGE and Coomassie Blue staining (Panel B of FIG. 3). The positions of the F1-V protein bands are marked with arrows 330. "S" represents soluble fraction (supernatant from 12,000 g centrifugation of the lysate), "P" represents insoluble fraction (pellet), and "M" represents molecular weight standards. See Materials and Methods described above for additional details.

F1-V, F1mut-V and F1mut-V10 are expressed in *E. coli* and purified by HISTRAP column chromatography followed by Hi-load 16/60 SUPERDEX 200 gel filtration. A calibration graph in Panel C of FIG. 3 is generated by passing various molecular weight standards through the same column [Thyroglobulin (669 kDa), Ferritin (440 kDa), Catalase (232 kDa), aldolase (158 kDa), Ovalbumin (43 kDa), RNase A (14 kDa), and Albumin (67 kDa)]. The insert in Panel C of FIG. 3 shows the purity of F1-V, F1mut-V, and F1mut-V10 proteins following SDS-PAGE and Coomassie Blue staining of the peak fractions, wherein shade 350 represents eluted protein F1-V, shade 360 represents eluted protein F1mut-V, and shade 370 represents eluted protein F1mut-V10.

The native F1-V, as reported previously,[20,22] is insoluble and partitioned into inclusion bodies (lanes 5 and 6 of Panel B of FIG. 3). Denaturation and refolding solubilized some of the protein but the protein is also eluted, as is reported previously,[20] over a wide range of high molecular weight sizes in a gel filtration column (shade 350 in Panel C of FIG. 3). F1mut-V protein, on the other hand, is nearly approximately 100% soluble (lanes 7 and 8 of Panel B of FIG. 3) and eluted as a symmetrical peak corresponding to a molecular weight of approximately 64 kDa, equivalent to the mass of monomeric F1mut-V fusion protein (shade 360 of Panel C of FIG. 3). The yield of F1mut-V is quite high, approximately 20 mg pure protein per liter of the *E. coli* culture. The mutant protein F1mut-V10 is also highly soluble and may be purified as a monomer (shade 370 in Panel C of FIG. 3).

Stability of F1-V and F1mut-V proteins is tested by treatment with increasing amounts of trypsin at room temperature overnight. In Panel D of FIG. 3, the ratios shown above the gel correspond to the ratios of F1-V or F1mut-V proteins to trypsin (wt:wt). As shown in the image of Coomassie Blue stained SDS-PAGE (15%) gel in Panel D of FIG. 3, stability of F1mut-V protein to trypsin digestion is similar to that of the native F1-V protein.

Example 4

Designing an Oligomerization Deficient YscF Mutant

Inclusion of YscF might expand the breadth of efficacy of F1-V plague vaccine formulation to *Y. pestis* strains containing variant V antigens,[26] or of those strains devoid of capsule but highly virulent in nature.[24,25] Since YscF is a structural component of the injectisome of *Y. pestis*, over-production of this protein caused aggregation.[42] In this example, a mutant YscF is constructed by mutating the aa residues Asn35 and Ile67, that are involved in oligomerization (Asn35 changed to Ser, and Ile67 changed to Thr) (see Panel A of FIG. 4).[43]

Figure 4:
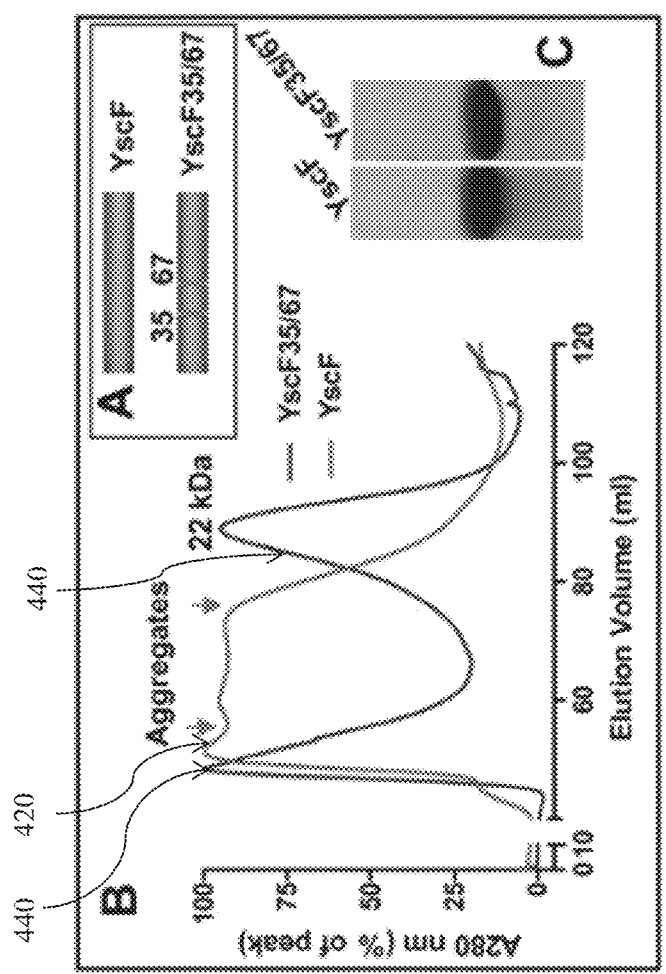
FIG. 4 is an illustration showing an oligomerization deficient YscF mutant. Panel A is a schematic of native YscF and YscF35/67 mutants. Panel B shows the purification of YscF and YscF35/67 mutant proteins. Panel C shows the purity of YscF and YscF35/67 proteins as analyzed by SDS-PAGE and Coomassie blue staining of the peak fractions.

YscF and YscF35/67 mutant proteins are purified (Panel B of FIG. 4). Purity of YscF and YscF35/67 proteins are analyzed by SDS-PAGE and Coomassie Blue staining of the peak fractions (Panel C of FIG. 4). The gel filtration profiles in Panel B of FIG. 4 shows that the native YscF 420 is eluted as a broad peak spanning the entire high molecular weight range, which is consistent with the formation of heterodisperse aggregates, while the YscF35/67 mutant protein 440 is eluted as two peaks, one as a high molecular weight aggregating near the void volume, and a second peak corresponding to a molecular mass of approximately 22 kDa, which is equivalent to a dimer. This result indicates that YscF35/67 mutant protein is soluble. The mutant dimer does, however, show slow aggregation during concentration and storage, as evident by the appearance of small amounts of precipitates.

Example 5

Decorating the Phage T4 Nanoparticle with F1 and V Antigens

In this example, a large number of F1, V, F1-V, and YscF recombinant proteins, both in native and mutated forms, are fused to the $NH_2$- and/or the COOH-termini of either a phage T4 Soc or a T4-related phage RB69 Soc and screened for their solubility as well as ability to bind to T4 phage nanoparticles.

Figure 5:
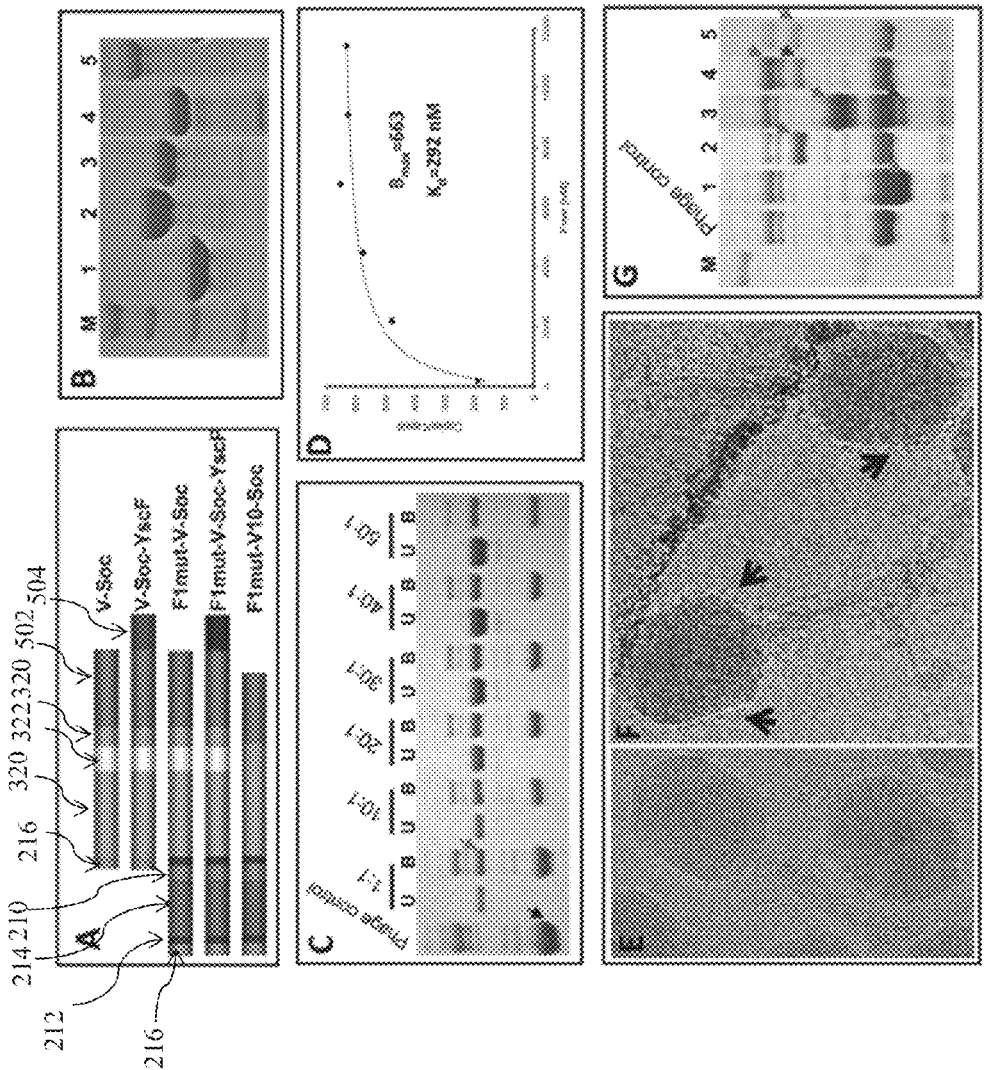
FIG. 5 illustrates the engineering of F1, V, and YscF antigens and a display of F1mut-V-Soc on a phage T4 nanoparticle. Panel A is a schematic of Soc-fusions. Panel B shows the purification of the over-expressed Soc fusion proteins shown in panel A. Panel C shows a display of a fusion protein F1mut-V-Soc on phage T4 nanoparticles. Panel D shows saturation binding curve of F1mut-V-Soc. Panel E is an image showing a cryo-electron micrograph of wild-type control phage T4. Panel F is an image showing a cryo-electron micrograph of phage T4 decorated with F1mut-V. Panel G shows various Soc fusion proteins displayed on phage T4 for immunizations.

Panel A of FIG. 5 is a schematic of Soc-fusions. Shade 502 represents Soc and shade 504 represents YscF. The rest of the shades represent the same as shown in FIG. 2 and FIG. 3, wherein shade 210 shows a coding sequence of a donor β-strand of F1, shade 212 shows a coding sequence of a T cell epitope region, shade 214 shows a rest of the F1 coding sequence, and shade 216 shows a hexa-histidine tag of SEQ ID NO: 2, shade 320 represents the coding sequence of V antigen, and shade 322 represents the coding sequence of putative immunomodulatory sequence that is a part of the coding sequence of V antigen.

As shown in Panel A of FIG. 5, recombinant protein V-Soc is produced by fusing V to the $NH_2$-terminus of Soc, recombinant protein V-Soc-YscF is produced by fusing V to the $NH_2$-terminus of Soc and fusing YscF to the COOH-terminus of Soc, recombinant protein F1mut-V-Soc is produced by fusing recombinant protein F1mut-V to the $NH_2$-terminus of Soc, recombinant protein F1mut-V-Soc-YscF is produced by fusing YscF to the COOH-terminus of recombinant protein F1mut-V-Soc, and recombinant protein F1mut-V10-Soc is produced by fusing recombinant protein F1mut-V10 to the $NH_2$-terminus of Soc.

The Soc fusion proteins in panel A are over-expressed and purified as described above in Materials and Methods. The purity of the proteins is evaluated by SDS-PAGE and Coomassie Blue staining (see Panel B of FIG. 5). Lane M corresponds to molecular weight standards. Lane 1 corresponds to recombinant protein V-Soc. Lane 2 corresponds to recombinant protein F1mut-V-Soc. Lane 3 corresponds to recombinant protein F1mut-V10-Soc. Lane 4 corresponds to recombinant protein V-Soc-YscF. Lane 5 corresponds to recombinant protein F1mut-V-Soc-YscF.

Panel C of FIG. 5 shows a display of a fusion protein F1mut-V-Soc on phage T4 nanoparticles. Approximately $3 \times 10^{10}$ Hoc⁻Soc⁻ phage particles are incubated at the indicated ratios of F1mut-V-Soc molecules to capsid binding sites and display is carried out as described above in Materials and Methods. The ratios of F1mut-V-Soc molecules to capsid binding sites are labeled above each lane of the SDA-Page gel. U and B represent the unbound and phage-bound fractions. The lane of Phage control is a control experiment wherein Hoc⁻ Soc⁻ phage is used. The position of gp23* band 542 is labeled with a dark arrow. F1mut-V-Soc bands pointed by a gray arrow present in bound lanes but do not present in phage control lane.

Saturation binding curve of F1mut-V-Soc is shown in Panel D of FIG. 5. The density volumes of bound and unbound proteins from SDS-PAGE (Panel C of FIG. 5) are determined by laser densitometry and normalized to that of gp23* present in the respective lane. The copy numbers are determined in reference to gp23* (930 copies per capsid). The data are plotted as one site saturation ligand binding curve and fitted by non-linear regression using the SIGMAPLOT 10.0 software and the calculated binding parameters are shown. "Kd" refers to apparent binding constant. "Bmax" refers to maximum copy number per phage nanoparticle.

Image in Panel E of FIG. 5 shows a cryo-electron micrograph of wild-type control phage T4. Image in Panel F of FIG. 5 shows a cryo-electron micrograph of phage T4 decorated with F1mut-V. Arrows point to a layer of fuzzy projections around the perimeter of the capsid in the F1mut-V decorated phage nanoparticles.

In this example, a series of nanoparticle decorated plague immunogens are prepared, including all three plague immunogens displayed on the same capsid using the F1mut-V-Soc-YscF35/67 fusion protein (Panel G of FIG. 5, lane 4). Various Soc fusion proteins are further displayed on phage T4 for immunizations (see Panel G of FIG. 5). In Panel G of FIG. 5, "M" refers to molecular weight standards, "Phage control" means that Hoc⁻ Soc⁻ phage nanoparticles are used in the experiment. The numbers above the SDS-PAGE correspond to various Soc fusion proteins used in the experiment, respectively, wherein "1" corresponds to V-Soc, "2" corresponds to F1mut-V-Soc, "3" corresponds to V-Soc-YscF, "4" corresponds to F1mut-V-Soc-YscF, and "5" corresponds to F1mut-V10-Soc. Gray arrows show the positions of various displayed protein bands. Presence of a second fainter and shorter band in lanes 3 and 4 pointed by dark arrows indicate that some of the C-terminally fused YscF is cleaved off by nonspecific proteolysis.

Disclosed embodiments show that the RB69 Soc binds to T4 capsid at nearly the same affinity as T4 Soc.[34] The RB69 Soc-fused plague antigens, with the exception of the native F1-Soc, produce soluble proteins whereas the T4 Soc-fused antigens are insoluble. Several of phage RB69 immunogens are purified (see Panel B of FIG. 5) and tested for binding to T4 using the disclosed previously established in vitro assembly system. A result shown in Panel C and D of FIG. 5 exemplifies the versatility of the T4 nanoparticle display. Consistent with the crystal structure of Soc, which showed that both the $NH_2$- and COOH-termini are exposed on the capsid surface, the plague immunogens F1mut and V could be efficiently displayed as an F1mut-V fusion protein that in turn is fused to the $NH_2$-terminus of Soc (Panel C of FIG. 5). At the same time, its COOH-terminus could be fused to YscF35/67, and the resultant F1mut-V-Soc-YscF35/67 fusion protein containing all three plague immunogens could be displayed on T4 capsid (see Panel G of FIG. 5, lane 4).

The 66 kDa F1mut-V-Soc bound to T4 even at a relatively low 1:1 ratio of F1mut-V-Soc molecules to Soc binding sites (Panel C of FIG. 5, gray arrow). Binding of the F1mut-V-Soc to T4 increased with increasing ratio of the 66 kDa F1mut-V-Soc to T4 and reached saturation at a ration approximately from 20:1 to 30:1. The copy number of bound F1mut-V-Soc per capsid (Bmax) is 663, which meant that approximately 76% of the Soc binding sites are occupied, and its apparent binding affinity (Kd) is 292 nM, which is approximately 4-fold lower than that of Soc binding ($K_d$=75 nM) (Panel D of FIG. 5).[34] This is consistent with the expectation that the 66 kDa F1mut-V-Soc, unlike the 10 kDa Soc, would encounter steric constraints to occupy all the binding sites on the capsid exterior. Given this limitation, the observed copy number is remarkably high, with the capsid surface presumably tightly packed with the F1mut-V molecules, as a model shown in Panel F of FIG. 1, and exposing, consequently, the plague antigen epitopes for presentation to the immune system. Indeed, cryo-electron microscopy showed that these T4 capsids, unlike the wild-type capsids (Panel E of FIG. 5), are decorated with a layer of F1mut-V molecules, seen as fuzzy protrusions around the perimeter of the capsid wall (Panel F of FIG. 5).

Example 6

The Mutated F1-V Monomer Induced Robust Immunogenicity and Protective Efficacy

In this example, the immunogenicity and protective efficacy of F1mut-V and other plague immunogens are evaluated in a mouse model. Balb/c mice, twelve per group, are vaccinated with various plague antigens adjuvanted with alhydrogel as shown in Panel A of FIG. 6. Immunization scheme is shown in Panel B of FIG. 6. Antigen-specific antibody (IgG) titers in the sera are determined by ELISA, using purified V (Chart I of Panel C of FIG. 6), F1mut2 (Chart II of Panel C of FIG. 6), or YscF35/67 (Chart III of Panel C of FIG. 6) as the coating antigen. No significant cross-reactivity is observed between the antibodies produced against one plague antigen versus a different plague antigen that is coated on the ELISA plate. Error bars represent S.D. "***" in Panel C of FIG. 6 denotes p<0.001 (ANOVA).

Figure 6:
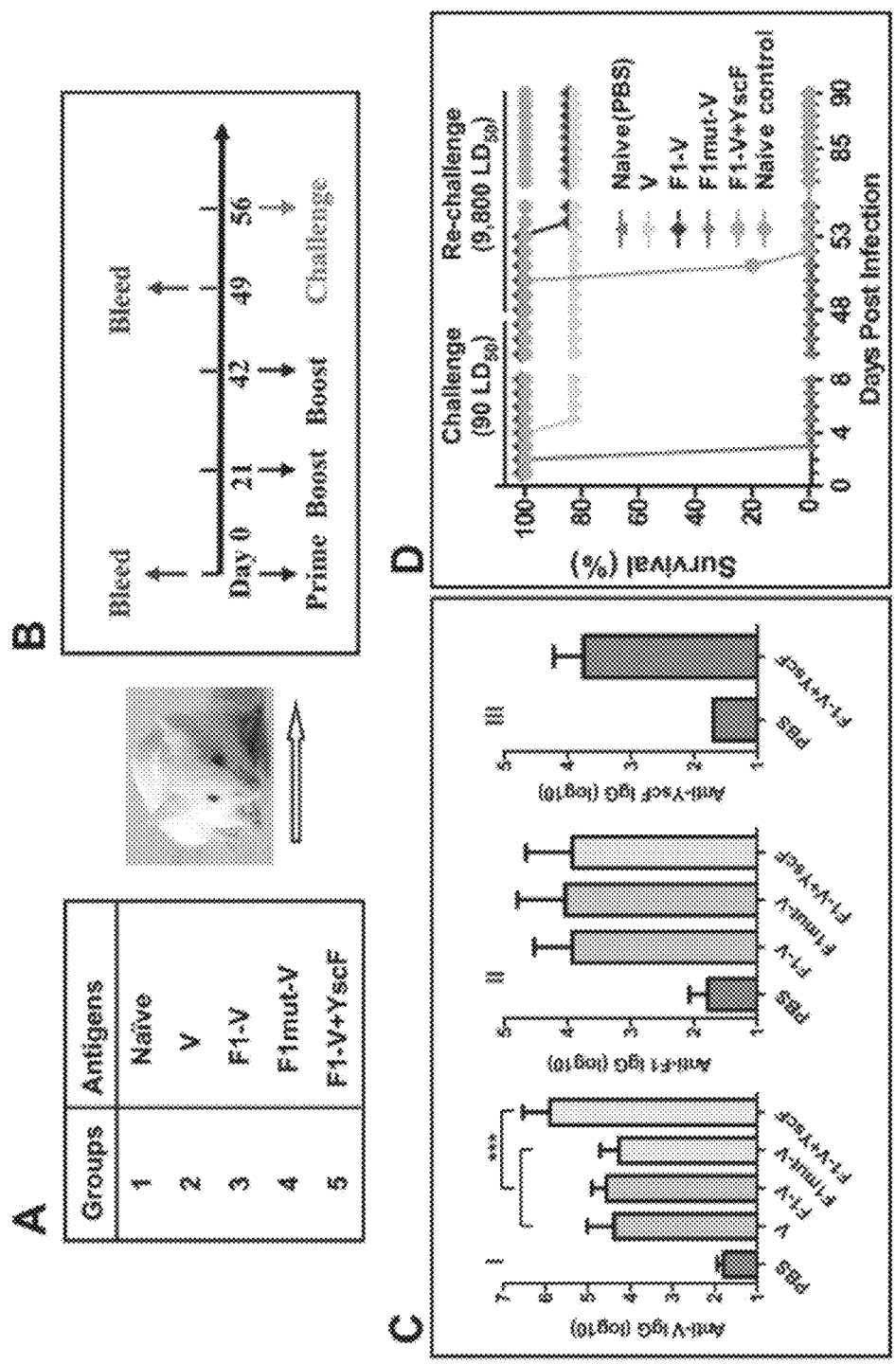
FIG. 6 is a set of graphs showing that soluble monomeric F1 mutant protein elicits robust antibody titers and provides complete protection in a mouse model of pneumonic plague. Panel A shows that Balb/c mice, twelve per group, are vaccinated with various plague antigens adjuvanted with alhydrogel. Panel B shows the immunization scheme. Panel C is a set of graphs of antigen-specific antibody (IgG) titers in the sera determined by ELISA, using purified V (Chart I), F1mut2 (Chart II), or YscF35/67 (Chart III) as the coating antigen. Panel D shows the survival of immunized mice against intranasal challenge with 90 $LD_{50}$ of *Y. pestis* CO92 and the survived mice being re-challenged with 9,800 $LD_{50}$ at day-48 post-first challenge.

The data shows that all the three plague antigens adjuvanted with alhydrogel induce antigen-specific antibodies (Panel C of FIG. 6). The V antigen induced the highest titers with the end point titer reaching as high as approximately $7 \times 10^6$. The YscF antigen is the least immunogenic (Chart III of Panel C of FIG. 6), with the endpoint titers about approximately 1-2 orders of magnitude lower than that of F1 and V antigens (Chart I and Chart II of Panel C of FIG. 6). No significant differences in F1-specific antibody titers are observed among the various groups (i.e., F1-V versus F1mut-V versus F1-V+YscF) (see Chart II of Panel C of FIG. 6). Importantly, the monomeric F1mut-V induced comparable antibody titers as the native polymeric F1-V, suggesting that the capsular structure of F1 per se does not afford a significant advantage to induction of antibodies. However, unexpectedly, the V-specific IgG titers are at least an order of magnitude higher when YscF is also included in the vaccine (p<0.001) (Chart I of Panel C of FIG. 6; compare F1-V to F1-V+YscF).

Intranasal challenge of animals with 90 $LD_{50}$ of Y. pestis CO92 [1 $LD_{50}$=100 colony forming units (CFU) in Balb/c mice], one of the most lethal strains, shows that all the control mice died by day 3. However, the mice immunized with native V immunogen shows approximately 83% survival (two of twelve mice died), whereas the mice immunized with F1-V, F1mut-V, or F1-V plus YscF are approximately 100% protected (see Panel D of FIG. 6).

The survived mice are re-challenged with a higher dose, 9,800 $LD_{50}$, of Y. pestis CO92 on day-48 post-first challenge. The purpose of re-challenge is to determine if a strong adaptive immunity is generated after first infection with Y. pestis, which should in turn confer a much higher level of protection against subsequent challenges. Indeed, disclosed data shows that all of the mice survived the re-challenge except two mice in the native F1-V group that succumbed to infection (approximately 83% protection) (Panel D of FIG. 6). All of the naïve animals of same age which are used as a re-challenge control died as expected. These efficacy results show that the monomeric F1mut-V is as efficacious as or even slightly better than the native F1-V polymer. The soluble monomeric F1 mutant protein elicits robust antibody titers and provides complete protection in a mouse model of pneumonic plague. In this example, the animal mortality data is analyzed by Kaplan Meier's survival estimates and a p value of approximately 0.05 or less is considered significant.

Example 7

The T4 Nanoparticle Arrayed Antigens Provided Complete Protection Against *Y. pestis*

Pneumonic Challenge

Figure 7:
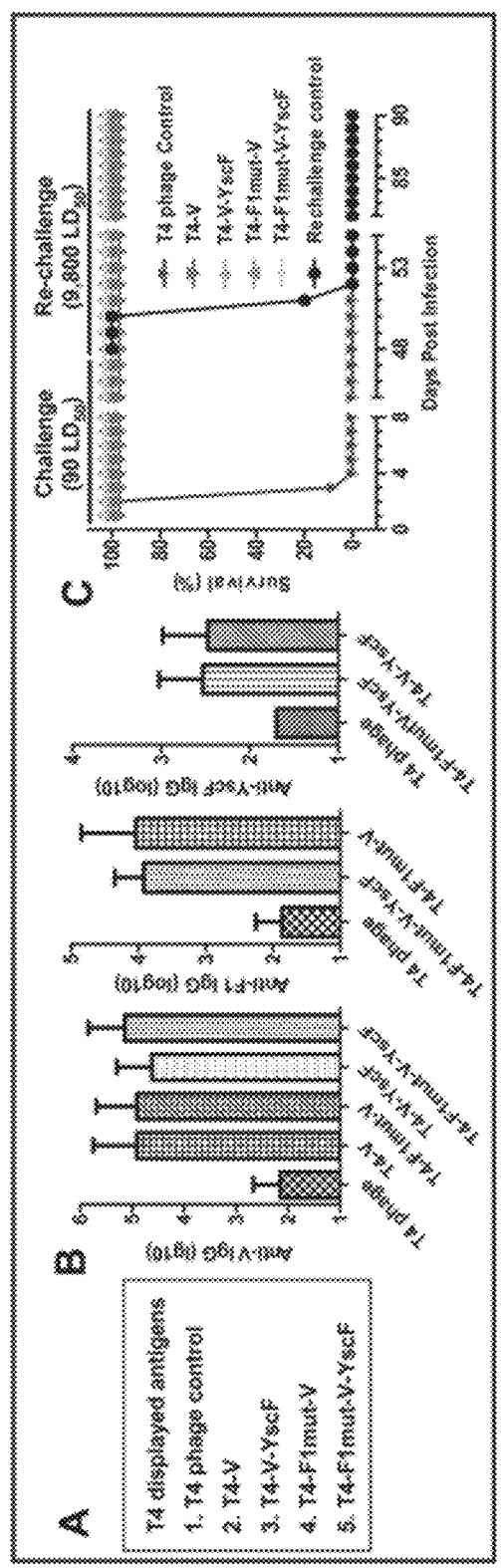
FIG. 7 is a set of graphs showing that T4 nanoparticle displayed plague immunogens induce robust immunogenicity and protective efficacy against pneumonic plague. Panel A shows the T4 displayed plague immunogen groups, wherein there are twelve mice per group. Panel B is a set of graphs showing antigen-specific antibody (IgG) titers being determined by ELISA. Panel C is a graph showing survival of vaccinated mice against intranasal challenge with 90 $LD_{50}$ of *Y. pestis* CO92. The survived mice are re-challenged with approximatley 9,800 $LD_{50}$ at day-48 post-first challenge.

The immunogenicity of nanoparticle decorated plague antigens is tested by vaccinating mice with phage T4 particles. The immunogenicity and protective efficacy of T4 displayed plague immunogens are evaluated in a mouse model using the same immunization scheme as described and shown in Panel B of FIG. 6. Panel A of FIG. 7 shows the T4 displayed plague immunogen groups, wherein there are twelve mice per group. The Soc-fused plague immunogens are displayed on T4 phage particles and the amount of the antigen is kept the same as that of the soluble preparations shown in FIG. 6. However, the T4 nanoparticle displayed immunogens are directly used for vaccination without any adjuvant. Antigen-specific antibody (IgG) titers are determined by ELISA (Panel B of FIG. 7). The data shows that the T4 displayed plague antigens induce comparable antibody titers as the adjuvanted soluble antigens (Panel B of FIG. 7).

The data In Panel C of FIG. 7 shows survival of vaccinated mice against intranasal challenge with 90 $LD_{50}$ of *Y. pestis* CO92. The survived mice are re-challenged with approximatley 9,800 $LD_{50}$ at day-48 post-first challenge. The animal mortality data is analyzed by Kaplan Meier's survival estimates and a p value of 0.05 or less is considered significant.

The challenge data shows that all the T4 decorated plague antigens, including the V alone group, provided approximately 100% protection to mice against intranasal challenge with 90 $LD_{50}$ of *Y. pestis* CO92; all the control animals died by day 4. Upon re-challenge on day 48 post-first challenge with 9,800 $LD_{50}$, all of the mice are completely protected (see Panel C of FIG. 7). As expected, the control re-challenge group of mice succumbed to infection. Overall, these data suggested that the T4 nanoparticle arrayed plague antigens might be more potent than the soluble antigens, as two deaths in each of the V and F1-V groups of mice occurred with the soluble vaccines (see Panel D of FIG. 6) but not with the T4 vaccines.

This example demonstrates that the T4 nanoparticle displayed plague immunogens induced robust immunogenicity and protective efficacy against pneumonic plague.

Example 8

The T4 Nanoparticle Antigens Induced Balanced $T_H1$ and $T_H2$ Immune Response

Stimulation of both arms of the immune system, humoral ($T_H2$) and cellular ($T_H1$), is probably essential for protection against *Y. pestis* infection.[6,23,44,45] In mice, the $T_H1$ profile involves induction of antibodies belonging to IgG2a subclass whereas the $T_H2$ profile primarily involves the induction of IgG1 subclass. To determine the specificity of antibodies induced by soluble vs T4 displayed antigens, the subclass IgG titers are determined by ELISA (see FIG. 8). The immunization scheme adopted in this example is the same as that described and shown in Panel B of FIG. 6. Seven days after the second boost, sera are collected and IgG1 and IgG2a titers are determined by ELISA. F1mut-V is used as the coating antigen, since it covers all the epitopes present in both F1mut-V and F1mut-V10.

Figure 8:
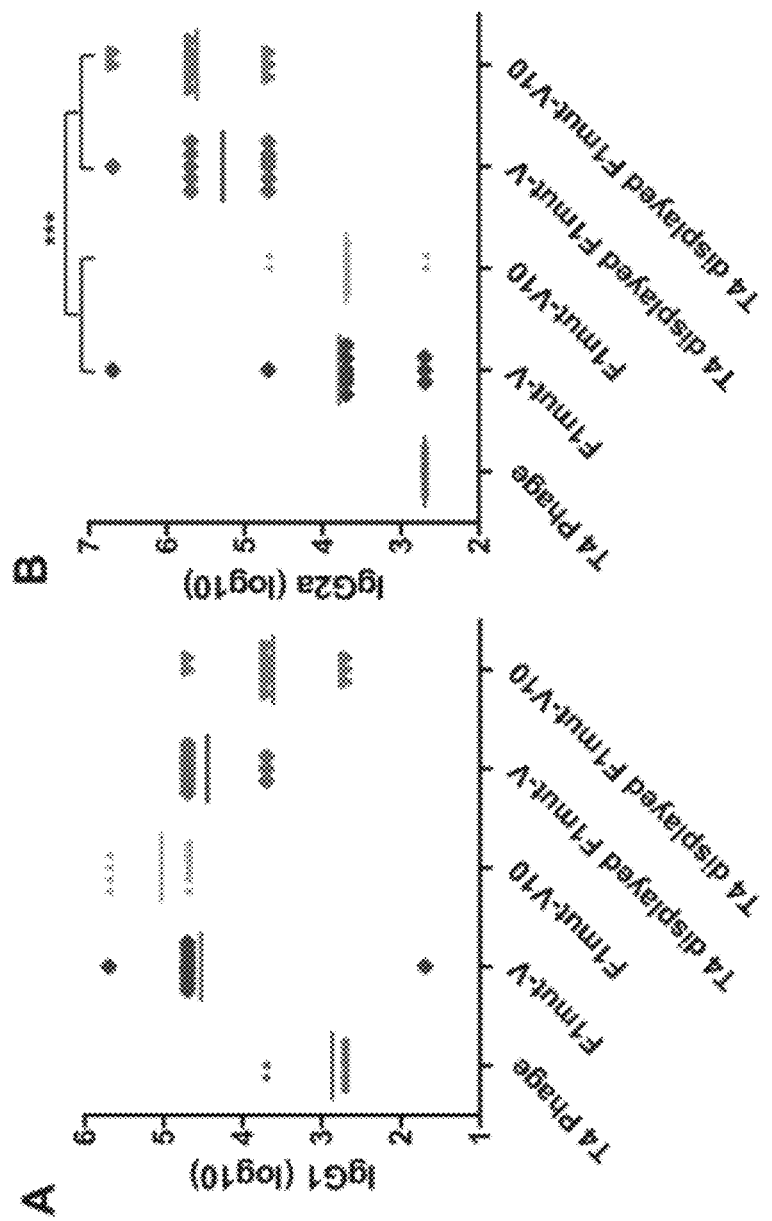
FIG. 8 is a set of plot graphs illustrating that T4 displayed plague immunogens generate balanced TH1 (IgG1) and TH2 (IgG2a) responses. Panel A is an image showing determining IgG1 titers seven days after the second boost of immunization as shown in Panel B of FIG. 6. Panel B is an image showing determining IgG2a titers seven days after the second boost of immunization as shown in Panel B of FIG. 6.

FIG. 8 shows that the T4 displayed plague immunogens generated balanced $T_H1$ (IgG1) and $T_H2$ (IgG2a) responses. Data shows that the soluble antigens and the T4 displayed antigens induced comparable IgG1 titers ($T_H2$ response) (Panel A of FIG. 8) whereas the T4 antigens evoked 1-2 orders of magnitude higher IgG2a titers than the soluble antigens ($T_H1$ response) (Panel B of FIG. 8). These results suggest that the T4 decorated plague immunogens stimulated stronger cellular responses as well as humoral responses, whereas the soluble antigens showed a bias towards the humoral responses as is observed in the previous studies.[46]

Note that the sera of the control T4 phage-immunized mice show higher background. This is because T4 phage nanoparticles, as demonstrated in previous studies, induces a strong antibody response to its components. Consequently, the sera from T4 phage-immunized mice will have increased amounts of IgGs compared to the pre-immune sera, giving more non-specific background at low dilutions of the sera. Data shown are the antibody titers of 12 mice in each group with S.D. (error bars). "*": p<0.05; "***": p<0.001 (ANOVA).

Example 9

F1mut-V and F1mut-V10 Showed Similar Immunogenicity and Protective Efficacy Profiles The immunogenicity and protective efficacy of F1mut-V vs F1mut-V10 is evaluated by three criteria: F1- and V-specific antibody titers, cytokine responses, and protection against *Y. pestis* CO92 challenge. The immunogenicity and protective efficacy of F1mut-V and F1mut-V10 are compared both as adjuvanted soluble antigens or adjuvant-free T4 nanoparticle decorated antigens.

Figure 9:
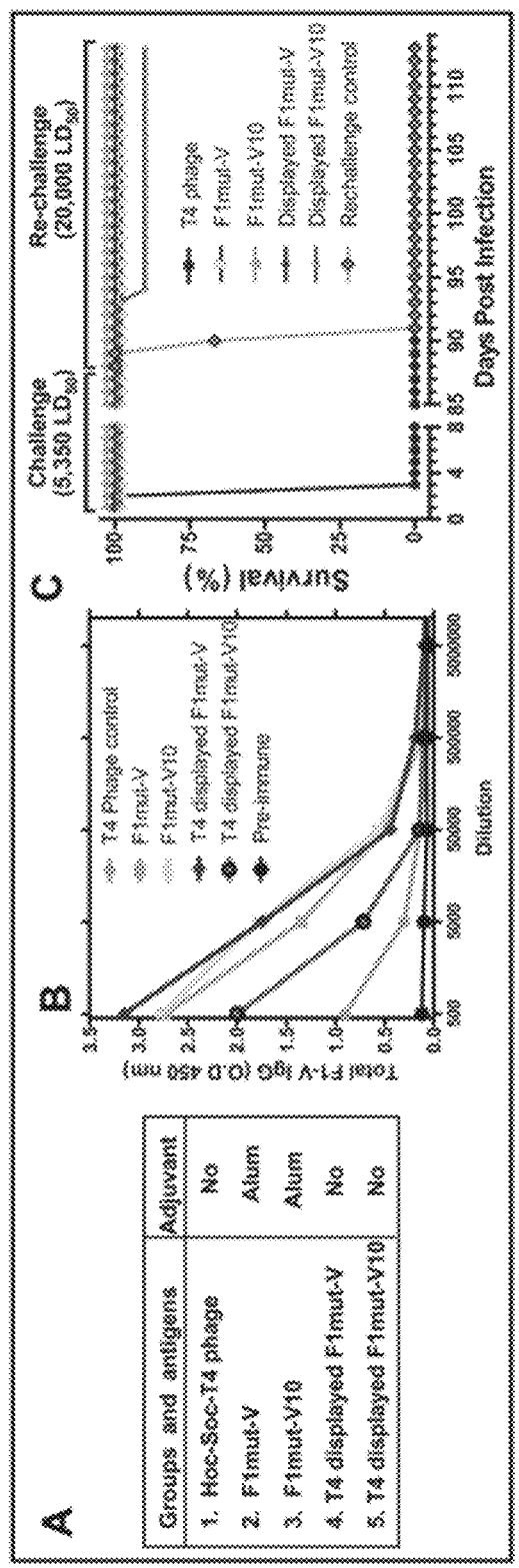
FIG. 9 is a set of plot graphs illustrating that F1mut-V and F1mut-V10 mutants show comparable immunogenicity and protection against pneumonic plague. The immunogenicity and protective efficacy of F1mut-V and F1mut-V10 were compared both as adjuvanted soluble antigens or adjuvant-free T4 nanoparticle decorated antigens. Panel A of FIG. 9 is a table showing the vaccine formulations used in the study, eight mice per group. Panel B of FIG. 9 is a graph showing total F1-V specific antibody titers as determined by ELISA. Panel C of FIG. 9 is a graph showing survival of vaccinated mice against intranasal challenge with 5,350 LD50 of $Y.$ $pestis$ CO92.

The vaccine formulations used in the study, eight mice per group, are shown in Panel A of FIG. 9. Total F1-V specific antibody titers are determined by ELISA (see Panel B of FIG. 9). Note that the sera of the control T4 phage-immunized mice show higher background than the pre-immune sera, probably because T4 phage induces a strong antibody response to its components which raises the levels of the IgGs in the sera and gives more non-specific background at low dilutions.

Panel C of FIG. 9 shows survival of vaccinated mice against intranasal challenge with 5,350 $LD_{50}$ of *Y. pestis* CO92. The survived mice are re-challenged with 20,000 $LD_{50}$ at day-88 post-first challenge. The animal mortality data is analyzed by Kaplan Meier's survival estimates and a p value of 0.05 or less is considered significant. F1mut-V and F1mut-V10 mutants show comparable immunogenicity and protection against pneumonic plague.

Seven days after the second boost (day-49), mice (5 per group) are sacrificed and spleens are harvested. The splenocytes are cultured and stimulated by purified F1-V protein. Cytokines levels are determined as described in Materials and Methods.

Figure 10:
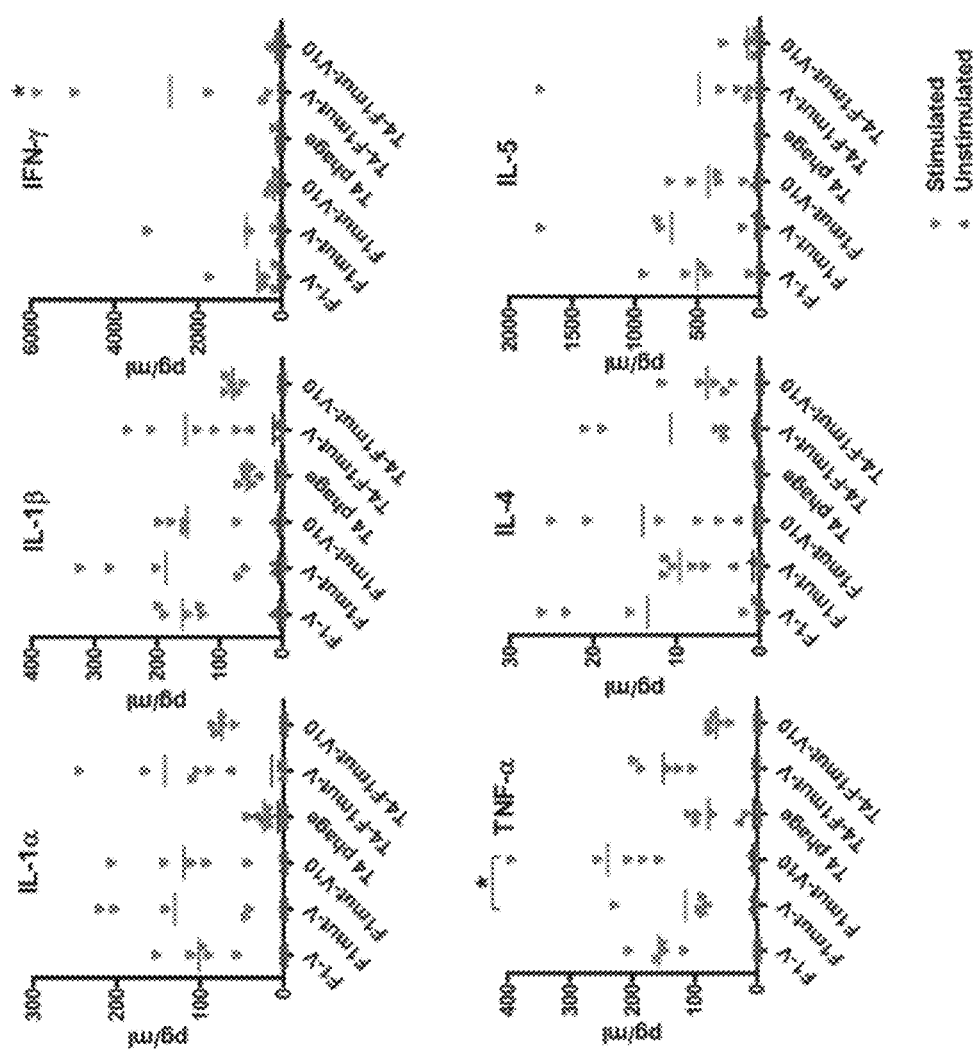
FIG. 10 is a set of plot graphs illustrating the induction of proinflammatory cytokines by F1mut-V and F1mut-V10 immunogens.

Both the F1- and V-specific IgG antibodies (see Panel B of FIG. 9) and subclass IgG titers (Panel A and Panel B of FIG. 8) are not significantly different between the F1mut-V and F1mut-V10 immunized groups of mice when the immunogen used is soluble and alhydrogel-adjuvanted. However, when decorated on phage T4 nanoparticle with no adjuvant, F1mutV elicited higher total IgG (see Panel B of FIG. 9) and IgG1 titers (see Panel A of FIG. 8) than F1mutV10 (p<0.05). These trends are also reflected in the production of the TH2 cytokines, IL-4 and IL-5, by splenocytes of immunized mice stimulated ex vivo with F1-V. Similar levels of IL-4 and IL-5 are produced by the soluble F1mut-V and F1mut-V10 antigens or the T4-displayed F1mut-V, whereas the T4 displayed F1mut-V10 showed slightly reduced levels (FIG. 10). The induction of proinflammatory cytokines, such as IL-1α and IL-1β is also similar, irrespective of whether the antigens are soluble or T4 displayed (FIG. 10). However the levels of TNF-α, an inflammatory mediator that synergistically acts with IFN-γ to help bridge the gap between innate and cell-mediated immune responses, are significantly higher in mice immunized with soluble F1mut-V10 than those immunized with F1mut-V (FIG. 10). However, the trend is opposite when F1mut-V and F1mut-V10 immunogens are T4 displayed, although the data does not reach statistical significance. In fact, the T4 displayed F1mut-V10 induce overall weaker IFN-γ and cytokine responses when compared to its F1mut-V counterpart.

With respect to animal survival, both the F1mut-V and F1mut-V10 immunogens, either soluble or T4 displayed, provided approximately 100% protection to mice upon intranasal challenge with 5,350 $LD_{50}$ of $Y.$ $pestis$ CO92 (see Panel C of FIG. 9), with the control animals dying by day 3. When the mice are re-challenged with an extremely high $LD_{50}$ (20,000) on day 88 post-first challenge, all the groups showed approximately 100% protection except the T4-displayed F1mut-V10 group in which one mouse died (approximately 92% protection) (see Panel C of FIG. 9). All of the naïve re-challenge control animals died by day 4.

Example 10

The Mutated and T4 Displayed Plague Antigens Provided Approximately 100% Protection Against Pneumonic Plague in a Brown Norway Rat Model To further test the efficacy of the mutated immunogens, a study on Brown Norway rat model of pneumonic plague is conducted. Rats,[47] the natural host of $Y.$ $pestis$, are vaccinated with alhydrogel adjuvanted F1mut-V, and F1mut-V10 as well as the T4 nanoparticle displayed F1mut-V and F1mut-V10 (Panel A of FIG. 11). Vaccine formulations used in various groups, twelve rats per group, are shown in Panel A of FIG. 11. The same immunization scheme as shown in Panel B of FIG. 6 is used and the animals are challenged with a 5,000 $LD_{50}$ of $Y.$ $pestis$ CO92. The soluble antigens (groups 2-4) are adjuvanted with alhydrogel. The T4 displayed groups contained no adjuvant. (B) Survival of vaccinated rats against intranasal challenge with 5,000 $LD_{50}$ of $Y.$ $pestis$ CO92. The animal mortality data is analyzed by Kaplan Meier's survival estimates and a p value of 0.05 or less is considered significant. The data showed that all the control animals died by day 4 whereas all the F1mut-V and F1 mut-V10 immunized animals are approximately 100% protected (Panel B of FIG. 11). Therefore, the mutated and T4 displayed plague antigens provided complete protection against $Y.$ $pestis$ CO92 in a Brown Norway rat model of pneumonic plague.
Discussion This present invention proposes three hypotheses to design a soluble monomeric plague vaccine, yet retaining its structural and epitope integrity. First, disclosed embodiments hypothesize that the β-strand that connects the adjacent F1 subunits requires repositioning. This is achieved by transplanting the $NH_2$-terminal β-strand to the COOH-terminus in such a way that the reoriented β-strand fits into its own β-sheet cleft rather than that of the adjacent F1 subunit. It also eliminated the need for chaperone and usher mediated oligomerization as there would no longer be an unfilled β-sheet pocket exposed in the F1 subunit. Second, by using epitope predictions, the $NH_2$-terminal aa residues 15-21 of F1 flanking the β-strand are duplicated at the COOH-terminal end of F1 to restore any potential T-cell epitopes that might have been lost during the switch. This is important, because, in a previous study, a simple β-strand switch produced a less stable monomer with diminished immunogenicity.[48] Third, the mutated F1 is fused to the $NH_2$-terminus of V with a flexible linker in between to minimize interference between the F1 and V domains. The bivalent F1mut-V immunogen thus produced shows a remarkable shift in solubility, from an insoluble F1-V polymer to a completely soluble monomer (FIG. 3). The monomer may be purified from cell-free lysates at high yields, approximately 20 mg of pure protein from a liter of $E.$ $coli$ culture, which, in some disclosed embodiments, may be substantially increased under optimized conditions in a fermentor.

Several lines of evidence demonstrate that the F1mut-V monomer is as efficacious as, if not better than, the native F1-V polymer. In four separate immunization studies and two animal models (FIGS. 6, 7, 9, and 11), F1mut-V induces robust immunogenicity and protective efficacy. It shows similar levels of F1- and V-specific antibody titers as the native F1-V, and no significant differences are observed in $T_H1$ vs $T_H2$ specific IgG subclass titers. Furthermore, F1mut-V overall shows stronger cytokine responses and conferred approximatey 100% protection in vaccinated mice and rats, including when very high doses of $Y.$ $pestis$ CO92, approximately 5,350 $LD_{50}$ for first challenge and approximately 20,000 $LD_{50}$ for re-challenge, are administered by the intranasal route (FIG. 9). The native F1-V, on the other hand, shows slightly lower protection (approximately 83%) upon re-challenge (FIG. 6).

The possibility of increasing the breadth and potency of F1-V vaccine by inclusion of YscF is tested by constructing an oligomerization deficient YscF35/67 mutant.[43] Such a vaccine might be effective even against those $Y.$ $pestis$ strains that contain variant V antigens or lack the capsule, but are highly virulent.[26] The mutated protein, purified as a soluble dimer, elicited YscF-specific antibodies on its own, and, when it is mixed with F1-V, it enhanced the induction of V-specific antibody titers as well as survival rate in mice (FIG. 6). While these results indicate enhanced potency of F1-V vaccine in the presence of YscF, more studies may be needed to determine if the cost of an additional protein can be justified for vaccine manufacture. On the other hand, the T4 displayed trivalent vaccine, F1mut-V-Soc-YscF (FIG. 5 and FIG. 7), might offer an alternative to incorporate YscF into the plague vaccine formulation.

$Y.$ $pestis$ infection stimulates IL-10 production which in turn suppresses the production of proinflammatory cytokines IFN-γ and TNF-α. Both IFN-γ and TNF-α are important for innate immunity, as well as to elicit $T_H1$ immune responses that might be essential for protection against pneumonic plague.[49,50,51] These immunomodulatory functions, in part, are attributed to the V antigen, specifically to the $NH_2$-terminal aa residues 31-49.[49] Deletion of these residues, or of the COOH-terminal aa residues 271-300 (V10 mutation), have been reported to abrogate the suppression of IFN-γ and TNF-α[41], presumably by preventing the interaction of V with toll like receptor 2 (TLR2) and CD14, the receptors of the innate immune system.[49,52] The disclosed studies showed that both the F1mut-V and F1mut-V10 immunogens produced similar levels of IFN-γ and other proinflammatory cytokines, such as IL-1α and upon stimulation ex-vivo of splenocytes from immunized mice with F1mut-V. However, TNF-α is induced to significantly higher levels in the F1mut-V10 group (FIG. 10), consistent with the published report.[41] However, the T4 nanoparticle decorated F1mut-V10 showed opposite trend, producing much reduced levels of TNF-α as well as IFN-γ and other cytokine responses than its F1mut-V counterpart, a result also correlated with lower protection against re-challenge [approximately 92% protection with T4 displayed F1mut-V10 vs approximately 100% protection with T4 displayed F1mut-V upon re-challenge with 20,000 $LD_{50}$ (FIG. 9, Panel C)]. Thus, the disclosed data does not show consistent enhancement of proinflammatory cytokines by the V10 mutation, hence it is questionable that replacing native V with V10 mutant would lead to a significant beneficial effect in a new plague vaccine design. On the other hand, from a structural standpoint, deletion of the aa residues 271-300 disrupts the coiled coil bridge between the $NH_2$- and COOH-domains of V[12], which would likely make V10 mutant a conformationally more flexible molecule and could adversely affect vaccine stability and efficacy.

Figure 11:
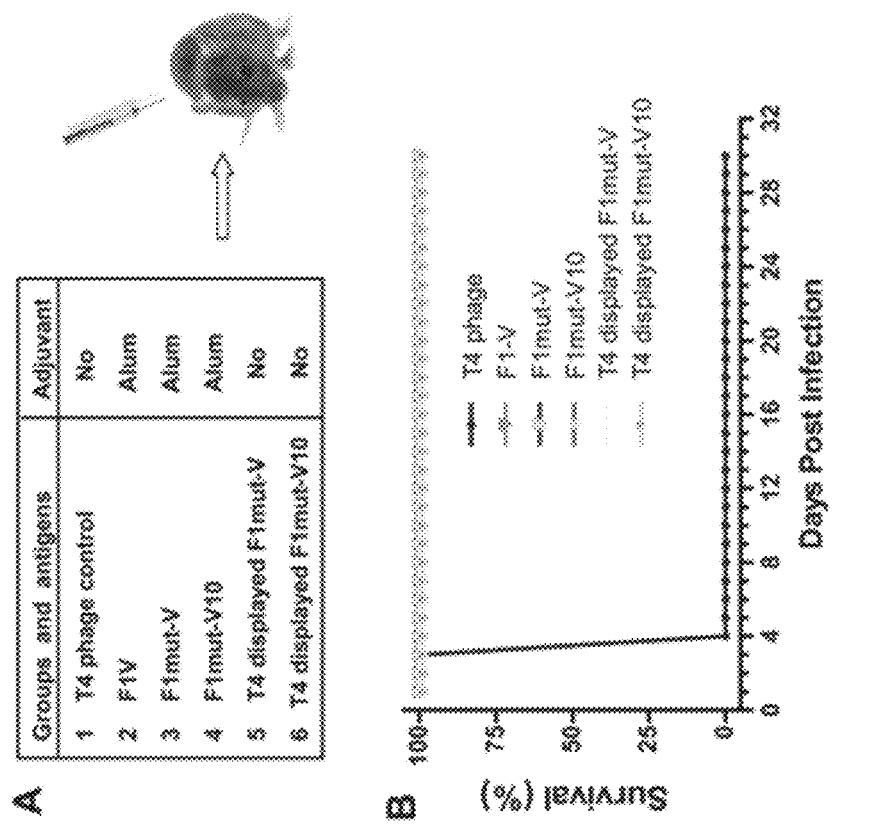
FIG. 11 is an illustration showing that mutated and T4 displayed plague antigens provided complete protection against $Y.$ $pestis$ CO92 in a Brown Norway rat model of pneumonic plague. Panel A shows vaccine formulations used in various groups, twelve rats per group. Panel B shows the survival of vaccinated rats against intranasal challenge with 5,000 $LD_{50}$ of $Y.$ $pestis$ CO92.

Although humoral immune responses are critical for protection against plague, several studies have shown that cell-mediated immunity also plays important roles.[23,53,54] Wang et al.[53] established the role of CD8+ T cells in protection of mice against pneumonic plague evoked by Y. pestis KIM 1001 strain. This study corroborated the earlier report of Parent et al.,[23] which concluded that plague vaccines that generate both humoral- and cell-mediated immune responses will be most effective. Likewise, Philipovskiy and Smiley (3) reported that mice vaccinated with a live Y. pestis vaccine primed both CD4+ and CD8+ T cells, which when passively transferred to naïve mice, provided protection against pulmonary Y. pestis infection.[54] The adjuvant-free T4 nanoparticle decorated F1mut-V induced robust F1- and V-specific antibody responses, as well as provided approximately 100% protection to mice and rats against very high doses of Y. pestis challenge (FIGS. 7, 9 and 11). In addition, T4 delivery induced balanced $T_H1$ and $T_H2$ responses with a potent $T_H1$ response, as evident from the induction of subclass IgG2a specific antibodies. Similar patterns are observed in our previous studies with the T4 displayed Human Immunodeficiency Virus-1 (HIV-1 p24 immunogen.[32] Presumably, the large size of the a T4 phage particle (capsid, approximatley 120 nm×86 nm; tail, approximately 100 nm) allows for its efficient uptake by the antigen presenting cells and cross-presentation to both MHC-I and MHC-II molecules, stimulating both the humoral and cellular arms of the immune system. It is also possible that the T4 phage DNA containing CpG might potentially serve as a $T_H1$-type of adjuvant. Indeed, studies have shown that F1-V vaccine adjuvanted with CpG or poly IC (also a $T_H1$ type adjuvant), given by the intranasal route, induced both $T_H1$ and TH2 responses, providing better protection to mice against bubonic and pneumonic plague.[55,56] Thus, T4 might be a particularly useful platform for plague vaccine design since clearance of the Y. pestis bacterium may require a balanced response that is generally not seen with the current F1-V vaccines.[46] It is also noted that, although the mechanistic basis for T4 responses is currently unknown, no adverse effects to T4 vaccination have been observed in many preclinical studies performed in mouse, rat, rabbit, and rhesus macaque models[31,57,58], or in a human trial where T4 phages is given orally.[59]

There has been a considerable urgency to develop a recombinant plague vaccine, but several concerns precluded licensing of current formulations. Disclosed studies have established that the F1mut-V recombinant vaccine is efficacious and easily manufacturable and should be seriously considered as a next generation plague vaccine. Future studies would include preclinical evaluation of protection against Y. pestis infection in cynomolgus macaques as well as African Green monkeys, potentially leading to human clinical trials. Although the soluble F1mut-V vaccine adjuvanted with alum would be relatively easy to manufacture, the phage T4 nanoparticle-decorated F1mut-V vaccine offers certain advantages. First, the T4 formulation provided enhanced vaccine potency in small animal models. Second, the T4 vaccine would not require an extraneous adjuvant, and third, additional antigens from other biodefense pathogens, such as the protective antigen (PA) from Bacillus anthracis could be incorporated into the same formulation generating a dual vaccine against both inhalation anthrax and pneumonic plague. The recent disclosed study demonstrats that the T4 displayed PA provided complete protection to Rhesus macaques against aerosol challenge with Ames spores of B. anthracis.[51] Fourth, the large interior of T4 head which has the capacity to package approximately 171 kb DNA can also be used to deliver DNA vaccines.[60] By combining protein display outside and DNA packaging inside the T4 nanoparticles can simultaneously deliver vaccine antigen(s) as well as vaccine DNAs, similar to that of the prime-boost strategy, potentially inducing robust and long-lasting immune responses. Finally, such prime-boost vaccines could be targeted to antigen-presenting dendritic cells (DCs) by displaying a DC-specific ligand on the capsid using Hoc, further stimulating the cell-mediated immunity. One or two doses of such potent nanoparticle vaccines might be sufficient to afford protection against multiple biothreat agents. With the recent data demonstrating the proof of the concept,[60] disclosed embodiments are currently developing these novel vaccine platforms, not only to defend against biowarfare pathogens but also to generate efficacious vaccines against complex infectious agents such as HIV-1 and malaria.

The practice of the present invention will employ, unless otherwise indicated, conventional techniques of microbiology, recombinant DNA technology and molecular biology and immunology, which are within the skills of the art.

Furthermore, in the present invention, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

All documents, patents, journal articles and other materials cited in the present application are incorporated herein by reference.

Although an example of the phage T4 nanoparticle arrayed immunogens comprising fusion proteins of F and V from Yersinia pestis are shown as used for generating plague vaccines, it will be appreciated that immunogens of other pathogens can be arrayed on the phage T4 nanoparticles for developing vaccines for other diseases.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

REFERENCES

The following references are referred to above and are incorporated herein by reference:
1. Perry R D, Fetherston J D (1997) *Yersinia pestis*—etiologic agent of plague. Clin Microbiol Rev 10: 35-66.
2. Kool J L (2005) Risk of person-to-person transmission of pneumonic plague. Clin Infect Dis 40: 1166-1172.
3. Rosenzweig J A, Jejelowo O, Sha J, Erova T E, Brackman S M, et al. (2011) Progress on plague vaccine development. Appl Microbiol Biotechnol 91: 265-286.
4. Inglesby T V, Dennis D T, Henderson D A, Bartlett J G, Ascher M S, et al. (2000) Plague as a biological weapon: medical and public health management. Working Group on Civilian Biodefense. JAMA 283: 2281-2290.
5. Zilinskas R A (2006) The anti-plague system and the Soviet biological warfare program. Crit. Rev Microbiol 32: 47-64.
6. Smiley S T (2008) Current challenges in the development of vaccines for pneumonic plague. Expert Rev Vaccines 7: 209-221.
7. Sha J, Kirtley M L, van Lier C J, Wang S, Erova T E, et al. (2012) Deletion of Braun lipoprotein encoding gene and altering the function of lipopolysaccharide attenuate plague bacterium. Infect Immun December 28: Epub ahead of print.
8. Feodorova V A, Corbel M J (2009) Prospects for new plague vaccines. Expert Rev Vaccines 8: 1721-1738.
9. Williamson E D, Oyston P C (2012) The natural history and incidence of *Yersinia pestis* and prospects for vaccination. J Med Microbiol 61: 911-918.
10. Zavialov A V, Berglund J, Pudney A F, Fooks L J, Ibrahim T M, et al. (2003) Structure and biogenesis of the capsular F1 antigen from *Yersinia pestis*: preserved folding energy drives fiber formation. Cell 113: 587-596.
11. Stenseth N C, Atshabar B B, Begon M, Belmain S R, Bertherat E, et al. (2008) Plague: past, present, and future. PLoS Med 5: e3.
12. Derewenda U, Mateja A, Devedjiev Y, Routzahn K M, Evdokimov A G, et al. (2004) The structure of *Yersinia pestis* V-antigen, an essential virulence factor and mediator of immunity against plague. Structure 12: 301-306.
13. Brubaker R R (2003) Interleukin-10 and inhibition of innate immunity to Yersiniae: roles of Yops and LcrV (V antigen). Infect Immun 71: 3673-3681.
14. Williamson E D, Eley S M, Griffin K F, Green M, Russell P, et al. (1995) A new improved sub-unit vaccine for plague: the basis of protection. FEMS Immunol Med Microbiol 12: 223-230.
15. Anderson G W, Jr., Heath D G, Bolt C R, Welkos S L, Friedlander A M (1998) Short- and long-term efficacy of single-dose subunit vaccines against *Yersinia pestis* in mice. Am J Trop Med Hyg 58: 793-799.
16. Heath D G, Anderson G W, Jr., Mauro J M, Welkos S L, Andrews G P, et al. (1998) Protection against experimental bubonic and pneumonic plague by a recombinant capsular F1-V antigen fusion protein vaccine. Vaccine 16: 1131-1137.
17. Williamson E D (2009) Plague. Vaccine 27 Suppl 4: D56-60.
18. Williamson E D, Flick-Smith H C, Lebutt C, Rowland C A, Jones S M, et al. (2005) Human immune response to a plague vaccine comprising recombinant F1 and V antigens. Infect Immun 73: 3598-3608.
19. Mizel S B, Graff A H, Sriranganathan N, Ervin S, Lees C J, et al. (2009) Flagellin-F1-V fusion protein is an effective plague vaccine in mice and two species of nonhuman primates. Clin Vaccine Immunol 16: 21-28.
20. Goodin J L, Nellis D F, Powell B S, Vyas V V, Enama J T, et al. (2007) Purification and protective efficacy of monomeric and modified *Yersinia pestis* capsular F1-V antigen fusion proteins for vaccination against plague. Protein Expr Purif 53: 63-79.
21. Goodin J L, Powell B S, Enama J T, Raab R W, McKown R L, et al. (2011) Purification and characterization of a recombinant *Yersinia pestis* V-F1 "Reversed" fusion protein for use as a new subunit vaccine against plague. Protein Expr Purif 76: 136-144.
22. Powell B S, Andrews G P, Enama J T, Jendrek S, Bolt C, et al. (2005) Design and testing for a nontagged F1-V fusion protein as vaccine antigen against bubonic and pneumonic plague. Biotechnol Prog 21: 1490-1510.
23. Parent M A, Berggren K N, Kummer L W, Wilhelm L B, Szaba F M, et al. (2005) Cell-mediated protection against pulmonary *Yersinia pestis* infection. Infect Immun 73: 7304-7310.
24. Friedlander A M, Welkos S L, Worsham P L, Andrews G P, Heath D G, et al. (1995) Relationship between virulence and immunity as revealed in recent studies of the F1 capsule of *Yersinia pestis*. Clin Infect Dis 21 Suppl 2: S178-181.
25. Worsham P L, Stein M P, Welkos S L (1995) Construction of defined F1 negative mutants of virulent *Yersinia pestis*. Contrib Microbiol Immunol 13: 325-328.
26. Roggenkamp A, Geiger A M, Leitritz L, Kessler A, Heesemann J (1997) Passive immunity to infection with *Yersinia* spp. mediated by anti-recombinant V antigen is dependent on polymorphism of V antigen. Infect Immun 65: 446-451.
27. Erova T E, Rosenzweig J A, Sha J, Suarez G, Sierra J C, et al. (2013) Evaluation of protective potential of *Yersinia pestis* outer membrane protein antigens as possible candidates for a new generation recombinant plague vaccine. Clin Vaccine Immunol 20: 227-238.
28. DeBord K L, Anderson D M, Marketon M M, Overheim K A, DePaolo R W, et al. (2006) Immunogenicity and protective immunity against bubonic plague and pneumonic plague by immunization of mice with the recombinant V10 antigen, a variant of LcrV. Infect Immun 74: 4910-4914.
29. Li Q, Shivachandra S B, Leppla S H, Rao V B (2006) Bacteriophage T4 capsid: a unique platform for efficient surface assembly of macromolecular complexes. J Mol Biol 363: 577-588.
30. Li Q, Shivachandra S B, Zhang Z, Rao V B (2007) Assembly of the small outer capsid protein, Soc, on bacteriophage T4: a novel system for high density display of multiple large anthrax toxins and foreign proteins on phage capsid. J Mol Biol 370: 1006-1019.
31. Shivachandra S B, Li Q, Peachman K K, Matyas G R, Leppla S H, et al. (2007) Multicomponent anthrax toxin display and delivery using bacteriophage T4. Vaccine 25: 1225-1235.
32. Sathaliyawala T, Rao M, Maclean D M, Birx D L, Alving C R, et al. (2006) Assembly of human immunodeficiency virus (HIV) antigens on bacteriophage T4: a novel in vitro approach to construct multicomponent HIV vaccines. J Virol 80: 7688-7698.

33. Black L W, Rao V B (2012) Structure, assembly, and DNA packaging of the bacteriophage T4 head. Adv Virus Res 82: 119-153.
34. Qin L, Fokine A, O'Donnell E, Rao V B, Rossmann M G (2009) Structure of the small outer capsid protein, Soc: a clamp for stabilizing capsids of T4-like phages. J Mol Biol 395: 728-741.
35. Fokine A, Islam M Z, Zhang Z, Bowman V D, Rao V B, et al. (2011) Structure of the three N-terminal immunoglobulin domains of the highly immunogenic outer capsid protein from a T4-like bacteriophage. J Virol 85: 8141-8148.
36. Sathaliyawala T, Islam M Z, Li Q, Fokine A, Rossmann M G, et al. (2010) Functional analysis of the highly antigenic outer capsid protein, Hoc, a virus decoration protein from T4-like bacteriophages. Mol Microbiol 77: 444-455.
37. Ishii T, Yanagida M (1977) The two dispensable structural proteins (soc and hoc) of the T4 phage capsid; their purification and properties, isolation and characterization of the defective mutants, and their binding with the defective heads in vitro. J Mol Biol 109: 487-514.
38. Andrews G P, Heath D G, Anderson G W, Jr., Welkos S L, Friedlander A M (1996) Fraction 1 capsular antigen (F1) purification from *Yersinia pestis* CO92 and from an *Escherichia coli* recombinant strain and efficacy against lethal plague challenge. Infect Immun 64: 2180-2187.
39. Miller J, Williamson E D, Lakey J H, Pearce M J, Jones S M, et al. (1998) Macromolecular organisation of recombinant *Yersinia pestis* F1 antigen and the effect of structure on immunogenicity. FEMS Immunol Med Microbiol 21: 213-221.
40. Musson J A, Morton M, Walker N, Harper H M, McNeill H V, et al. (2006) Sequential proteolytic processing of the capsular Caf1 antigen of *Yersinia pestis* for major histocompatibility complex class II-restricted presentation to T lymphocytes. J Biol Chem 281: 26129-26135.
41. Overheim K A, Depaolo R W, Debord K L, Morrin E M, Anderson D M, et al. (2005) LcrV plague vaccine with altered immunomodulatory properties. Infect Immun 73: 5152-5159.
42. Matson J S, Durick K A, Bradley D S, Nilles M L (2005) Immunization of mice with YscF provides protection from *Yersinia pestis* infections. BMC Microbiol 5: 38.
43. Davis A J, Mecsas J (2007) Mutations in the *Yersinia pseudotuberculosis* type III secretion system needle protein, YscF, that specifically abrogate effector translocation into host cells. J Bacteriol 189: 83-97.
44. Quenee L E, Schneewind O (2009) Plague vaccines and the molecular basis of immunity against *Yersinia pestis*. Hum Vaccin 5: 817-823.
45. Smiley S T (2008) Immune defense against pneumonic plague. Immunol Rev 225: 256-271.
46. Do Y, Park C G, Kang Y S, Park S H, Lynch R M, et al. (2008) Broad T cell immunity to the LcrV virulence protein is induced by targeted delivery to DEC-205/CD205-positive mouse dendritic cells. Eur J Immunol 38: 20-29.
47. Agar S L, Sha J, Foltz S M, Erova T E, Walberg K G, et al. (2009) Characterization of the rat pneumonic plague model: infection kinetics following aerosolization of *Yersinia pestis* CO92. Microbes Infect 11: 205-214.
48. Chalton D A, Musson J A, Flick-Smith H, Walker N, McGregor A, et al. (2006) Immunogenicity of a *Yersinia pestis* vaccine antigen monomerized by circular permutation. Infect Immun 74: 6624-6631.
49. Sing A, Rost D, Tvardovskaia N, Roggenkamp A, Wiedemann A, et al. (2002) *Yersinia* V-antigen exploits toll-like receptor 2 and CD14 for interleukin 10-mediated immunosuppression. J Exp Med 196: 1017-1024.
50. Sodhi A, Sharma R K, Batra H V (2005) *Yersinia* rLcrV and rYopB inhibits the activation of murine peritoneal macrophages in vitro. Immunol Lett 99: 146-152.
51. Lin J S, Park S, Adamovicz J J, Hill J, Bliska J B, et al. (2010) TNFalpha and IFNgamma contribute to F1/LcrV-targeted immune defense in mouse models of fully virulent pneumonic plague. Vaccine 29: 357-362.
52. Kopp E, Medzhitov R (2002) A plague on host defense. J Exp Med 196: 1009-1012.
53. Wang S, Goguen J D, Li F, Lu S (2011) Involvement of $CD8^+$ T cell-mediated immune responses in LcrV DNA vaccine induced protection against lethal *Yersinia pestis* challenge. Vaccine 29: 6802-6809.
54. Philipovskiy A V, Smiley S T (2007) Vaccination with live *Yersinia pestis* primes CD4 and CD8 T cells that synergistically protect against lethal pulmonary *Y. pestis* infection. Infect Immun 75: 878-885.
55. Amemiya K, Meyers J L, Rogers T E, Fast R L, Bassett A D, et al. (2009) CpG oligodeoxynucleotides augment the murine immune response to the *Yersinia pestis* F1-V vaccine in bubonic and pneumonic models of plague. Vaccine 27: 2220-2229.
56. Hickey A J, Lin J S, Kummer L W, Szaba F M, Duso D K, et al. (2013) Intranasal prophylaxis with CpG oligodeoxynucleotide can protect against *Yersinia pestis* infection. Infect Immun 81 (6): 2123-2132.
57. Peachman K K, Li Q, Matyas G R, Shivachandra S B, Lovchik J, et al. (2012) Anthrax vaccine antigen-adjuvant formulations completely protect New Zealand white rabbits against challenge with *Bacillus anthracis* Ames strain spores. Clin Vaccine Immunol 19: 11-16.
58. Rao M, Peachman K K, Li Q, Matyas G R, Shivachandra S B, et al. (2011) Highly effective generic adjuvant systems for orphan or poverty-related vaccines. Vaccine 29: 873-877.
59. Bruttin A, Brussow H (2005) Human volunteers receiving *Escherichia coli* phage T4 orally: a safety test of phage therapy. Antimicrob Agents Chemother 49: 2874-2878.
60. Tao P, Mahalingam M, Marasa B S, Zhang Z, Chopra A K, et al. (2013) In vitro and in vivo delivery of genes and proteins using the bacteriophage T4 DNA packaging machine. Proc Natl Acad Sci USA 110: 5846-5851.
61. Horton R M, Hunt H D, Ho S N, Pullen J K, Pease L R (1989) Engineering hybrid genes without the use of restriction enzymes: gene splicing by overlap extension. Gene 77: 61-68.
62. Pettersen E F, Goddard T D, Huang C C, Couch G S, Greenblatt D M, et al. (2004) UCSF Chimera—a visualization system for exploratory research and analysis. J Comput Chem 25: 1605-1612.
63. Hu X, Zhou W, Udaka K, Mamitsuka H, Zhu S (2010) MetaMHC: a meta approach to predict peptides binding to MHC molecules. Nucleic Acids Res 38: W474-479.
64. Brito L A, Singh M (2011) Acceptable levels of endotoxin in vaccine formulations during preclinical research. J Pharm Sci 100: 34-37.
65. Agar S L, Sha J, Foltz S M, Erova T E, Walberg K G, et al. (2008) Characterization of a mouse model of plague after aerosolization of *Yersinia pestis* CO92. Microbiology 154: 1939-1948.

What is claimed is:

1. A recombinant protein comprising a mutated F1 antigen of *Yersinia pestis*, wherein the mutated F1 antigen of *Yersinia pestis* is developed from a native F1 antigen of *Yersinia pestis* by the following steps:
    deleting an $NH_2$-terminal β-strand of F1 antigen of *Yersinia pestis* from an $NH_2$-terminus of the native F1 antigen of *Yersinia pestis* to thereby form an $NH_2$-terminal β-strand deleted F1,
    fusing the $NH_2$-terminal β-strand of F1 antigen of *Yersinia pestis* to a COOH-terminus of the $NH_2$-terminal β-strand deleted F1 via a first peptide linker to thereby form an NH2-terminal β-strand transplanted F1, and
    duplicating an $NH_2$-terminal amino acid sequence of F1 antigen of *Yersinia pestis* flanking the $NH_2$-terminal β-strand of F1 antigen of *Yersinia pestis* at a COOH-terminus of the NH2-terminal β-strand transplanted F1 to thereby form a mutated F1 antigen of *Yersinia pestis*.

2. A recombinant protein of claim 1, wherein the $NH_2$-terminal β-strand of F1 antigen of *Yersinia pestis* comprises amino acid residues from position 1 to position 14 of the native F1 antigen of *Yersinia pestis*.

3. A recombinant protein of claim 1, wherein the $NH_2$-terminal amino acid sequence of F1 antigen of *Yersinia pestis* that flanks the $NH_2$-terminal β-strand of F1 antigen of *Yersinia pestis* comprises SEQ ID NO 1.

4. A recombinant protein of claim 1, wherein the first peptide linker comprises a two amino acid linker Ser-Ala.

5. A recombinant protein of claim 1, wherein the mutated F1 antigen of *Yersinia pestis* has two hexa-histidine tags of SEQ ID NO 2, and wherein one of the two hexa-histidine tags of SEQ ID NO 2 is fused at an $NH_2$-terminus of the mutated F1 antigen of *Yersinia pestis* and the other one of the two hexa-histidine tags of SEQ ID NO 2 is fused at a COOH-terminus of the mutated F1 antigen of *Yersinia pestis*.

6. A recombinant protein of claim 1 comprising a V antigen of *Yersinia pestis* and a second peptide linker, wherein the mutated F1 antigen of *Yersinia pestis* is fused through the second peptide linker to the V antigen of *Yersinia pestis* to thereby form a fusion protein F1mut-V.

7. A recombinant protein of claim 6, wherein the second peptide linker comprises a two amino acid linker Gly-Ser.

8. A recombinant protein of claim 7, wherein a COOH-terminus of the second peptide linker is directly joined to an $NH_2$-terminus of the V antigen of *Yersinia pestis* and an $NH_2$-terminus of the linker is directly linked to a COOH-terminus of the mutated F1 antigen of *Yersinia pestis*.

9. A recombinant protein of claim 8, wherein the fusion protein F1mut-V has two hexa-histidine tags of SEQ ID NO 2, and wherein one of the two hexa-histidine tags of SEQ ID NO 2 is fused at an $NH_2$-terminus of the fusion protein F1mut-V and the other one of the two hexa-histidine tags of SEQ ID NO 2 is fused at a COOH-terminus of the fusion protein F1mut-V.

10. A recombinant protein of claim 9, wherein thirty COOH-terminal amino acid residues from 270 to 300 of the V antigen of *Yersinia pestis* are deleted to thereby form a fusion protein F1mut-V10.

11. A method for producing a recombinant protein comprising the following steps:
    deleting an $NH_2$-terminal β-strand of F1 antigen of *Yersinia pestis* from an $NH_2$-terminus of a native F1 antigen of *Yersinia pestis* to thereby form an $NH_2$-terminal β-strand deleted F1,
    fusing the $NH_2$-terminal β-strand of F1 antigen of *Yersinia pestis* to a COOH-terminus of the $NH_2$-terminal β-strand deleted F1 via a first peptide linker to thereby form an NH2-terminal β-strand transplanted F1, and
    duplicating an $NH_2$-terminal amino acid sequence of F1 antigen of *Yersinia pestis* flanking the $NH_2$-terminal β-strand of F1 antigen of *Yersinia pestis* at a COOH-terminus of the NH2-terminal β-strand transplanted F1 to thereby form a mutated F1 antigen of *Yersinia pestis*.

12. A method of claim 11, wherein the $NH_2$-terminal β-strand of F1 antigen of *Yersinia pestis* comprises amino acids from position 1 to position 14 of the native F1 antigen of *Yersinia pestis*.

13. A method of claim 12, wherein the $NH_2$-terminal amino acid sequence of F1 antigen of *Yersinia pestis* flanking the $NH_2$-terminal β-strand of F1 antigen of *Yersinia pestis* comprises SEQ ID NO 1.

14. A method of claim 13, wherein the first peptide linker comprises a two amino acid linker Ser-Ala.

15. A method of claim 14, wherein the mutated F1 antigen of *Yersinia pestis* has two hexa-histidine tags of SEQ ID NO 2, and wherein one of the two hexa-histidine tags of SEQ ID NO 2 is fused at an $NH_2$-terminus of the mutated F1 antigen of *Yersinia pestis* and the other one of the two hexa-histidine tags of SEQ ID NO 2 is fused at a COOH-terminus of the mutated F1 antigen of *Yersinia pestis*.

16. A method of claim 14 comprising a step of fusing a V antigen of *Yersinia pestis* through a second peptide linker to the mutated F1 antigen of *Yersinia pestis* to thereby form a fusion protein F1mut-V, wherein a COOH-terminus of the second peptide linker is directly joined to an $NH_2$-terminus of the V antigen of *Yersinia pestis* and an $NH_2$-terminus of the linker is directly joined to a COOH-terminus of the mutated F1 antigen of *Yersinia pestis*.

17. A method of claim 16, wherein the fusion protein F1mut-V has two hexa-histidine tags of SEQ ID NO 2, and wherein one of the two hexa-histidine tags of SEQ ID NO 2 is fused at an $NH_2$-terminus of the fusion protein F1mut-V and the other one of the two hexa-histidine tags of SEQ ID NO 2 is fused at a COOH-terminus of the fusion protein F1mut-V.

18. A method of claim 17 comprising a step of deleting thirty COOH-terminal amino acid residues from 270 to 300 of the V antigen of *Yersinia pestis* to thereby form a fusion protein F1mut-V10.

* * * * *

SEQUENCE LISTING

<160> NUMBER OF SEQ ID NOS: 77

<210> SEQ ID NO 1
<211> LENGTH: 7
<212> TYPE: PRT
<213> ORGANISM: Yersinia pestis

<400> SEQUENCE: 1

Glu Pro Ala Arg Ile Thr Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Artificial peptide used for protein
      purification.

<400> SEQUENCE: 2

Leu Glu His His His His His His
1               5

<210> SEQ ID NO 3
<211> LENGTH: 4
<212> TYPE: PRT
<213> ORGANISM: Artificial Sequence
<220> FEATURE:
<223> OTHER INFORMATION: Artificial protein sequence of a peptide linker

<400> SEQUENCE: 3

Gly Gly Gly Gly
1

<210> SEQ ID NO 4
<211> LENGTH: 6
<212> TYPE: PRT
<213> ORGANISM: Artificial Sequence
<220> FEATURE:
<223> OTHER INFORMATION: Artificial protein sequence of a peptide linker

<400> SEQUENCE: 4

Gly Gly Gly Asn Gly Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Artificial protein sequence of a peptide linker

<400> SEQUENCE: 5

Gly Gly Gly Ser
1

<210> SEQ ID NO 6
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 6

Tyr Thr Asp Ala Val Thr Val Thr Val
1               5

```
<210> SEQ ID NO 7
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 7

Phe Thr Asp Ala Ala Gly Asp Pro Met
1               5

<210> SEQ ID NO 8
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 8

Ser Thr Thr Ala Thr Ala Thr Leu Val
1               5

<210> SEQ ID NO 9
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 9

Leu Thr Ala Ser Thr Thr Ala Thr Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 10

Ala Thr Gly Ser Gln Asp Phe Phe Val
1               5

<210> SEQ ID NO 11
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 11

Phe Thr Ser Gln Asp Gly Asn Asn His
1               5

<210> SEQ ID NO 12
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope
```

```
<400> SEQUENCE: 12

Glu Pro Ala Arg Ile Thr Leu Thr Tyr
1               5

<210> SEQ ID NO 13
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 13

Thr Thr Ser Thr Ser Val Asn Phe Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 14

Asn Leu Val Gly Asp Asp Val Val Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 15

Ala Thr Ala Thr Leu Val Glu Pro Ala
1               5

<210> SEQ ID NO 16
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 16

Glu Leu Leu Val Gly Thr Leu Thr Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 17

Gly Thr Leu Thr Leu Gly Gly Tyr Lys
1               5

<210> SEQ ID NO 18
<211> LENGTH: 9
```

```
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 18

Arg Ser Ile Gly Ser Lys Gly Gly Lys
1               5

<210> SEQ ID NO 19
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 19

Lys Gly Gly Lys Leu Ala Ala Gly Lys
1               5

<210> SEQ ID NO 20
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 20

Phe Phe Val Arg Ser Ile Gly Ser Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 21

Ala Gly Asp Pro Met Tyr Leu Thr Phe
1               5

<210> SEQ ID NO 22
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 22

Val Leu Ala Thr Gly Ser Gln Asp Phe
1               5

<210> SEQ ID NO 23
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 23

Met Tyr Leu Thr Phe Thr Ser Gln Asp
```

<210> SEQ ID NO 24
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 24

Ser Gln Asp Gly Asn Asn His Gln Phe
1               5

<210> SEQ ID NO 25
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 25

Asp Thr Glu Leu Leu Val Gly Thr Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 26

Asp Val Val Leu Ala Thr Gly Ser Gln
1               5

<210> SEQ ID NO 27
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 27

Thr Asp Ala Ala Gly Asp Pro Met Tyr
1               5

<210> SEQ ID NO 28
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 28

Pro Ala Arg Ile Thr Leu Thr Tyr Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Artificial protein sequence of a predicted CD8+

T cell epitope

<400> SEQUENCE: 29

Lys Thr Gly Thr Thr Ser Thr Ser Val
1               5

<210> SEQ ID NO 30
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 30

Val Gly Thr Leu Thr Leu Gly Gly Tyr
1               5

<210> SEQ ID NO 31
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 31

Gly Gly Lys Leu Ala Ala Gly Lys Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 32

Gly Thr Thr Ser Thr Ser Val Asn Phe
1               5

<210> SEQ ID NO 33
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 33

Ser Gln Asp Phe Phe Val Arg Ser Ile
1               5

<210> SEQ ID NO 34
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 34

Ala Thr Leu Val Glu Pro Ala Arg Ile
1               5

<210> SEQ ID NO 35

```
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 35

Leu Thr Tyr Lys Glu Gly Ala Pro Ile
1               5

<210> SEQ ID NO 36
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 36

Ala Ser Thr Thr Ala Thr Ala Thr Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 37

Thr Ala Thr Leu Val Glu Pro Ala Arg
1               5

<210> SEQ ID NO 38
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 38

Thr Gly Ser Gln Asp Phe Phe Val Arg
1               5

<210> SEQ ID NO 39
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 39

Asp Ala Ala Gly Asp Pro Met Tyr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 40
```

```
Thr Ser Val Asn Phe Thr Asp Ala Ala
1               5
```

<210> SEQ ID NO 41
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 41

```
Ser Pro Lys Val Asn Gly Glu Asn Leu
1               5
```

<210> SEQ ID NO 42
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 42

```
Leu Val Glu Pro Ala Arg Ile Thr Leu
1               5
```

<210> SEQ ID NO 43
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 43

```
Gly Lys Tyr Thr Asp Ala Val Thr Val
1               5
```

<210> SEQ ID NO 44
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 44

```
Asn His Gln Phe Thr Thr Lys Val Ile
1               5
```

<210> SEQ ID NO 45
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 45

```
Thr Glu Leu Leu Val Gly Thr Leu Thr
1               5
```

<210> SEQ ID NO 46
<211> LENGTH: 9
<212> TYPE: PRT
<213> ORGANISM: Artificial Sequence
<220> FEATURE:

```
<223> OTHER INFORMATION: Artificial protein sequence of a predicted CD8+
      T cell epitope

<400> SEQUENCE: 46

Ser Arg Asp Phe Asp Ile Ser Pro Lys
1               5

<210> SEQ ID NO 47
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 47

Ala Arg Ile Thr Leu Thr Tyr Lys Glu
1               5

<210> SEQ ID NO 48
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 48

Asp Pro Met Tyr Leu Thr Phe Thr Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 49

Leu Ala Thr Gly Ser Gln Asp Phe Phe
1               5

<210> SEQ ID NO 50
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 50

Tyr Lys Glu Gly Ala Pro Ile Thr Ile
1               5

<210> SEQ ID NO 51
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 51

His Gln Phe Thr Thr Lys Val Ile Gly
1               5
```

```
<210> SEQ ID NO 52
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 52

Lys Glu Gly Ala Pro Ile Thr Ile Met
1               5

<210> SEQ ID NO 53
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 53

Gly Glu Asn Leu Val Gly Asp Asp Val
1               5

<210> SEQ ID NO 54
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 54

Arg Asp Phe Asp Ile Ser Pro Lys Val
1               5

<210> SEQ ID NO 55
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 55

Ala Asp Leu Thr Ala Ser Thr Thr Ala
1               5

<210> SEQ ID NO 56
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 56

Ala Ala Gly Lys Tyr Thr Asp Ala Val
1               5

<210> SEQ ID NO 57
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

<400> SEQUENCE: 57
```

```
Ala Pro Ile Thr Ile Met Asp Asn Gly
1               5
```

```
<210> SEQ ID NO 58
<211> LENGTH: 21
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 58

Lys Val Asn Gly Glu Asn Leu Val Gly Asp Asp Val Val Leu Ala Thr
1               5                   10                  15

Gly Ser Gln Asp Phe
            20
```

```
<210> SEQ ID NO 59
<211> LENGTH: 19
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 59

Gln Phe Thr Thr Lys Val Ile Gly Lys Asp Ser Arg Asp Phe Asp Ile
1               5                   10                  15

Ser Pro Lys
```

```
<210> SEQ ID NO 60
<211> LENGTH: 19
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 60

Asp Pro Met Tyr Leu Thr Phe Thr Ser Gln Asp Gly Asn Asn His Gln
1               5                   10                  15

Phe Thr Thr
```

```
<210> SEQ ID NO 61
<211> LENGTH: 28
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 61

Asn Ile Asp Thr Glu Leu Leu Val Gly Thr Leu Thr Leu Gly Gly Tyr
1               5                   10                  15

Lys Thr Gly Thr Thr Ser Thr Ser Val Asn Phe Thr
            20                  25
```

```
<210> SEQ ID NO 62
<211> LENGTH: 15
<212> TYPE: PRT
<213> ORGANISM: Artificial Sequence
<220> FEATURE:
<223> OTHER INFORMATION: Artificial protein sequence of a predicted CD4+
      T cell epitope
```

```
<400> SEQUENCE: 62

Ala Gly Lys Tyr Thr Asp Ala Val Thr Val Thr Val Ser Asn Gln
1               5                   10                  15

<210> SEQ ID NO 63
<211> LENGTH: 19
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 63

Asn Ile Asp Thr Glu Leu Leu Val Gly Thr Leu Thr Leu Gly Gly Tyr
1               5                   10                  15

Lys Thr Gly

<210> SEQ ID NO 64
<211> LENGTH: 16
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 64

Asp Pro Met Tyr Leu Thr Phe Thr Ser Gln Asp Gly Asn Asn His Gln
1               5                   10                  15

<210> SEQ ID NO 65
<211> LENGTH: 20
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 65

Asp Ala Ala Gly Asp Pro Met Tyr Leu Thr Phe Thr Ser Gln Asp Gly
1               5                   10                  15

Asn Asn His Gln
            20

<210> SEQ ID NO 66
<211> LENGTH: 18
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 66

Ala Asp Leu Thr Ala Ser Thr Thr Ala Thr Ala Thr Leu Val Glu Pro
1               5                   10                  15

Ala Arg

<210> SEQ ID NO 67
<211> LENGTH: 17
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 67
```

```
Leu Ala Ala Gly Lys Tyr Thr Asp Ala Val Thr Val Thr Val Ser Asn
1               5                   10                  15
Gln

<210> SEQ ID NO 68
<211> LENGTH: 17
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 68

Thr Leu Gly Gly Tyr Lys Thr Gly Thr Thr Ser Thr Ser Val Asn Phe
1               5                   10                  15
Thr

<210> SEQ ID NO 69
<211> LENGTH: 21
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 69

Ala Thr Gly Ser Gln Asp Phe Phe Val Arg Ser Ile Gly Ser Lys Gly
1               5                   10                  15

Gly Lys Leu Ala Ala
            20

<210> SEQ ID NO 70
<211> LENGTH: 19
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 70

Ala Arg Ile Thr Leu Thr Tyr Lys Glu Gly Ala Pro Ile Thr Ile Met
1               5                   10                  15

Asp Asn Gly

<210> SEQ ID NO 71
<211> LENGTH: 15
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 71

Ala Asp Leu Thr Ala Ser Thr Thr Ala Thr Ala Thr Leu Val Glu
1               5                   10                  15

<210> SEQ ID NO 72
<211> LENGTH: 22
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 72
```

Asn Gly Asn Ile Asp Thr Glu Leu Leu Val Gly Thr Leu Thr Leu Gly
1               5                   10                  15

Gly Tyr Lys Thr Gly Thr
            20

<210> SEQ ID NO 73
<211> LENGTH: 16
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 73

Thr Glu Leu Leu Val Gly Thr Leu Thr Leu Gly Gly Tyr Lys Thr Gly
1               5                   10                  15

<210> SEQ ID NO 74
<211> LENGTH: 20
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 74

Thr Gly Ser Gln Asp Phe Phe Val Arg Ser Ile Gly Ser Lys Gly Gly
1               5                   10                  15

Lys Leu Ala Ala
            20

<210> SEQ ID NO 75
<211> LENGTH: 38
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 75

Gln Phe Thr Thr Lys Val Ile Gly Lys Asp Ser Arg Asp Phe Asp Ile
1               5                   10                  15

Ser Pro Lys Val Asn Gly Glu Asn Leu Val Gly Asp Asp Val Val Leu
            20                  25                  30

Ala Thr Gly Ser Gln Asp
        35

<210> SEQ ID NO 76
<211> LENGTH: 15
<212> TYPE: PRT
<213> ORGANISM: Artificial Sequence
<220> FEATURE:
<223> OTHER INFORMATION: Artificial protein sequence of a predicted CD4+
      T cell epitope

<400> SEQUENCE: 76

Asp Asn Gly Asn Ile Asp Thr Glu Leu Leu Val Gly Thr Leu Thr
1               5                   10                  15

<210> SEQ ID NO 77
<211> LENGTH: 9
<212> TYPE: PRT
<213> ORGANISM: Artificial Sequence
<220> FEATURE:
<223> OTHER INFORMATION: Artificial protein sequence of a predicted CD8+
      T cell epitope

```
<400> SEQUENCE: 77

Leu Ala Ala Gly Lys Tyr Thr Asp Ala
1               5
```